(12) United States Patent
Ferlic

(10) Patent No.: US 11,590,335 B2
(45) Date of Patent: Feb. 28, 2023

(54) STERILIZING DEVICE WITH PINCH ACTUATED CAP AND HOUSING

(71) Applicant: Michael J. Ferlic, Roseville, MN (US)

(72) Inventor: Michael J. Ferlic, Roseville, MN (US)

(73) Assignee: 1WORLDVISTA MEDICAL, INC., Naples, FL (US)

( * ) Notice: Subject to any disclaimer, the term of this patent is extended or adjusted under 35 U.S.C. 154(b) by 829 days.

(21) Appl. No.: 15/437,250

(22) Filed: Feb. 20, 2017

(65) Prior Publication Data
US 2017/0157386 A1    Jun. 8, 2017

Related U.S. Application Data

(63) Continuation of application No. 13/495,937, filed on Jun. 13, 2012, now Pat. No. 9,572,904, which is a
(Continued)

(51) Int. Cl.
*A61L 2/16* (2006.01)
*A61M 39/16* (2006.01)
(Continued)

(52) U.S. Cl.
CPC .............. *A61M 39/162* (2013.01); *A61L 2/18* (2013.01); *A61L 2/235* (2013.01); *A61M 39/16* (2013.01);
(Continued)

(58) Field of Classification Search
CPC .............. A61L 2/16; A61L 2/18; A61L 2/186; A61L 2/183
See application file for complete search history.

(56) References Cited

U.S. PATENT DOCUMENTS

| 1,374,851 A | 4/1921 | Hirth |
| 2,030,911 A | 2/1936 | Borden |

(Continued)

FOREIGN PATENT DOCUMENTS

| EP | 0227219 B1 | 12/1990 |
| EP | 2606930 A1 | 6/2013 |

(Continued)

OTHER PUBLICATIONS

Sciencing "How Does Alcohol Kill Bacteria?", updated Apr. 25, 2018. (Year: 2018).*
(Continued)

*Primary Examiner* — Donald R Spamer
(74) *Attorney, Agent, or Firm* — Dicke, Billig & Czaja, PLLC

(57) ABSTRACT

Devices and methods for sterilizing the outer and inner surfaces of a working end-site of a medical device such as a catheter hub, luer connector, luer component, needleless access site, and/or access port are discussed. The sterilizing device can include a housing, a sterilizing element including an antipathogenic agent configured for sterilizing the working end-site of a medical device, and a cap hingedly coupled to the housing and configured to hermetically seal the sterilizing element within the housing. One or more features on the cap and housing serve to hermetically seal the cap to the housing prior to use.

110 Claims, 32 Drawing Sheets

Related U.S. Application Data continuation-in-part of application No. 12/624,154, filed on Nov. 23, 2009, now Pat. No. 8,252,247, which is a continuation-in-part of application No. 12/300,717, filed as application No. PCT/US2008/076864 on Sep. 18, 2008, now Pat. No. 8,273,303.

(60) Provisional application No. 61/496,298, filed on Jun. 13, 2011, provisional application No. 61/050,769, filed on May 6, 2008.

(51) Int. Cl.
| | |
|---|---|
| A61L 2/18 | (2006.01) |
| A61M 39/20 | (2006.01) |
| A61L 2/235 | (2006.01) |
| A61B 90/40 | (2016.01) |
| A61M 5/31 | (2006.01) |

(52) U.S. Cl.
CPC ............ *A61M 39/20* (2013.01); *A61B 90/40* (2016.02); *A61L 2202/24* (2013.01); *A61M 2005/3106* (2013.01); *Y10T 29/49826* (2015.01)

(56) References Cited

U.S. PATENT DOCUMENTS

| | | | |
|---|---|---|---|
| 3,557,989 | A | 1/1971 | Balda |
| 3,661,666 | A | 5/1972 | Foster et al. |
| 3,976,311 | A | 8/1976 | Spendlove |
| 3,987,930 | A | 10/1976 | Fuson |
| 4,340,052 | A | 7/1982 | Dennehey et al. |
| 4,354,490 | A | 10/1982 | Rogers et al. |
| 4,366,816 | A | 1/1983 | Bayard et al. |
| 4,405,312 | A | 9/1983 | Gross et al. |
| 4,417,890 | A | 11/1983 | Dennehey et al. |
| 4,432,764 | A | 2/1984 | Lopez |
| 4,440,207 | A | 4/1984 | Genatempo et al. |
| 4,445,896 | A | 5/1984 | Gianturco |
| 4,551,137 | A | 11/1985 | Osborne |
| 4,551,146 | A | 11/1985 | Rogers |
| 4,624,664 | A | 11/1986 | Peluso et al. |
| 4,644,966 | A | 2/1987 | Ferrari |
| 5,063,049 | A | 11/1991 | Billings |
| 5,072,855 | A | 12/1991 | Herzig |
| 5,205,821 | A | 4/1993 | Kruger et al. |
| 5,242,425 | A | 9/1993 | White et al. |
| 5,311,634 | A * | 5/1994 | Andros ............ H01L 21/67046 15/102 |
| 5,353,968 | A | 10/1994 | Good, Jr. |
| 5,413,561 | A | 5/1995 | Fischell et al. |
| 5,490,736 | A | 2/1996 | Haber et al. |
| 5,554,135 | A | 9/1996 | Menyhay |
| 5,569,206 | A | 10/1996 | Gorman, Jr. et al. |
| 5,620,527 | A | 4/1997 | Kramer et al. |
| 5,694,978 | A | 12/1997 | Heilmann et al. |
| 5,727,682 | A | 3/1998 | Abidin et al. |
| 5,743,892 | A | 4/1998 | Loh et al. |
| 5,792,120 | A | 8/1998 | Menyhay |
| 5,829,613 | A | 11/1998 | Wohlgemuth et al. |
| 5,989,229 | A | 11/1999 | Chiappetta |
| 6,003,556 | A | 12/1999 | Brugger et al. |
| 6,045,539 | A | 4/2000 | Menyhay |
| 6,116,468 | A | 9/2000 | Nilson |
| 6,416,323 | B1 | 7/2002 | Grenfell et al. |
| 6,517,508 | B1 | 2/2003 | Utterberg et al. |
| 6,764,471 | B2 | 7/2004 | Lee |
| 6,767,509 | B1 | 7/2004 | Griesbach |
| 7,041,083 | B2 | 5/2006 | Chu et al. |
| 7,083,605 | B2 | 8/2006 | Miyahara |
| 7,198,611 | B2 | 4/2007 | Connell et al. |
| 7,282,186 | B2 | 10/2007 | Lake, Jr. et al. |
| 7,294,308 | B2 | 11/2007 | Kacian et al. |
| 7,682,561 | B2 | 3/2010 | Davis et al. |
| 7,763,006 | B2 | 7/2010 | Tennican |
| 7,780,794 | B2 | 8/2010 | Rogers et al. |
| 7,799,010 | B2 | 9/2010 | Tennican |
| 7,972,322 | B2 | 7/2011 | Tennican et al. |
| 8,065,773 | B2 | 11/2011 | Vaillancourt et al. |
| 8,162,899 | B2 | 4/2012 | Tennican et al. |
| 8,172,825 | B2 | 5/2012 | Solomon et al. |
| 8,177,761 | B2 | 5/2012 | Howlett et al. |
| 8,197,749 | B2 | 6/2012 | Howlett et al. |
| 8,231,587 | B2 | 7/2012 | Solomon et al. |
| 8,252,247 | B2 | 8/2012 | Ferlic |
| 8,262,643 | B2 | 9/2012 | Tennican |
| 8,273,303 | B2 | 9/2012 | Ferlic et al. |
| 8,328,767 | B2 | 12/2012 | Solomon et al. |
| 8,336,152 | B2 | 12/2012 | Vaillancourt et al. |
| 8,343,112 | B2 | 1/2013 | Solomon et al. |
| 8,388,894 | B2 | 3/2013 | Colantonio et al. |
| 8,628,501 | B2 | 1/2014 | Hadden |
| 8,784,388 | B2 | 7/2014 | Charles et al. |
| 8,808,637 | B2 | 8/2014 | Ferlic |
| 8,828,327 | B2 | 9/2014 | Colantonio et al. |
| 9,078,992 | B2 | 7/2015 | Ziebol et al. |
| 2002/0168530 | A1 | 11/2002 | Tingey et al. |
| 2003/0017073 | A1* | 1/2003 | Eckhardt ............... A61L 2/10 422/24 |
| 2004/0031120 | A1* | 2/2004 | Cherian ............ A41D 19/0024 15/227 |
| 2005/0045031 | A1 | 3/2005 | Rajagopalan et al. |
| 2005/0075611 | A1 | 4/2005 | Hetzler et al. |
| 2005/0124970 | A1 | 6/2005 | Kunin et al. |
| 2005/0242204 | A1 | 11/2005 | Ness et al. |
| 2006/0030827 | A1* | 2/2006 | Raulerson ............ A61M 39/16 604/267 |
| 2007/0106205 | A1 | 5/2007 | Connell et al. |
| 2007/0112333 | A1 | 5/2007 | Hoang et al. |
| 2007/0225660 | A1* | 9/2007 | Lynn ................... A61M 39/045 604/265 |
| 2007/0282280 | A1 | 12/2007 | Tennican et al. |
| 2008/0019889 | A1 | 1/2008 | Rogers et al. |
| 2008/0021381 | A1 | 1/2008 | Lurvey et al. |
| 2008/0038167 | A1 | 2/2008 | Lynn |
| 2008/0039803 | A1* | 2/2008 | Lynn ........................ A61L 2/18 604/256 |
| 2008/0086091 | A1 | 4/2008 | Anderson et al. |
| 2008/0107564 | A1 | 5/2008 | Sternberg et al. |
| 2008/0132880 | A1 | 6/2008 | Buchman et al. |
| 2008/0177250 | A1 | 7/2008 | Howlett |
| 2008/0235888 | A1 | 10/2008 | Vaillancourt et al. |
| 2009/0028750 | A1* | 1/2009 | Ryan ........................ A61L 2/18 422/28 |
| 2009/0137969 | A1 | 5/2009 | Colantonio et al. |
| 2009/0205151 | A1 | 8/2009 | Fisher et al. |
| 2009/0297400 | A1 | 12/2009 | Cady et al. |
| 2010/0000040 | A1 | 1/2010 | Shaw et al. |
| 2010/0003067 | A1 | 1/2010 | Shaw et al. |
| 2010/0050351 | A1 | 3/2010 | Colantonio et al. |
| 2010/0064456 | A1 | 3/2010 | Ferlic |
| 2010/0083452 | A1 | 4/2010 | Vaillancourt et al. |
| 2010/0200017 | A1 | 8/2010 | Kerr et al. |
| 2011/0030726 | A1 | 2/2011 | Vaillancourt et al. |
| 2011/0054440 | A1 | 3/2011 | Lewis |
| 2011/0184382 | A1 | 7/2011 | Cady |
| 2011/0265825 | A1 | 11/2011 | Rogers et al. |
| 2011/0314619 | A1 | 12/2011 | Schweikert |
| 2012/0016318 | A1 | 1/2012 | Hoang et al. |
| 2012/0022469 | A1 | 1/2012 | Alpert |
| 2012/0302997 | A1 | 11/2012 | Gardner et al. |
| 2013/0164189 | A1 | 6/2013 | Hadden |
| 2013/0197485 | A1 | 8/2013 | Gardner et al. |
| 2014/0188089 | A1 | 7/2014 | Midgette et al. |
| 2014/0228773 | A1 | 8/2014 | Burkholz |
| 2014/0261558 | A1 | 9/2014 | Rogers et al. |
| 2015/0343174 | A1 | 12/2015 | Ziebol et al. |

FOREIGN PATENT DOCUMENTS

| | | |
|---|---|---|
| JP | 1284222 A | 11/1989 |
| WO | 2007044760 A2 | 4/2007 |

(56) References Cited

FOREIGN PATENT DOCUMENTS

| WO | 2007137056 | A2 | 11/2007 |
| WO | 2008089196 | A2 | 7/2008 |
| WO | 2008100950 | A2 | 8/2008 |
| WO | 2008140807 | A4 | 11/2008 |
| WO | 2009123709 | A2 | 10/2009 |

OTHER PUBLICATIONS

International Search Report and Written Opinion of international application No. PCT/US2008/076864, dated Nov. 17, 2008, 18 pp.
The Curos(TM) Port Protector. Simply Changing Infection Control Practice. Printout from http://www.iveramed.com/iv_access_ports_infection_control.html, copyright 2008, originally accessed in 2008, 1 page.
U.S. Appl. No. 13/445,207, filed Apr. 12, 2012.

* cited by examiner

STERILIZING DEVICE WITH PINCH ACTUATED CAP AND HOUSING

CROSS-REFERENCE TO RELATED APPLICATIONS

This application is a continuation of U.S. patent application Ser. No. 13/495,937, filed on Jun. 13, 2012, which is a continuation-in-part of U.S. patent application Ser. No. 12/624,154, filed on Nov. 23, 2009 and issued as U.S. Pat. No. 8,252,247, which claims the benefit of U.S. Provisional Patent Application Ser. No. 61/496,298, filed on Jun. 13, 2011; U.S. patent application Ser. No. 12/624,154 is a continuation-in-part of U.S. patent application Ser. No. 12/300,717, issued as U.S. Pat. No. 8,273,303, which is a U.S. national stage entry application of PCT Patent Application No. PCT/US2008/076864, filed on Sep. 18, 2008, which claims the benefit of U.S. Provisional Patent Application Ser. No. 61/050,769, filed on May 6, 2008, all of which are incorporated by reference herein in their entireties for all purposes.

TECHNICAL FIELD

The present invention relates to devices and methods for sterilizing medical devices. More specifically, the present invention relates to a sterilizing device including a sterilizing element configured for sterilizing the medical connection sites of luer connections, luer compatible components, catheter hubs, and other medical connections and access ports.

BACKGROUND

Mating luer connections, needleless connectors, and needle access ports serve as a conduit for administering medication to a patient by the joining of their mutual complimentary components. Prior to connecting two luer compatible components together, it is important to sterilize the connection end-sites. Typically, the connection end-sites are sterilized by wiping each site with an antiseptic wipe. Contacting and cleaning intricate details on an end-site such as cracks, crevices or grooves and where microscopic bacterium can reside on an end-site, and particularly, where an end-site has been assembled with multiple components having microscopic surfaces that can harbor bacterium (e.g. needle-less connector having assembled components such as a housing, seals, valve or septum) requires an awareness to effectively sterilize and thoroughly kill those pathogens that would otherwise make an already sick patient worse. The wiping and sterilizing of the connection end-sites must be done for a specified amount of time and accuracy to achieve a "kill of microbes" prior to the luer compatible components being connected together to reduce the risk of infection to the patient. This is also true for needle access ports or other connections. Without this simple precautionary step of sterilizing the working end-sites, patients are at a greater risk of contracting an infection.

The current method for sterilizing a connection end-site, catheter hub, needle access port, or needleless connector employs an antiseptic towelette that comes in a small foil packet and is commonly used throughout hospitals, clinics, and home healthcare. The foil packet in which the antiseptic towelette comes in must be torn open and the towelette lifted out with gloved hands. The towelette is a small folded sheet of fibrous, non-woven material that contains isopropyl alcohol. The clinician cannot adequately use the towelette to wipe the various complex surfaces, edges, threads, lumen, septum of a working end-site due to the towelette's small size and flimsy characteristics. Thus, that which should be a routine precautionary step to maintain sterility is unfortunately either ignored or not adequately performed to prevent patient infection.

SUMMARY

According to various embodiments, the present invention is a contoured, pre-moistened antipathogenic sterilizing element for wiping medical luer compatible connector end-sites, needleless connector end-sites, and/or needle access port end-sites. According to some embodiments, the sterilizing element is pre-shaped to contour to the outer and inner surfaces of the working end-site of a medical device such that it contacts the outer and inner surfaces of the working site. A wiping and/or a twisting motion is used to wipe debris from and apply a layer of an antipathogenic agent to the site. In some embodiments, the sterilizing element is contained in a flexible tubular or rectangular housing.

According to other embodiments, the present invention is a universally adaptable, contoured sterilizing element that is contained within a small ergonomic housing configured to be held in the fingers of one hand. In some embodiments, the housing may be opened by using the fingers of one hand to squeeze the lateral sides, or by forcibly pushing a site end through a sealed membrane or frangible lid to engage the contoured sterilizing element. In other embodiments, the cover can be physically removed from the top of the housing to access the contoured sterilizing element contained within the housing. In other embodiments, the sterilizing element may be left engaged with the working end-site until the end-site is ready for use.

According to some embodiments, the present invention is a sterilizing element for cleaning and sterilizing outer and inner surfaces of a working end-site of a medical device. The sterilizing element includes an antipathogenic agent. According to some embodiments, the sterilizing element may be pre-moistened or impregnated with the antipathogenic agent. According to other embodiments, the antipathogenic agent may be bonded to a surface of the sterilizing element. The sterilizing element includes a first end and a second end and a recessed portion configured to receive the working end-site of the medical device therein. Additionally, the recessed portion includes an inner surface configured to contour to and contact the outer surfaces of the working end-site of the medical device and a raised base portion configured to contact and engage the inner surfaces of the working end-site of the medical device.

According to another embodiment, the sterilizing element includes first and second ends and a recessed portion configured to inwardly receive the working end-site of the medical device. In certain embodiments, the recessed portion includes: a base portion configured to contact a distal end of the working end-site; an inner surface configured to contour and form-fit to the outer surfaces of the working end-site of the medical device; and an inner diameter that tapers down from the first end to the second end of the sterilizing element. According to some embodiments, the sterilizing element may be pre-moistened or impregnated with the antipathogenic agent. According to other embodiments, the antipathogenic agent may be bonded to a surface of the sterilizing element.

In other embodiments, a sterilizing device for wiping and sterilizing outer and inner surfaces of a working end-site of a medical device includes a housing and a sterilizing element secured and contained within the housing. In some embodiments, the housing includes at least one end adapted to be opened, and sidewalls having an outer surface. In some embodiments, the sterilizing element includes a first end, a second end, and a recessed portion configured to receive and engage the outer surfaces of the working end-site. In certain embodiments, the recessed portion includes an inner surface configured to contour to and contact the outer surfaces of the working end-site and a raised base portion configured to contact and engage the inner surfaces of the working end-site. According to some embodiments, the sterilizing element may be pre-moistened or impregnated with the antipathogenic agent. According to other embodiments, the antipathogenic agent may be bonded to a surface of the sterilizing element.

In some embodiments, the at least one end adapted to be opened includes a seal adapted to be transitioned from a closed configuration to an open configuration by the application of an inward pressure applied to the sidewalls of the housing. In other embodiments, the at least one end adapted to be opened includes a lid adapted to be removed from the housing by the application of an inward pressure applied to the sidewalls of the housing.

In certain embodiments, the housing includes an envelope of a flexible material and wherein the at least one end comprises a removable portion. In further embodiments, the housing includes an envelope of a flexible material having a lining, the lining comprising the sterilizing element according to the various embodiments of the present invention.

In some embodiments, the at least one end adapted to be opened includes a frangible lid. According to various embodiments, the frangible lid can be made of plastic, mylar, foil, laminated foil, laminate, or other similar material. In other embodiments, the at least one end adapted to be opened includes a pre-scored lid. In still other embodiments, the at least one end comprises a peel-away lid. According to further embodiments, the housing includes a protective cover secured adjacent to the at least one end adapted to be opened.

In some embodiments, the housing further includes a removable cover secured over the at least one end adapted to be opened. According to some embodiments, the removable cover includes a second sterilizing element contained and secured within the removable cover. The sterilizing element includes a first end and a second end and a recessed portion configured to receive and contact the outer surfaces of the working end-site. The recessed portion includes an inner surface configured to contour to and contact the outer surfaces of the working end-site and a raised base portion configured to contact and engage the inner surfaces of the working end-site. According to some embodiments, the sterilizing element may be pre-moistened or impregnated with the antipathogenic agent. According to other embodiments, the antipathogenic agent may be bonded to a surface of the sterilizing element.

According to some embodiments, a dual-ended sterilizing device includes an elongated housing comprising a first portion having a first end adapted to be opened and a second portion having a second end adapted to be opened, and a first sterilizing element contained and secured within the housing. The sterilizing element includes at least one end configured to inwardly receive a working end-site of a medical device therein to conform to and contact at least the outer surfaces of the working end-site. According to some embodiments, the sterilizing element may be pre-moistened or impregnated with the antipathogenic agent. According to other embodiments, the antipathogenic agent may be bonded to a surface of the sterilizing element.

According to some embodiments, the sterilizing element includes a single, continuous foam piece extending from the first end of the first portion of the housing to the second end of the second portion of the housing. The continuous foam piece generally includes a first end and a second end. Each end of the continuous foam piece is configured to inwardly receive the working end-site therein, and to contour to at least the outer surfaces of the working end-site of the medical device. According to some embodiments, the sterilizing element may be pre-moistened or impregnated with the antipathogenic agent. According to other embodiments, the antipathogenic agent may be bonded to a surface of the sterilizing element.

According to some embodiments, the dual ended sterilizing device further includes a partition separating the first portion of the housing from the second portion of the housing. The first sterilizing element is secured within the first portion of the housing. In some embodiments, the dual ended sterilizing device includes a second sterilizing element contained and secured within the second portion of the housing. According to various embodiments, the second sterilizing element includes an antipathogenic agent and at least one end configured to inwardly receive and conform to at least the outer surfaces of the working end-site. In other embodiments, a sterile drying element can be contained and secured within the second portion of the housing. The sterile drying element can be configured to inwardly receive and conform to at least the outer surfaces of the working end-site. In certain embodiments, the drying element may be left engaged with the working end-site until the site is ready for use. In still other embodiments, the dual ended sterilizing device includes a female luer connector secured to the partition and contained within the second portion of the housing. The female luer connector can be adapted to connect to any one of a male luer lock, slip luer, or thread luer connector.

According to some embodiments, a method of wiping, drying, and sterilizing a medical device including a working end-site having inner and outer surfaces includes: providing a sterilizing element comprising an antipathogenic agent, and a recessed portion having an inner surface configured to contour to the outer surfaces of the working end-site and a raised portion configured to contact and engage the inner surfaces of the working end-site; inserting the working end-site into the recessed portion of the sterilizing element to engage the working end-site therein; wiping and sterilizing the working end-site located within the recessed portion, removing the working end-site from the sterilizing element, and air-drying the working end-site for a period of time. In some embodiments, the method further includes disposing of the sterilizing element after the initial use.

In some embodiments, the method further includes forcibly engaging the working end-site through the at least one end adapted to be opened to access the sterilizing element contained within the housing. In other embodiments, the method further includes squeezing the sidewalls of the housing to transition the at least one end from a closed configuration to an open configuration to access the sterilizing element contained within the housing. In certain embodiments, the at least one end of the housing may be transitioned from a closed configuration to an open configuration using the fingers on a single hand.

In some embodiments, the method further includes compressing the sterilizing element to expel the antipathogenic agent from the sterilizing element and onto the working end-site. In some, the step of compressing the sterilizing element includes engaging the working end-site in the recessed portion of the sterilizing element. In other embodiments, the step of compressing the sterilizing element includes squeezing the sidewalls of the housing to expel the antipathogenic agent from the sterilizing element onto the working end-site.

In some embodiments, a sterilizing device for use in sterilizing the working end-site of a medical device includes a housing having a sidewall with a lower housing section and an upper housing section, and an opening configured to receive the working end-site; a sterilizing element disposed within an interior space of the housing and including an antipathogenic agent configured for sterilizing the working end-site of the device; and a cap hingedly coupled to the housing and configured to transition between an open cap position for receiving the working end-site through the opening, and a closed position adapted to hermetically seal the sterilizing element within the housing. In certain embodiments, the cap includes an annular-shaped skirt configured to contact and conformingly engage the upper section of the housing. In some embodiments, the cap includes a second sterilizing element that can be used to wipe and sterilize the working end-site of a medical device.

In some embodiments, a sterilizing element includes a plurality of cylindrically-shaped foam members coupled end-to-end to each other, forming a cylindrically shaped sterilizing element. Each foam member includes a number of inwardly-projecting members, which together form a star-shaped opening configured for sterilizing the working end-site of a medical device. In some embodiments, the inwardly projecting members for one or multiple foam members are circumferentially offset from the inwardly projecting members on an adjacent foam member, thus staggering the contact surfaces to create a detail contour opening that contacts and disinfects the working end-site. In certain embodiments, the sterilizing element can be fabricated by individually forming a number of cylindrically-shaped foam members and a repeating pattern and each including a first end, a second end, and a plurality of inwardly-projecting members defining a star-shaped opening, attaching a first end of a first foam member to an end of a contoured base member, and attaching a first end of a second foam member to the second end of the first foam member. In additional embodiments, the cylindrically-shaped members are concentric and share the same longitudinal axis but have a different internal radii and progressively taper inwardly along the longitudinal axis in a direction from top to bottom. In this way, the inner opening of the sterilizing element is wider toward the housing opening and narrows towards the contoured base. In some embodiments, the cylindrical-shaped members have adjacent members which vary in overall pattern or cross-sectional shape from member to member as well as inwardly projecting members that have dissimilar patterns. According to some embodiments, the stack members are offset from adjacent members to stagger the contact surface, and may include the base member, to maximize a detail contoured cavity.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

All medical luers and all medical device ends need to be sterilized prior to use. The term "luer" is well known in the medical field and in the art and is used here (luer hub, male luer, female luer, slip luer) to mean mating structures, with or without threads, that allows two mating luer devices, or luer compatible components, to be joined for fluid communication. The term "site," "end-site" or "site end" is used interchangeably and is used here to be understood to mean any and all working ends and/or sites including, but not limited to, a luer, luer hub (e.g. catheter hub), luer compatible component, needle access port, needleless connector, or septum. According to various embodiments, the present invention is a tool for effectively sterilizing and wiping debris from all surfaces of a working end including, but not limited to, threads, sides, edges, inner lumens, septums, and needle access ports.

Figure 1:
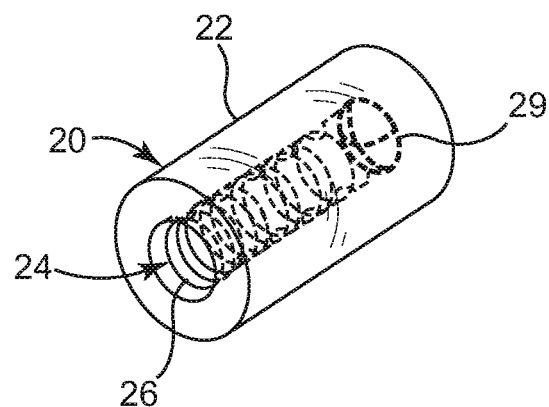
FIG. 1 is an isometric view of a contoured sterilizing element provided in accordance with an illustrative embodiment.
Figure 2A:
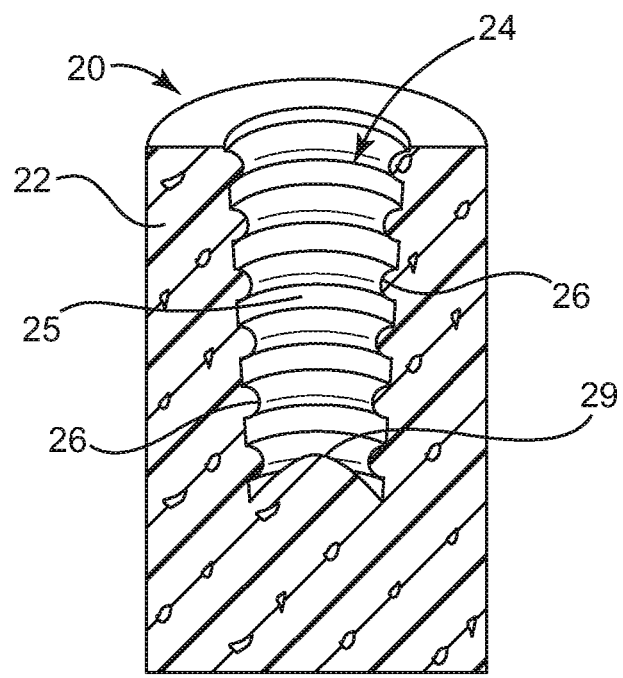
FIG. 2A-2C are cross-sectional views of a contoured sterilizing element in accordance with various embodiments.
Figure 2B:
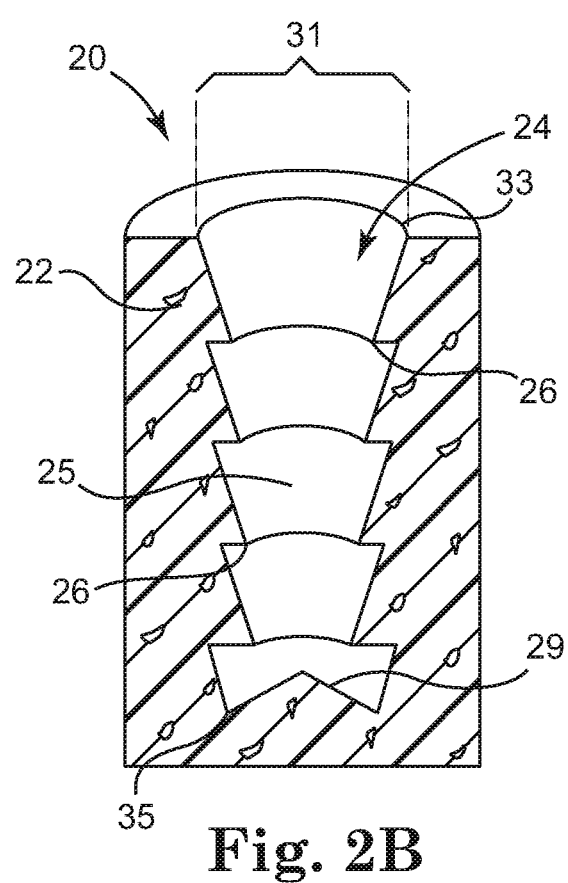
Figure 2C:
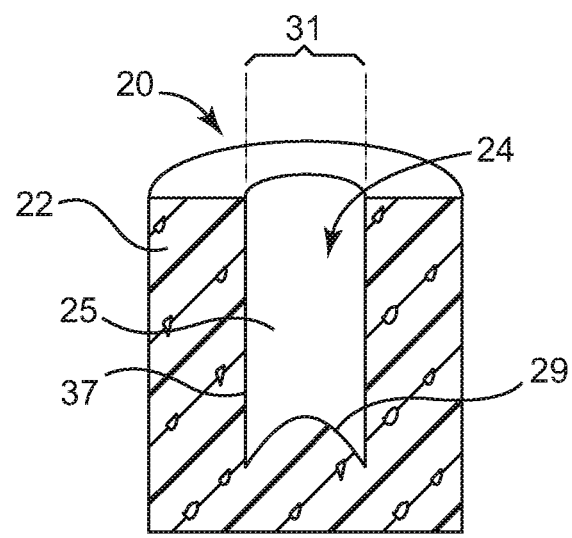

FIG. 1 is an isometric view of a contoured sterilizing element 20 provided in accordance with an illustrative embodiment. FIGS. 2A-2C are cross-sectional views of the contoured sterilizing element 20, as shown in FIG. 1, according to various embodiments. The sterilizing element 20 is configured to wipe debris from and to sterilize and/or dry a working end-site of a catheter hub, luer connector, luer component, and/or access port using a wiping, twisting, dabbing, push/pull and/or screwing motion around all of the surface aspects of the device to be sterilized. Additionally, the sterilizing element 20 is configured to apply an inclusive layer of an antipathogenic agent to the inner and outer surfaces of the working end-site. An inclusive layer, as used herein, is a layer of the antipathogenic agent applied via the contoured aspects of the sterilizing element which contacts all accessible inner and outer surfaces of the working end-site and contains an amount of the pathogenic agent sufficient to effectively sterilize the working end-site of the medical device. The contoured sterilizing element 20 is intended for a one time, single use, disposable application.

The sterilizing element 20 can be made from a variety of materials including, but not limited to, non-woven, particulate-free absorbent foams, natural or synthetic sponges, or other suitable materials, both semi-flexible or semi-rigid, known to those of skill in the art. In some embodiments, the contoured sterilizing element 20 includes an absorbent foam article 22. In other embodiments, the contoured sterilizing element 20 is formed from an absorbent, viscoelastic resilient foam or silicone rubber.

According to some embodiments, the absorbent material can be pre-shaped or pre-molded such that it is configured to contour to the surfaces of the working end to be sterilized. For example, in some embodiments, the sterilizing element 20 can be contoured and pre-shaped such that it is configured to form-fit over the working end-site of a medical connector, catheter hub, luer compatible connector, luer component, and/or needle access port for efficient wiping and sterilizing. In other embodiments, the sterilizing element 20 can be shaped to contour to and engage an inner lumen, septum, port, and/or needleless injection site. In other embodiments, a micropatterned or microtextured surface on the sterilizing element 20 provides an additional refinement to the contour sterilizing tool for contacting and cleaning intricate details on an end-site such as cracks, crevices or grooves and where microscopic bacterium can reside on an end-site, and particularly, where an end-site has been assembled with multiple components having microscopic surfaces that can harbor bacterium (e.g. needle-less connector having assembled components such as a housing, seals, valve or septum). The microtexturing or micropatterning can include any one of a number of ridges, bumps, surface roughing, rings, concentric circles, lattice features and the like. In yet other embodiments, the sterilizing element 20 is configured to engage a working end-site of a medical device such that a friction fit is created between the sterilizing element 20 and the end-site of the medical device. The sterilizing element 20 can remain frictionally engaged with the working end-site until ready for use. According to another embodiment, the absorbent foam material is sufficiently resilient such that it conforms to the surfaces of the working end-site when the working end-site is depressed into the absorbent material.

According to various embodiments, the absorbent material includes an antipathogenic agent including any one of an antiseptic, disinfectant, microbiocidal, or combinations thereof to kill pathogens on the surfaces of the device. According to one embodiment, an antipathogenic agent is a dry agent bonded to the surfaces of the sterilizing element. According to another embodiment, the sterilizing element is impregnated with an antipathogenic agent. For example, the sterilizing element may be impregnated with an oligodynamic metal. An oligodynamic metal is a metal shown to have anti-bacterial properties even in minute quantities. Exemplary oligodynamic metals include, but are not limited to, the following: gold, zinc, copper, and cerium. According to one embodiment, the sterilizing element may be impregnated with silver. In other embodiments, the absorbent material is pre-moistened with at least one antipathogenic agent. Exemplary antipathogenic agents include, but are not limited to, the following: isopropyl alcohol, povidone iodine, chlorhexidine gluconate, and other useful antipathogenic agents known to those of skill in the art. Additionally, depending on the antipathogenic agent used, a sufficient amount of antipathogenic agent can be incorporated into the absorbent material to achieve an acceptable ratio of "antipathogenic agent to dry-time," wherein a sufficient amount of antipathogenic agent is used to adequately disinfect the site end while at the same time achieving a fast drying rate. The connector devices should be sterile, dry, and free of antipathogenic residue or provide a residue that would be non-toxic and compatible to both the patient and the end-site material since they complete the pathway of medication into the patient's body prior to their connection. According to one embodiment, the drying rate after the antipathogenic agent has been applied to the working end-site is less than about 15 seconds. In other embodiments, the drying rate is less than about 10 seconds. In still other embodiments, the drying rate is less than about 7 seconds.

In some embodiments, the working end-site undergoes a visual change in appearance when contacted with the antipathogenic agent contained within the sterilizing element 20. For example, in some embodiments, the sterilizing element 20 releases the antipathogenic agent upon contact with the working end-site of the medical device, wetting the surface with the antipathogenic agent and causing a visual change in the end-site due to a microtextured microporous (e.g., a polymeric porous permeable polymer), micropatterned, bonded or solvatochromic dyed surface (e.g., merocyanine dye or Reichardt's dye) of the end-site. Exemplary surfaces of a working end-site adapted to undergo a visual change upon contact with an antipathogenic agent or other change initiating reactant are generally shown and described in U.S. Published Application No. 2008/0021381, entitled "Medical Fluid Access Device with Antiseptic Indicator," the entirety of which is incorporated by reference herein for all purposes. As a result of contact with the antipathogenic agent, the working end-site can visually change from a first state to a second state such as, for example, from visually light to visually dark or from a dark surface to a light surface over time due to exposure to the antipathogenic agent or from a wetted surface to a dry surface.

In other embodiments, the sterilizing element 20 itself can be adapted to undergo a visual change. For example, the sterilizing element 20 is impregnated with an antipathogenic agent such as IPA (isopropyl alcohol) and can visually change from a darker appearance when contact is first made with the working end-site to a lighter appearance as when the sterilizing element 20 is left in place on the working end-site and the antipathogenic agent dries and/or evaporates. In some embodiments, the sterilizing element 20 can include a micropatterned (e.g., fine lines, cracks), microporous or microtextured surface, such as described above, that is adapted to undergo the visual change.

In yet another embodiment, the sterilizing element 20 is impregnated with a visual change reactant that when applied to working end-site indicates that the end-site has been contacted with the antipathogenic agent and sterilized. In some embodiments, the visual change reactant can undergo a transition to indicate that the working-end site dried. Exemplary visual change reactants can include a number of dyes suitable for this purpose known to those of skill in the art. In some embodiments, the visual change observed on either the surface of the working end-site or the sterilizing element 20 itself, as described above, can be a visual color change.

In further embodiments, the sterilizing element 20 can be translucent or even transparent such that a visual change in the working end-site or even the sterilizing element 20 can be easily and readily observed by the user through the sterilizing element 20 to the end-site. For example, in one embodiment a the translucent/transparent sterilizing element 20 including a microtextured, micropatterned or microporous surface, such as described above, provides the clinician with a view of refraction that occurs when the wetted, resilient surface of the sterilizing element 20 contacts the harder, more rigid surfaces of the end-site causing a visual change to occur from a darker appearance when contact is first made to a lighter appearance following the removal of the sterilizing element 20 and the end-site allowed to dry.

FIGS. 2A-2B are cross-sectional views of a sterilizing element 20, according to various embodiments. According to some embodiments, the contoured sterilizing element includes an absorbent foam piece 22 having a recessed portion 24 including an inner surface 25 configured for receiving the working end-site of a medical device to be sterilized therein. According to one embodiment, the recessed portion 25 is configured such that the working end-site can be inserted to a depth of approximately 10 mm. In other embodiments, the recessed portion 25 is configured such that the working end-site can be inserted into the recessed portion 25 by a depth of about 5 mm to about 7 mm. In yet another embodiment, the working end-site may be inserted into the recessed portion 25 by a depth of about 3 mm.

As shown in FIGS. 2A and 2B, the recessed portion 24 can include a plurality of raised structures 26 formed on the inner surface 25 of the recessed portion 24. The raised structures 26 project into the recessed portion, and are configured to engage the threads, sides, and/or edges on the working end-site. In some embodiments, the raised structures 26 can include ridges, flanges, and/or threads, as shown in FIG. 2A, steps as shown in FIG. 2B, or combinations thereof. According to a further embodiment, as shown in FIG. 2B, the raised structures 26 provided on the inner surface 25 of the recessed portion 24 provide an inner diameter 31 that tapers down from a first end 33 to a second end 35 of the sterilizing element 20. These raised structures 26 located on the inner surface 25 of the recessed portion or cavity 24 of the sterilizing element 20 facilitate the effective sterilization of all surfaces of the working end-site of a first connection device prior to the attachment with a complimentary second connection device.

Additionally, in some embodiments the recessed portion 24 can include a raised base portion 29 configured to project into and engage the inner luer lumen and/or septum of a needleless connector or port end. The raised base portion can have a number of configurations. For example, the raised base portion 29 can be configured as any one of a nipple, bump, nub, tine, or other similar projection.

FIG. 2C is a cross-sectional view of a sterilizing element 20 according to another illustrative embodiment. As shown in FIG. 2C the sterilizing element 20 includes a generally, cylindrical absorbent foam piece 22 having a recessed portion 24. The cylindrical foam piece 22 can be contoured and shaped so that it "form-fits" over the working end-site of a luer compatible connector, medical device connector component, and/or needle access port for efficient wiping and sterilizing. In one embodiment, as shown in FIG. 2C, the recessed portion 24 has an inner diameter 31 less than an outer diameter of the working end-site to be sterilized such that when a working end-site is received in the recessed portion 24 the inner walls 37 of the recessed portion conform to the outer surfaces of the working ends site. In some embodiments, the sterilizing element 20 may include a raised base portion 29 configured to project into and engage the surfaces of an inner lumen or septum, as described above.

Figure 3:
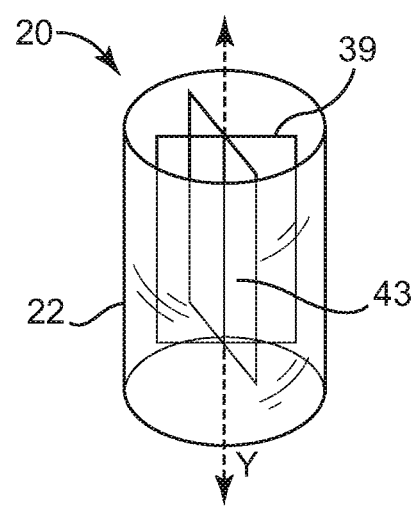
FIG. 3 is an isometric view of a sterilizing element according to another illustrative embodiment.

FIG. 3 is an isometric view of a sterilizing element 20 according to another illustrative embodiment. The sterilizing element 20 is made from a foam or sponge-like material and is die cut to conform to the surfaces of the working end-site to be sterilized. The die cut sterilizing element 20 can be cut in a number of configurations, such that it conforms to a variety of medical device connectors, components, and access ports. Additionally, according to some embodiments, the die cut sterilizing element 20 can be cut such that it is especially configured to accommodate a device having a lumen or septum. For example, the die cut sterilizing element 20 may be cut such that it is configured to project into and engage the inner surfaces of the a medical device having an inner lumen and/or a septum. In one embodiment, as shown in FIG. 3, the sterilizing element 20 includes an absorbent foam piece 22 that is die-cut to include at least one slit 39 formed along a longitudinal axis Y of the element 20 such that when a working end-site is depressed into the sterilizing element 20, the slit 39 opens to receive the working end-site therein. The slit 39 includes side walls 43 configured to conform to the surfaces of the working end-site to be sterilized.

Figure 4:
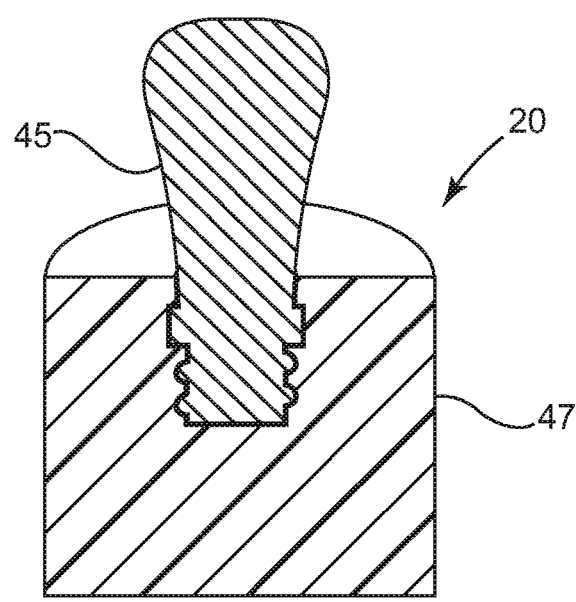
FIG. 4 is a cross-sectional view of a contoured sterilizing element engaged with a thread luer connector.

FIG. 4 is a cross-sectional view of a sterilizing element 20 according to another illustrative embodiment showing the working end-site 45 of a device to be sterilized inserted into the sterilizing element 20. As shown in FIG. 4, the sterilizing element 20 includes an absorbent, resilient article 47. In one embodiment, the absorbent resilient article 47 is fabricated from a viscoelastic foam (e.g., viscoelastic polyurethane foam). The absorbent, resilient article 47 has sufficient resiliency such that when the working end-site 45 is pressed into the resilient article 47, the resilient article 47 depresses to receive the working end-site 45 to a depth sufficient for the effective wiping and sterilization of the working end-site 45. Additionally, when the working end-site 45 is pressed into the resilient article 47 to a sufficient depth, the depressed resilient article 47 conforms to the outer surfaces of the working end-site 45.

The sterilizing element 20, according to the various embodiments, described above may be formed using a variety of techniques. According to one embodiment, the sterilizing element 20 may be heat-set, molded, pressure-molded, injection-molded, cored, laser, and/or die cut. Other techniques known to those of skill in the art for forming and shaping foam may also be used.

Figure 5A:
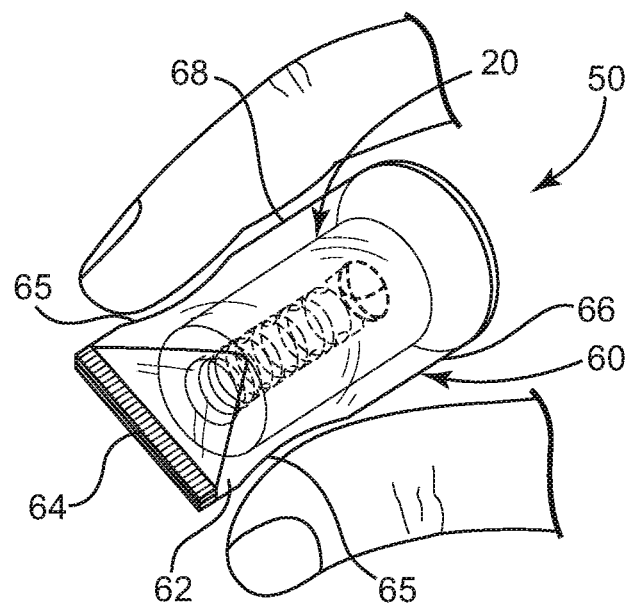
FIGS. 5A and 5B are isometric views of a sterilizing device according to one illustrative embodiment.
Figure 5B:
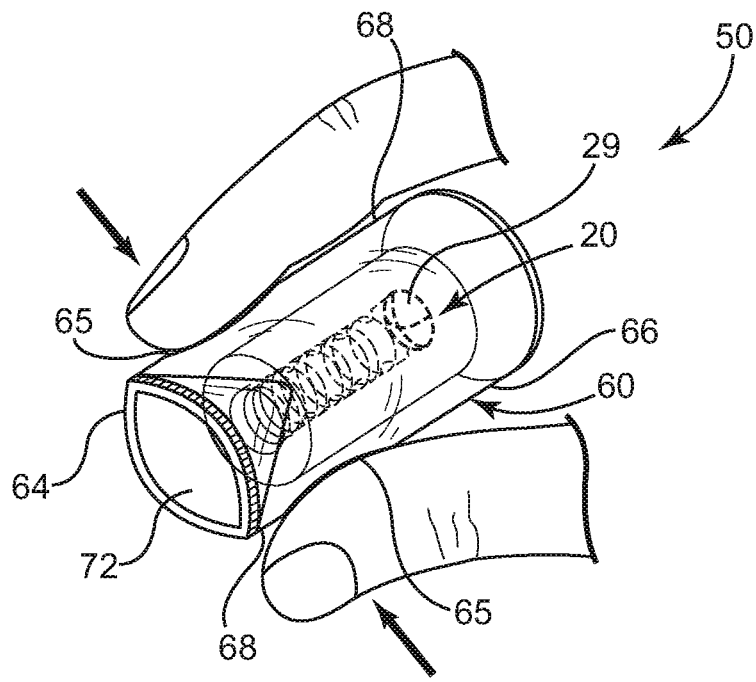

FIGS. 5A and 5B are isometric views of a sterilizing device 50 according to an illustrative embodiment. As shown in FIGS. 5A and 5B, the sterilizing device 50 includes a sterilizing element 20, such as described above, according to the various embodiments, contained within a housing 60. According to some embodiments, the sterilizing element 20 is contained within the housing 60 such that the housing 60 provides a barrier to direct contact with the sterilizing element 20 when the sterilizing element 20 is in use, and serves as a tool for mechanically manipulating the sterilizing element 20. According to various embodiments, as will be described in further detail below, the housing 60 can include a top or lid to seal and protect the pre-moistened sterilizing element from drying out within the housing until it is ready for use.

The sterilizing element 20 is secured within the housing 60 to prevent dislodgement of the sterilizing element 20 from the working end-site of the device being sterilized. The sterilizing element 20 should be sufficiently secured within the housing 60 such that it can withstand vigorous wiping of an end-site. The sterilizing element 20 can be secured within the housing by various methods including, but not limited to, the following: ultrasonic welding, inward indentations of the walls, internal molded ribs or points, adhesives, frictional engagement, as well as the sterilizing element's own outward expanding radial force to hold it in place within the housing.

According to other embodiments, the sterilizing element 20 may be removed from the housing/packaging for attachment to and sterilizing of the end-site, as well as be directly held by and in the hand of the user to sterilize the end-site. The sterilizing element 20 has an inclusive layer of antipathogenic to sterilize both the working end-site and the user's fingers. Alternatively, the contoured sterilizing element 20 may be left in place within the housing and the whole device can be left on the end-site for the purpose of protecting the site's sterility until such time the device is removed so that the site end can be used.

According to various embodiments, the housing 60 is small and ergonomically shaped so as to be easily held within the fingers of one hand of the user. In certain embodiments, the housing 60 is configured to be opened single handedly using the fingers on one hand. Additionally, the housing 60 can have a general shape such as an hourglass or flared shape that guides the placement of a user's fingers. According to other embodiments, the housing 60 can include one or more finger locating features 65 formed with sidewalls 66 and 68 of the housing 60 to guide a user's placement of their fingers when using the device 50. The finger locating features 65 may also facilitate gripping and handling of the device by the user. According to various embodiments, the finger locating features 65 can include but are not limited to be dimples, bumps, grip marks, and other features useful for locating a user's fingers. As shown in FIGS. 5A and 5B the finger locating features 65 include recesses formed in the sidewalls 66 and 68 of the housing 60. According to some embodiments, the housing 60 can be opened using the fingers on a single hand.

The housing 60 is sized to receive the working end-site of a medical connection inserted therein. The medical device or working end-site is inserted into the housing to access the sterilizing element 20 contained therein. According to one embodiment, the housing 60 is configured such that the working end-site can be inserted to a depth of approximately 5 mm. In other embodiments, the housing 60 is configured such that the working end-site can be inserted into the housing 60 by a depth of about 3 mm to about 5 mm. In yet another embodiment, the working end-site may be inserted into the housing by a depth of about 4 mm.

The housing 60 can be made from a variety of materials. According to some embodiments, the housing 60 is made from a plastic, laminated paper/foil combination, or other semi-rigid material or semi-flexible material. As shown in FIG. 5A, a top portion 62 of the housing 60 can be pinched closed to form a seal 64. The seal 64 may be formed using ultrasonic welding, heat thinning and/or a liquid impermeable polyolefin film forming a combination molded seam and parting seal. As shown in FIG. 5B, the user squeezes the sidewalls 66 and 68 of the housing 60 inward with the fingers of one hand such that the seal 64 formed along the top portion 62 opens to form opening 72. The opening 72 is sized to receive the working end-site of a connection device or other medical device therein. In some embodiments, the squeezing action causes an audible "popping sound" as the seal 64 is forced open. Opening the seal 64 exposes the sterilizing element 20 secured within the housing 60 and allows for receipt therein of the working end-site of the connection device or other medical device to be sterilized.

Figure 6:
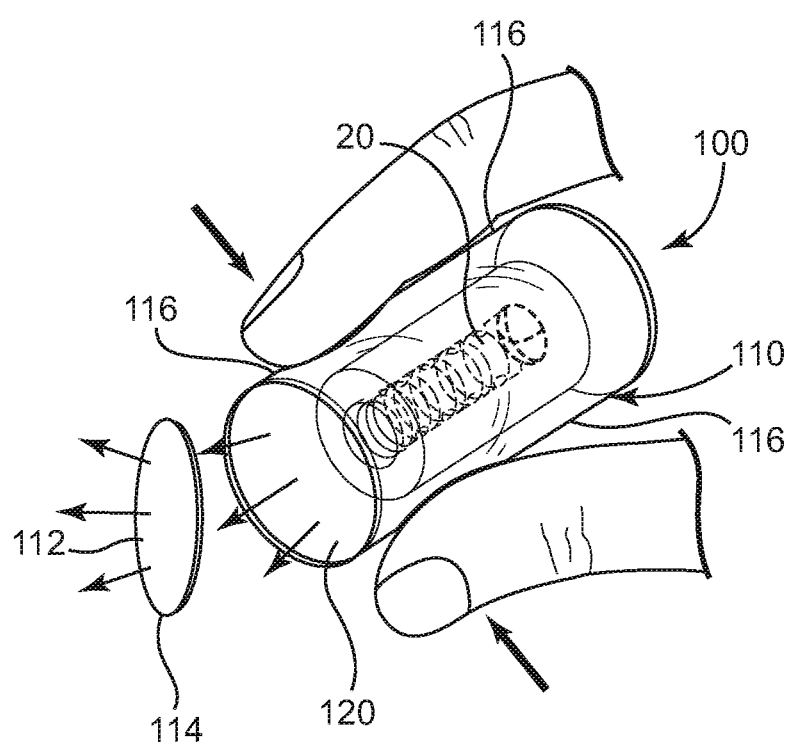
FIG. 6 is an isometric view of a sterilizing device according to another illustrative embodiment.

FIG. 6 is an isometric view of a sterilizing device 100 including a pre-moistened sterilizing element 20 contained within a housing 110 according to another illustrative embodiment. The sterilizing element 20 can have any configuration according to the various embodiments, as described above. As shown in FIG. 6, the housing 110 shows a frangible top 112 that can be sealed onto the housing 110 utilizing a combined molded seam and parting seal 114. The top 112 is secured to the housing 110 such that when the user squeezes the sidewalls 116 of the housing 110 with the fingers of one hand, the seal along the top 114 releases due to an increase in internal pneumatic pressure causing the top 112 to pop off and detach from the housing 110 to create an opening 120 facilitating access to the sterilizing element 20 contained inside.

Figure 7A:
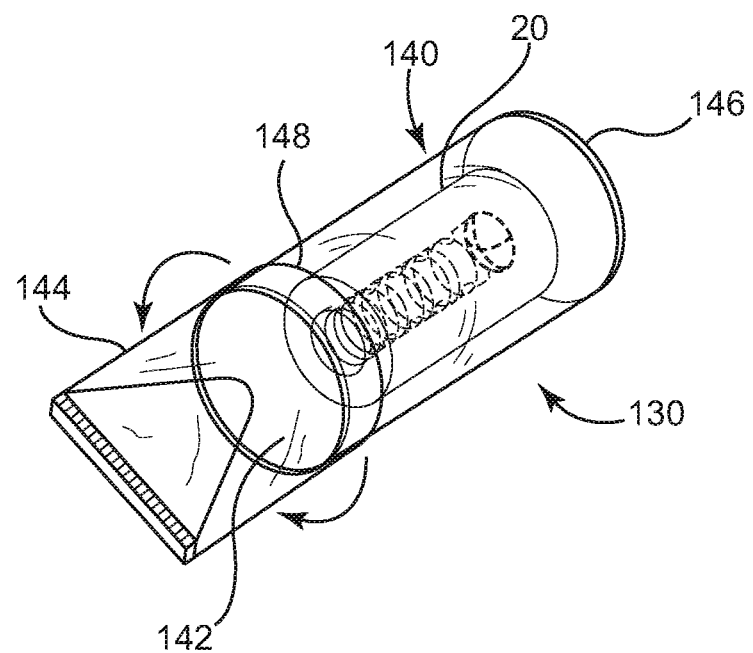
FIG. 7A is an isometric view of a sterilizing device including a housing having a removable cover according to another illustrative embodiment.
Figure 7B:
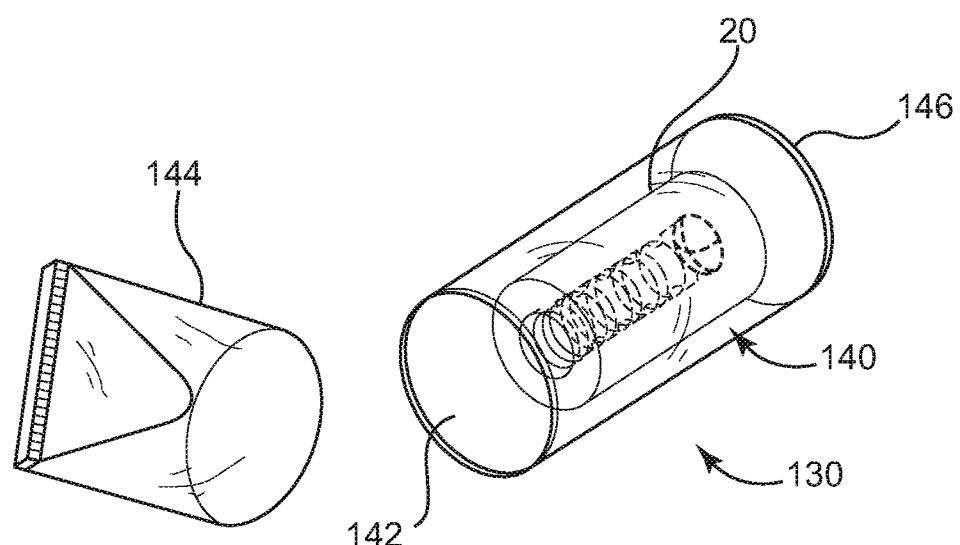
FIG. 7B is an isometric view of the sterilizing device shown in FIG. 7A, wherein the housing cover is removed.

FIGS. 7A and 7B are isometric views of a sterilizing device 130 according to another illustrative embodiment. The sterilizing device 130 includes a pre-moistened sterilizing element 20 contained within a housing 140 having an opening 142, sized to receive the working end-site of a medical device. The sterilizing element 20 can have any configuration according to the various embodiments, as described above. The housing 140 includes a removable cover 144. As shown in FIG. 7A, the removable cover 144 can be secured to the housing 140 via a circumferential frangible tear line 148. As shown in FIG. 7B, the cover 144 can be removed using a twisting and pulling motion to detach the cover 144 from the housing 140 via the tear line 148. In some embodiments, the cover 144 and the body 140 can be made of plastic, mylar, foil, laminated foil, or other flexible material. In other embodiments, the cover 144 can be made of a semi-flexible or semi-rigid material.

Figure 8:
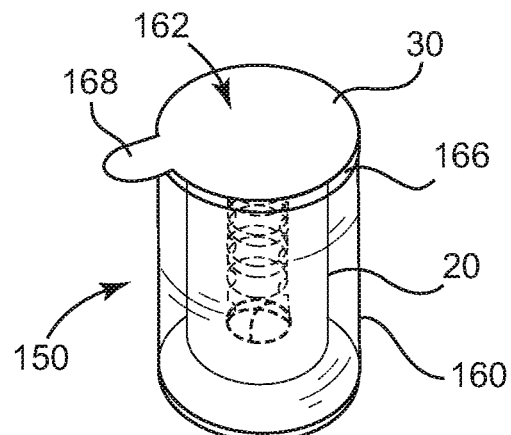
FIG. 8 is an isometric view of a sterilizing device including a housing having a removable lid provided in accordance with an illustrative embodiment.
Figure 9:
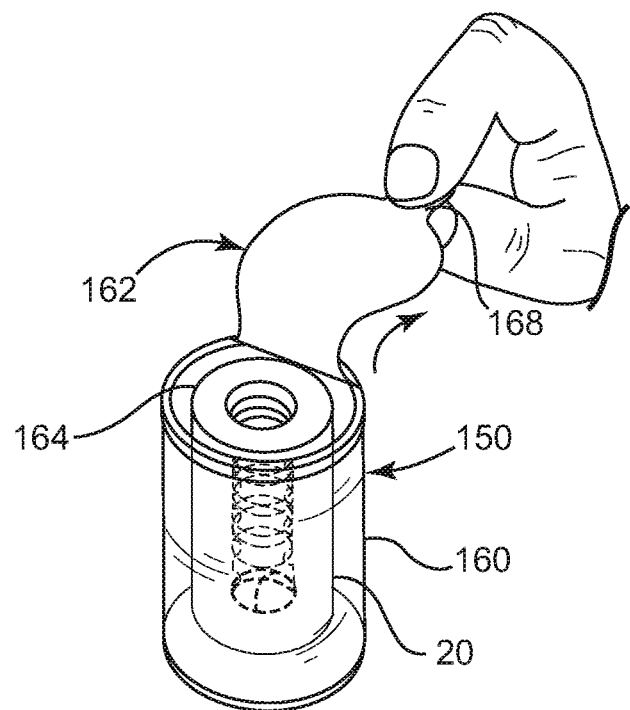
FIG. 9 is an isometric view of the sterilizing device shown in FIG. 8, wherein the lid is removed.

FIGS. 8 and 9 are isometric views of a sterilizing device 150 including a pre-moistened sterilizing element 20 contained within a housing 160 having a removable cover 162 according to another illustrative embodiment. The sterilizing element 20 can have any configuration according to the various embodiments, as described above. According to one embodiment, the removable cover 162 is a peel-away lid. As shown best shown in FIG. 8, the cover 162 is secured over the top opening 164 of the housing 160 such that it seals the pre-moistened sterilizing element 20 within. The cover 162 includes a circumferential tear line 166 for facilitating its removal. Additionally, the cover 162 can also include a tab or tether 168. According to one embodiment, as shown in FIG. 9, a user manually grasps the tab or tether 168 and pulls the cover 162 from the housing via the tear line 166 to reveal the opening 164 and grant access to the sterilizing element 20 contained within.

Figure 10:
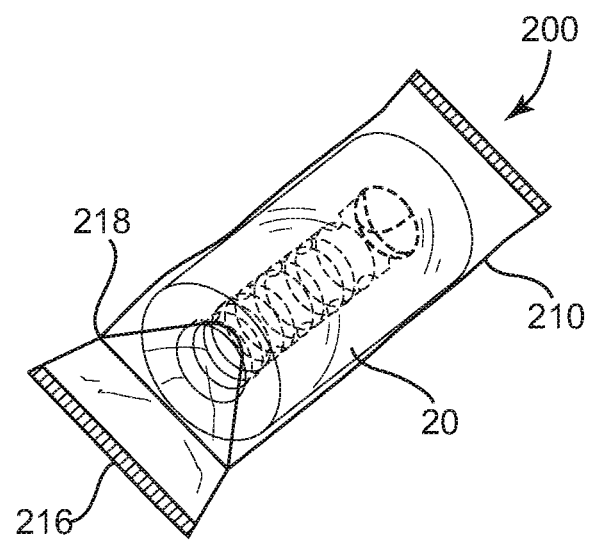
FIG. 10 is an isometric view of a sterilizing device including a housing having a tear off end provided in accordance with an illustrative embodiment.
Figure 11:
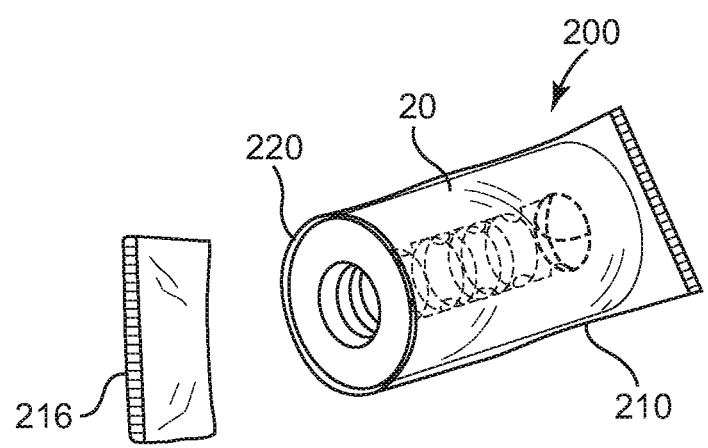
FIG. 11 is an isometric view of the sterilizing device shown in FIG. 10, wherein the end is removed.

FIGS. 10 and 11 are isometric views of a sterilizing device 200 including a pre-moistened sterilizing element 20 contained within a flexible envelope housing 210 according to yet another embodiment. The sterilizing element 20 can have any configuration according to the various embodiments, as described herein. The flexible envelope housing 210 may be formed from plastic, mylar, foil, laminated, or other flexible material. According to a further embodiment, the flexible envelope housing 210 may include a foil lining to further maintain the moisture level of the sterilizing element contained within. As shown in FIGS. 10 and 11, the flexible envelope housing 210 includes a removable protective cover 216. The removable protective cover 216 can include a line of perforations or weakness 218 configured to facilitate removal of the protective cover 216 from the housing 210. The removable protective cover 216 may be removed from the housing by tearing or cutting along the line 218. FIG. 11 shows the protective cover 216 removed from the housing 210 to create an opening 220 facilitating access to the sterilizing element 20 contained within.

Figure 12:
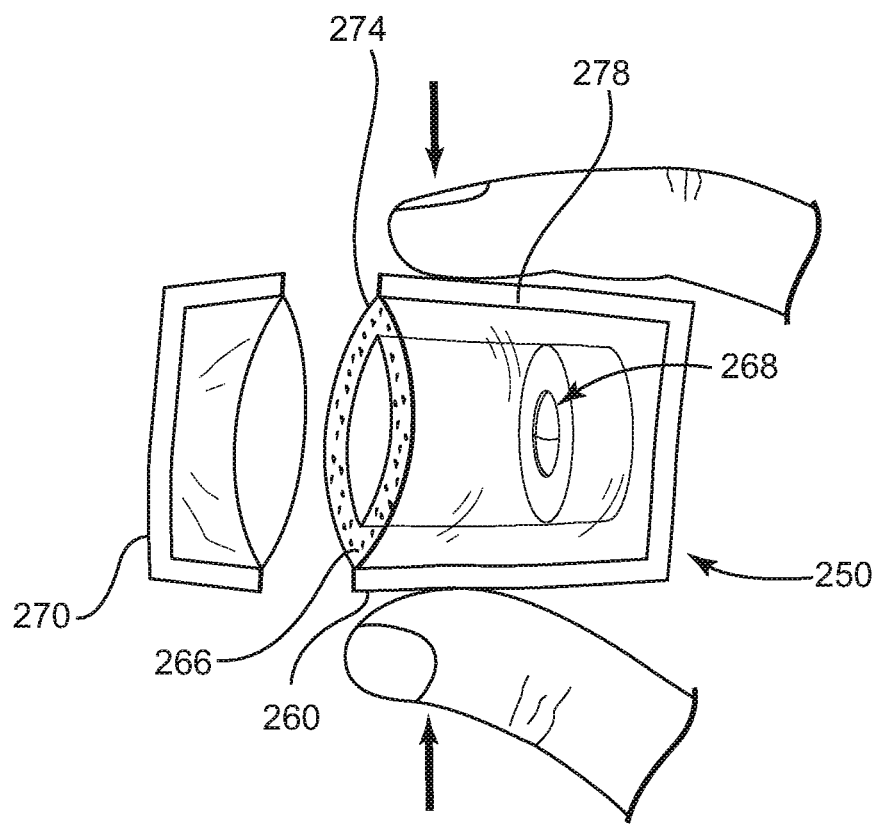
FIG. 12 is an isometric view of a sterilizing device according to another illustrative embodiment.

FIG. 12 is an isometric view of sterilizing device 250 according to another illustrative embodiment. The sterilizing device 250 includes a flexible envelope housing 260 including an inner lining 266 and a removable protective cover 270. In some embodiments, the removable protective cover 270 can be removed from the housing 260 by tearing or cutting along a perforation line or other similar line of weakness. The protective cover 270 is shown removed from the housing 260 in FIG. 12.

The inner lining 266 can be made of a particulate free absorbent foam or sponge-like material. The absorbent foam or sponge-like material is pre-moistened with an antipathogenic agent, as previously described above and lines the inner walls of the envelope housing 260. The inner foam lining 266 is contoured and can include a plurality of raised ridges, ribs or threads configured to engage the threads, sides, and/or edges on the working end-site. Additionally, as shown in FIG. 12, the inner foam lining 266 includes a raised base 268 configured to project into and to engage the inner luer lumen and/or septum of a needleless connector or port end. Additionally, according to a further embodiment, the inner lining 266 can include a reinforced oval rim 274. The reinforced oval rim 274 is adapted to flex from a closed position to an open position by squeezing the sides 278 of the flexible envelope housing 260 upon removal of the protective cover 270. The rim 274 is flexed open to facilitate the reception of a working end-site of a device to be sterilized within the inner lining 266 of the envelope 260.

Figure 13A:
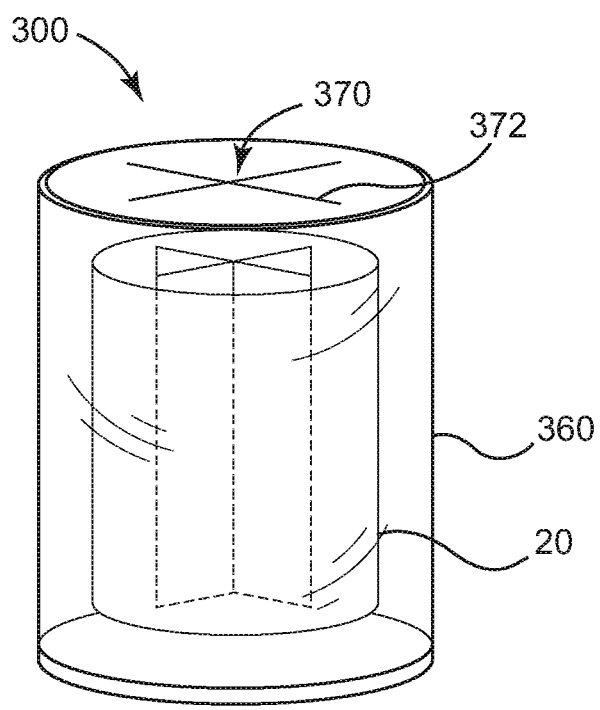
FIG. 13A is an isometric view of a sterilizing device including a frangible top according to an illustrative embodiment.
Figure 13B:
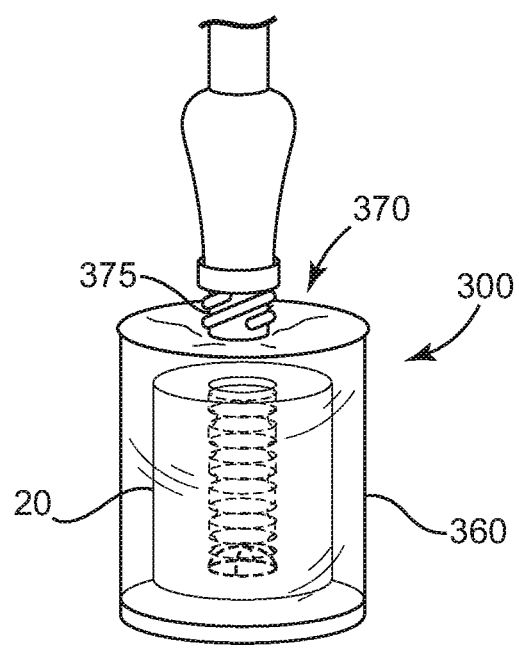
FIG. 13B is an isometric view of a working end-site forcibly engaged through the frangible top of a sterilizing device.

FIG. 13A is an isometric view of a sterilizing device 300 including a sterilizing element 20 contained within a generally cylindrical housing 360. The sterilizing element 20 can have any configuration according to the various embodiments, as described above. According to one embodiment, the housing 360 includes a frangible lid 370. The lid 370 seals the pre-moistened sterilizing element 20 and maintains a moisture rich environment inside the housing 360. According to various embodiments, the frangible lid 370 can be made of plastic, mylar, foil, laminated foil, laminate, or other similar material. In some embodiments, the frangible lid may include score-marks 372 to facilitate breaking of the frangible lid 370. The frangible lid 370 should be of sufficient thickness and frangibility, that the working end-site 375 (as shown in FIG. 13B) of a device to be sterilized, can penetrate the lid by forcibly engaging the working end-site through the pre-scored lid to access the sterilizing element 20 contained within the housing 360. FIG. 13B shows a working end-site of a device to be sterilized forcibly engaged through the frangible top 370 of the sterilizing device 300.

In some embodiments, the housing 360 is sized to facilitate prolapse of the frangible lid 370 into the housing 360. For example, as the working end-site 375 is being forcibly engaged through the frangible lid 370, the lid material pushes inward and down into the housing 360 such that the working end-site 375 can access and engage the sterilizing element 20 contained within the housing 360. In some embodiments, the working end-site 375 can be left engaged with the sterilizing element 20 contained within the housing 360 until the end-site 375 is ready for use. Together with the lid 370, the housing 360 and the sterilizing element 20 have sufficient integrity and durability such that the device 300 resists removal of the end-site 375 from the device 300 thus allowing the device 300 to be left engaged with the end-site 375 without the potential for inadvertent disengagement from the device 300. According to one embodiment, the housing 360 provides a depth of less than about 10 mm to facilitate prolapse of the lid 370 into the housing 360. In another embodiment, the housing 360 provides a depth of about 5 mm to about 10 mm, of about 3 to about 5 mm, and/or about 4 mm to facilitate prolapse of the lid 370 into the housing 360.

Figure 14:
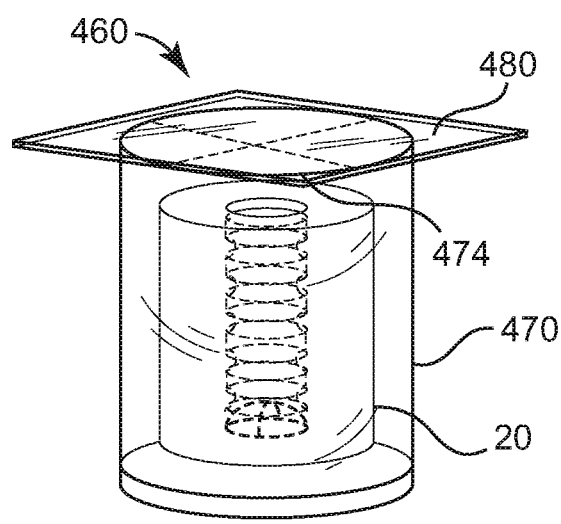
FIG. 14 is an isometric view of a sterilizing device including a protective cover according to other embodiments.

FIG. 14 shows a sterilizing device 460 according to a further embodiment. As shown in FIG. 14, the sterilizing device 460 includes a pre-moistened sterilizing element 20 according to the various embodiments as described above, contained within a housing 470 having a lid 474 and an additional debris protective covering 480. The lid 474 is secured to the top of the housing 470 to seal the pre-moistened sterilizing element 20 within the housing. According to one embodiment, as previously described above, the lid 474 is a foil or plastic frangible lid and may be pre-scored to include score-marks. Additionally, the lid 474 is of sufficient thickness and frangibility such that a working end-site of a device to be sterilized can be forced through the lid 474 to access the sterilizing element 20 contained within the housing 470.

The debris protective covering 480 is positioned adjacent and secured to the lid 474. The debris protective covering assists in keeping the device lid 474 free of debris until the device is ready for use. The debris protective covering 480 extends outward beyond an outer diameter of the housing 470. This configuration helps to stabilize the device 460 and may prevent it from rolling when the device 460 is placed on its side. Additionally, the configuration may provide a wider, sturdier base for the device 460, if the device is placed top-side-down on a flat surface. The debris protective covering 480, as shown in FIG. 14, can be used in conjunction within a variety of housing configurations, such as those described above.

Figures 15, 16:
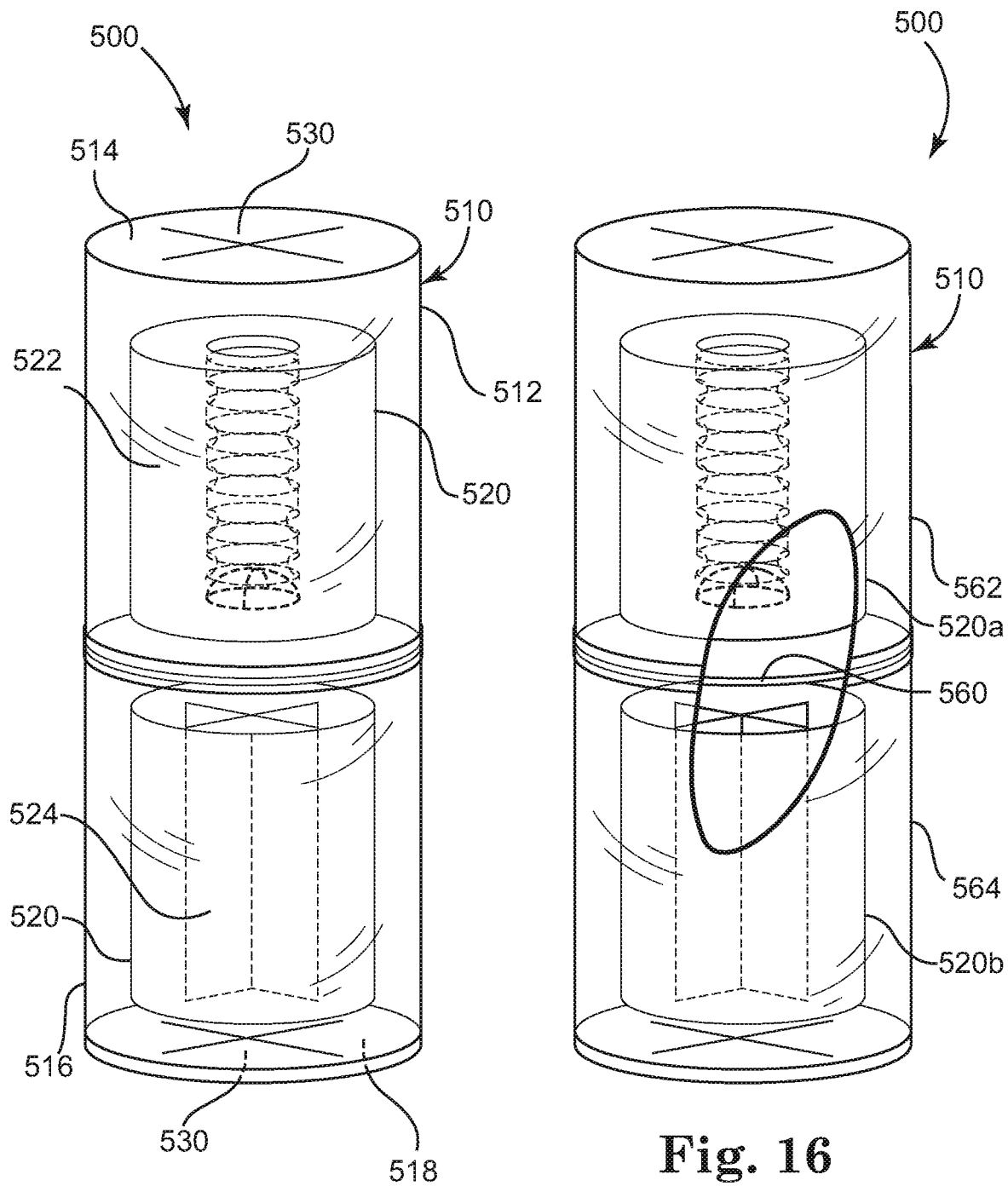
FIG. 15 is an isometric view of a dual sided sterilizing device according to another illustrative embodiment.
FIG. 16 is an isometric view of a dual sided sterilizing device according to yet another illustrative embodiment.

FIG. 15 is an isometric view of a dual sided sterilizing device 500 according to another illustrative embodiment. As shown in FIG. 15 the dual sided sterilizing device 500 includes an elongated ergonomic housing 510, having a first end 512 including a first opening 514 and a second end 516 including a second opening 518. At least one sterilizing element 520 is located within the housing 510 and can be accessed through either the first or second opening 514 or 518.

According to one embodiment, the housing 510 includes a seal or lid 530 located over each of the first and second openings 514 and 518. The lid or seal 530 can have any one of the configurations as described above. According to one embodiment, as shown in FIG. 15, the lid 530 can be a pre-scored lid. According to further embodiments each of the first and second ends 512 and 516 can include a plastic, foil, or laminated lid 530 that is of sufficient thickness and frangibility that a working end-site of a device to be sterilized can be forced through the lid to gain access to the sterilizing element contained inside. In some embodiments, a protective covering, such as described above with reference to FIG. 14, may be secured to the lid 530.

According to various embodiments, the dual sterilizing element 520 contained within the housing 510 can be made from a non-woven, particulate free absorbent foam, or sponge-like material. The absorbent foam or sponge-like material is pre-moistened with an antipathogenic agent including any one of an antiseptic, disinfectant, microbiocidal, or combinations thereof to kill pathogens on the surfaces of the device. Additionally, the sterilizing element 520 is contoured and shaped so that it "form-fits" over the working end-site of a luer compatible connector, device, and/or needle access port for efficient wiping and sterilizing. According to one embodiment, the sterilizing element 520 can extend continuously from the first end 512 to the second end 516 throughout the entire housing length 510. According to another embodiment, described in further detail below, the sterilizing element 520 can include two separate portions contained within the housing 510.

Like the housing 510, the dual sterilizing element 500 includes a first end 522 and a second end 524. Each end 522 and 524 can be shaped to fit to the various male, female (inner lumen), slip luer, septum, port, or threaded configurations of a working end-site to be sterilized, and apply an inclusive layer of an antipathogenic agent to sterilize and wipe debris from the site while using a wiping and twisting motion. According to one embodiment, each end 522 and 524 can have the same contouring. According to another embodiment, the first end 522 and the second end 524 can have different contouring. For example, the first end 522 can be contoured such that it contacts and engages the surfaces of a male connection component (e.g. male luer lock or a slip luer) and the second end 524 can be contoured such that it projects into and engages the surfaces of various female (inner lumens) and/or septums (e.g. a needleless injection port).

According to further embodiments, each of the first and second ends 514 and 518 can include a label (not shown) located on an outer surface of the housing 510. The label can be embossed or printed with differentiating numbers, letters, or symbols to assist the clinician in identifying which end of the housing they are using. Using labels to identify the working ends 514 and 518 is useful, for example, when the first and second ends 522 and 524 of the sterilizing element 520 differ so as to be used to clean and sterilize different medical devices. Additionally, labels to identify the working ends 514 and 518 of the device 500 are also useful when the antipathogenic agents on the first and second ends 522 and 524 of the sterilizing element 520 differ such that the antipathogenic agent can be selected depending on the material to be sterilized. In certain embodiments, when the sterilizing device 500 is left engaged with the working end-site after it has been cleaned and sterilized, a label can be used to signify to the user or users that the connection has been sterilized and is ready for use.

FIG. 16 is a schematic view of the dual sided sterilizing device 500 shown in FIG. 15 according to another illustrative embodiment. According to one embodiment, as shown in FIG. 16, a divider or partition 560 separates the device into two distinct portions 562 and 564. According to this embodiment, each of the portions 562 and 564 contain a separate sterilizing element 520a or 520b. The sterilizing elements 520a and 520b are secured to the divider in a back-to-back arrangement. The sterilizing elements 520a and 520b can have the same or different contour configurations. For example sterilizing element 520a can be configured to engage male luer connections and sterilizing element 520b can be configured to engage female luer connections and/or septums. Additionally, the sterilizing elements 520a and 520b can be pre-moistened with the same or different antipathogenic agent. According to yet another embodiment, the second sterilizing element 520b can be dry and can be used to dry the working end-site after the working end-site has been cleaned and sterilized using the first pre-moistened sterilizing element 520a. The second portion 564 containing the dry sterilizing element can be left engaged with the working end-site until the end-site is ready for use.

Figure 17:
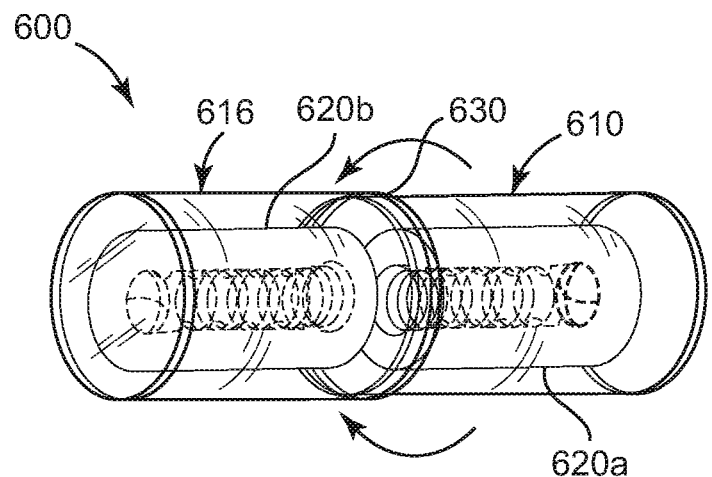
FIGS. 17 and 18 are isometric views of a combined sterilizing device according to another illustrative embodiment.
Figure 18:
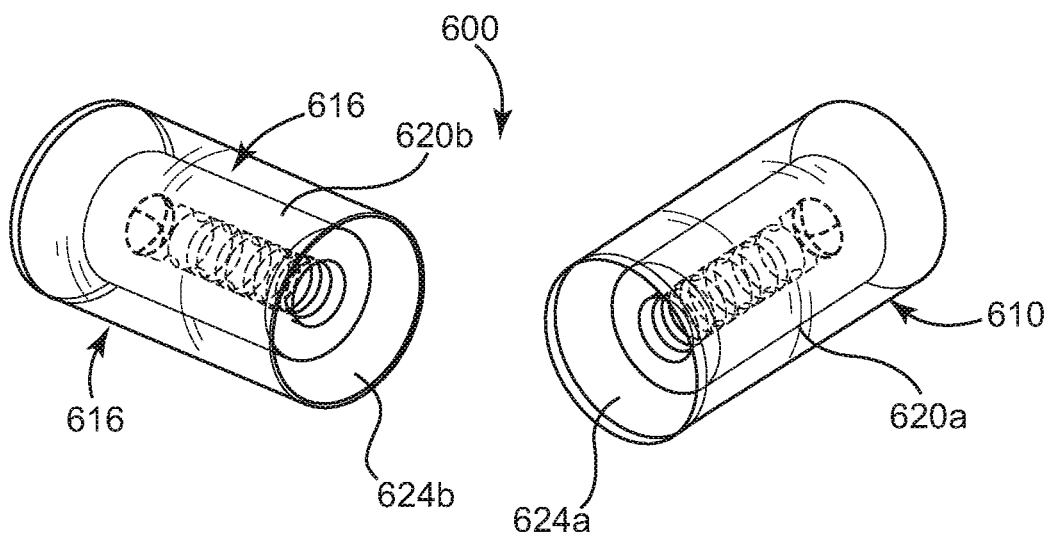

FIGS. 17 and 18 show a combined sterilizing device 600 according to another illustrative embodiment. As shown in FIGS. 17 and 18, the sterilizing device 600 includes a housing 610 and a cover 616. Each of the housing 610 and the cover 616 contain a sterilizing element 620a and 620b, respectively. The sterilizing elements 620a and 620b can have any one of the configurations according to the various embodiments described above. The cover 616 is coupled to the housing 610 via a frangible seal 630, as shown in FIG. 17. The cover 616 can be separated from the housing 610 by a twisting and pulling motion to gain access to the sterilizing elements 620a and 620b through separate openings 624a and 624b located in the housing 610 and the cover 616, respectively. The housing and cover portions 610 and 616 of the device 600 can be used separately to clean and sterilize the working end-sites of one or more devices to be sterilized. According to further embodiments, the sterilizing elements 620a and 620b contained within the housing 610 and cover 616, respectively, can have the same or different configurations. Additionally, the sterilizing elements 620a and 620b can be pre-moistened with the same or different antipathogenic agent. For example, the sterilizing element 620a located within the housing 610 can be contoured so as to contact and engage the surfaces of male devices and can be pre-moistened with a first antipathogenic agent, and the sterilizing element 620b located within the cover 616 can be contoured so as to contact and engage the inner surfaces and a device having a lumen and/or septum and can be pre-moistened with the same or a second antipathogenic agent. According to other embodiments, the first sterilizing element 620a can be pre-moistened with an antipathogenic agent and is used to clean and sterilize the working end-site. The second sterilizing element 620b can be dry and used to dry the working end-site after it has been cleaned using the first sterilizing element 620a. The cover 616 including the dry sterilizing element 620b may be left engaged with the working end-site until the site is ready for use.

Figure 19A:
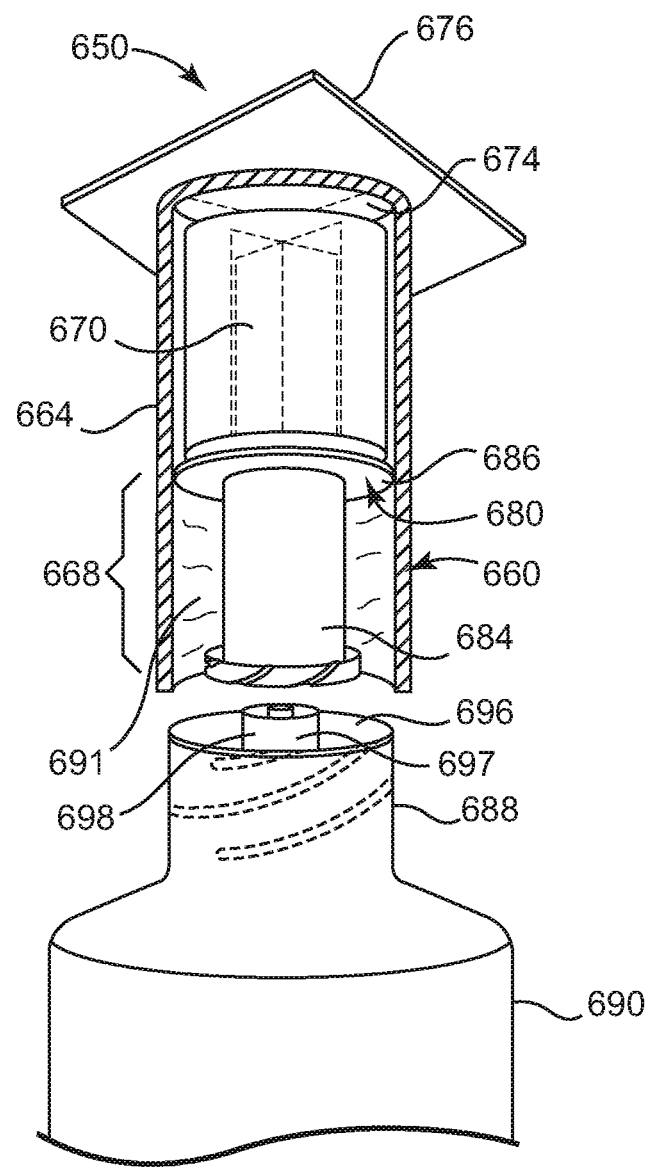
FIGS. 19A and B are partial cut-away views of a sterilizing device configured to be attachable to a syringe according to various embodiments.

FIGS. 19A and B are partial cut-away views of a sterilizing device 650 according to various embodiments. As shown in both FIGS. 19A and 19B, the sterilizing device 650 includes an elongated housing 660 having an upper portion 664 and a lower portion 668. A pre-moistened sterilizing element 670, according to any one of the various embodiments as described above, is sealed within the upper portion 664 of the housing 660 by a frangible top 674. According to one embodiment, a protective cover 676, such as previously described above, can be provided over the frangible top 674. In one embodiment, as shown in FIG. 19A, the lower portion 668 of housing 660 includes a divider or partition 680 and a female luer 684 attached to an underside 686 of the divider 680. The female luer 684 is configured such that it can be secured onto a working end 688, for example, of a male luer lock syringe 690 or slip luer style syringe. The lower portion 668 of the housing 660 covers the syringe end 688 when the female luer 684 is coupled to the syringe end 688.

Figure 19B:
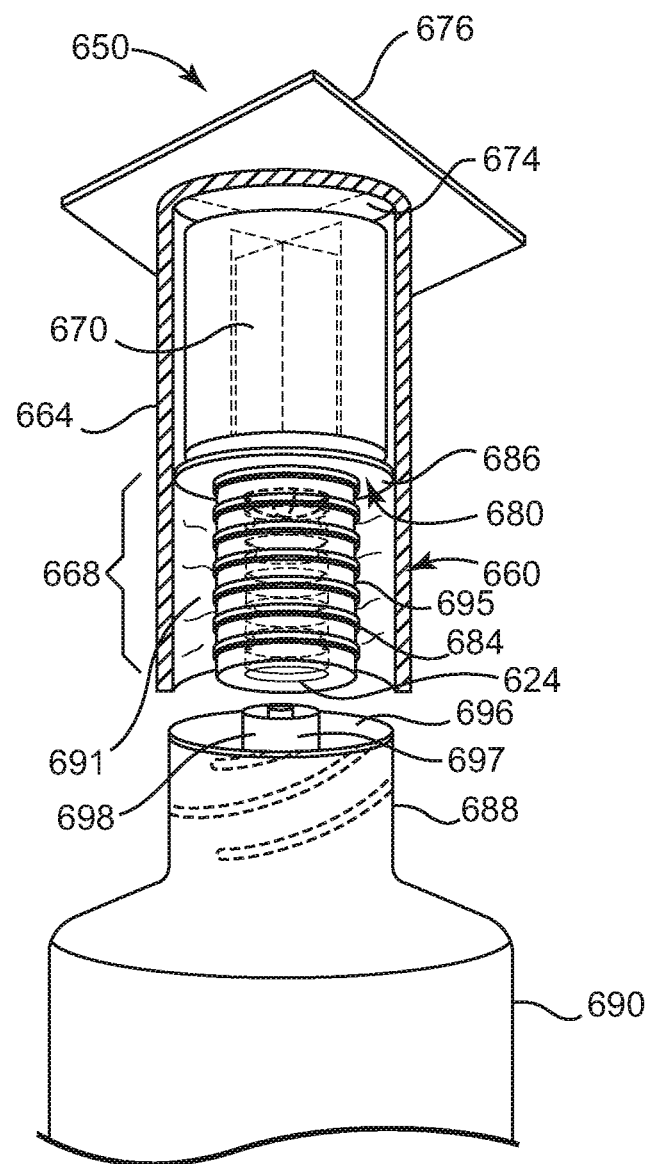

According to another embodiment, as shown in FIG. 19B, the lower portion 668 of the housing provides an inner surface to be retained onto the outside surface of the syringe 688. The lower portion 668 includes an inner lining 691 that has "gripable" or a textured surface that would allow the clinician to rotate the attached sterilizing device 650 either clockwise or counter clockwise in a manner to sterilize the end-site of the medical device while attached to the syringe end 668. The inner lining 691, along with a textured partition 680, provides a high-friction contact surface to prevent slippage of the housing 660 and particularly the lower portion 668 of the device 650 coupled to the syringe end 688. The gripable inner lining 691 having a textured surface provides an additional method of securing the sterilizing device 650 to the outer-housing of the syringe 690, particularly when the user is swabbing an end-site in a counter-clockwise direction where a partition 680 containing a female luer is coupled to the male luer lock on a syringe-end 688, such as shown in FIG. 19A, as it is generally recognized that a female luer coupled to a male luer lock are mechanically suitable for a clockwise rotation, but not a counter clockwise, rotation. Additionally, the lining 691 provides the additional high-friction for the user to turn the syringe 690 in a counter-clockwise direction to minimize the risk of the syringe 690 and sterilizing device 650 separating during a vigorous bi-directional (clockwise or counter clockwise) cleaning of the end-site. Further, in another embodiment, the lower portion 668 of the sterilizing device 650 does not include a female luer, and the inner lining 691, in conjunction with the textured/lined partition 680, provides the necessary grip alone to the syringe's outer-housing/shroud (i.e. male luer lock syringe) for a bi-directional cleaning.

Additionally, in some embodiments, as shown in FIG. 19B the lower portion 668 can also include a sterilizing element 695 configured such that the inner cavity 624 of the sterilizing element 695 as well as the exterior 684 of the sterilizing element 695 would provide an alternative method for gripping the inner surface 696 of the male luer lock syringe end 688 and/or in conjunction with the inner lining 691 and/or the outer surface 697 of the slip luer portion 698 of the syringe 690. Together or in part, the lower portion 668 inner lining 691 and/or the sterilizing element 695 would provide a friction fit such that the clinician can rotate in either a clockwise or counter clockwise direction to sterilizing the medical device end-site, with the sterilizing element 695. Thus, the device 650, as described above according to the various embodiments, serves as both a sterilizing device and as an end-cap to keep the syringe end sterile and free from debris until the syringe is ready for use. After the working end-site of the medical connector has been wiped free of debris and is sterilized using the device 650, the housing 660 and lower portion 668, including the female luer 684 and/or sterilizing element 695, can be disengaged from the male end 688 of the syringe 690, and the contents of the syringe 690 can then be injected into the working end-site of the sterilized medical connector.

Figure 20:
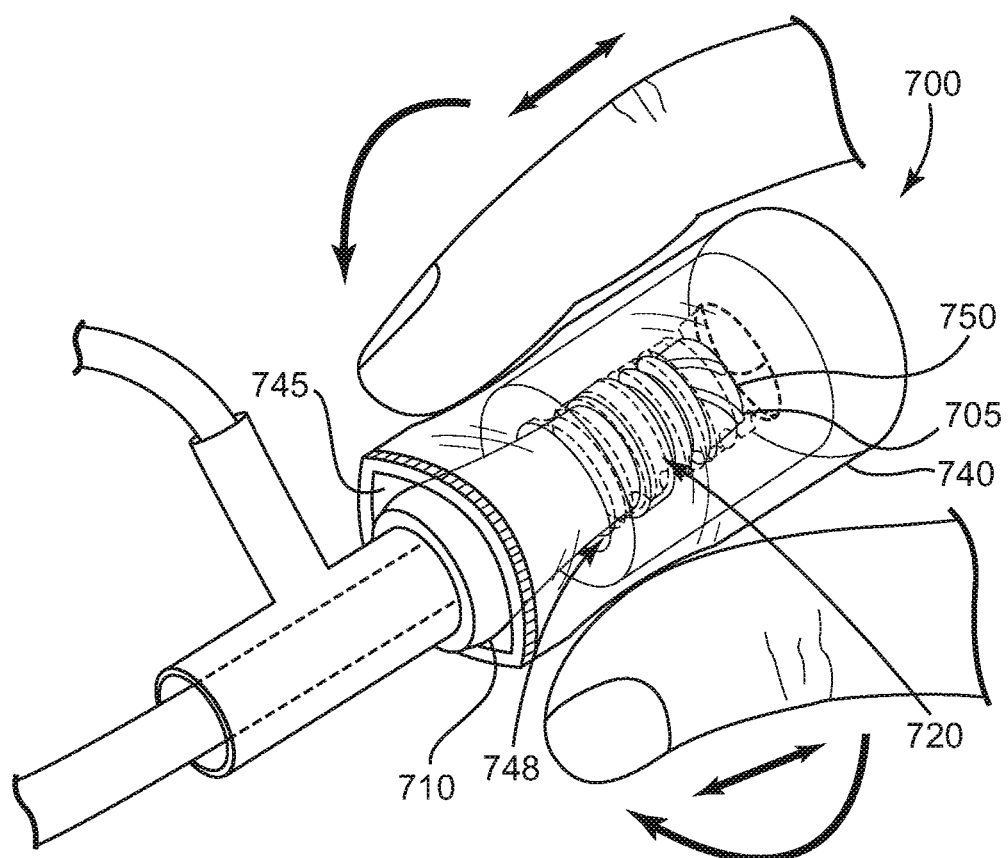
FIG. 20 is a perspective view of a sterilizing device including a sterilizing element provided in accordance with various embodiments, in use.

FIG. 20 shows a sterilizing device 700 according to the various embodiments which, as described above, can be used to sterilize the working end-site 705 of a medical device 710. The sterilizing device 700 is intended for a single application and should be disposed of in the appropriate waste receptacle. The sterilizing device 700 includes a contoured sterilizing element 720 pre-moistened with an antipathogenic agent contained within a housing 740. In order to use the sterilizing device 700, the protective cover (if present) is first removed. Next, the housing 740 is opened to facilitate access to the sterilizing element. According to some embodiments, the housing 740 can be opened by peeling away or removing a lid secured to the top of housing. In other embodiments, the housing 740 may be opened by the application of inward pressure on the housing side walls to either break a seal formed at the top of the housing 740 or to pop off a lid. In still other embodiments, a working end-site of a device to be sterilized can be forcibly engaged through a frangible pre-scored lid or foil/laminated top to gain access to the sterilizing element 720 contained within the housing 740.

Once the housing 740 has been opened, the working end-site 705 of the device to be sterilized 710 is then inserted through the opening 745 of the sterilizing device housing 740 to access the sterilizing element 720 contained within, as shown in FIG. 20. The end-site 705 is inserted into the recessed portion 748 of the sterilizing element 720, such that the sterilizing element 720 contours to the outer threads, edges, sides, and inner lumen surfaces of the medical connector end. As shown in FIG. 20, the sterilizing element 720 includes a recessed portion 748 configured to contour to the outer surfaces and threads of the end-site and a raised base portion 750 adapted to contact and engage the distal end including the distal tip of the working end-site 705 as well as the inner lumen of the medical connector, as described above.

Debris is cleared from and an inclusive layer of antipathogenic agent is applied to the end surfaces of the working end-site 705 with the contoured sterilizing element 720 using a wiping and/or twisting motion for sufficient amount of time so as to achieve a specific "kill of microbes." According to some embodiments, cleaning and sterilizing the working end-site 705 includes expelling the antipathogenic agent onto the working end-site 705. For example, in one embodiment, the working end-site 705 is compressed into the sterilizing element 720 to expel the antipathogenic agent from the element 720 and onto the working end-site 705. In another exemplary embodiment, the antipathogenic agent can be expelled onto the working end-site 705 by squeezing the sidewalls of the housing 740 to compress the sterilizing element 720 contained therein to expel the antipathogenic agent onto the working end-site 705. According to one embodiment, the cleaning time is less than about 30 seconds. According to another embodiment, the cleaning time ranges from about 20 to about 30 seconds; from about 15 to about 30 seconds; or from about 10 to about 30 seconds. In some embodiments, the sterilizing device 740 may be left engaged with the working end-site 710 until ready for use.

Once the working end-site 705 has been cleaned and sterilized for the appropriate amount of time, the working end-site then can be removed from the sterilizing element 720 and the housing 740, and allowed to air dry prior to connection of another compatible device or an injection made therein with a syringe. According to one embodiment, the drying rate after the antipathogenic agent has been applied to the working end-site is less than about 15 seconds. In other embodiments, the drying rate is less than about 10 seconds. In still other embodiments, the drying rate is less than about 7 seconds.

In other embodiments, a second end of the sterilizing device or an additional device including a dry element may be used to wipe dry the working end-site 705 after it has been cleaned and sterilized as described above. The second end or additional drying device may be left in place engaged within the working end-site until ready for use.

Figure 21A:
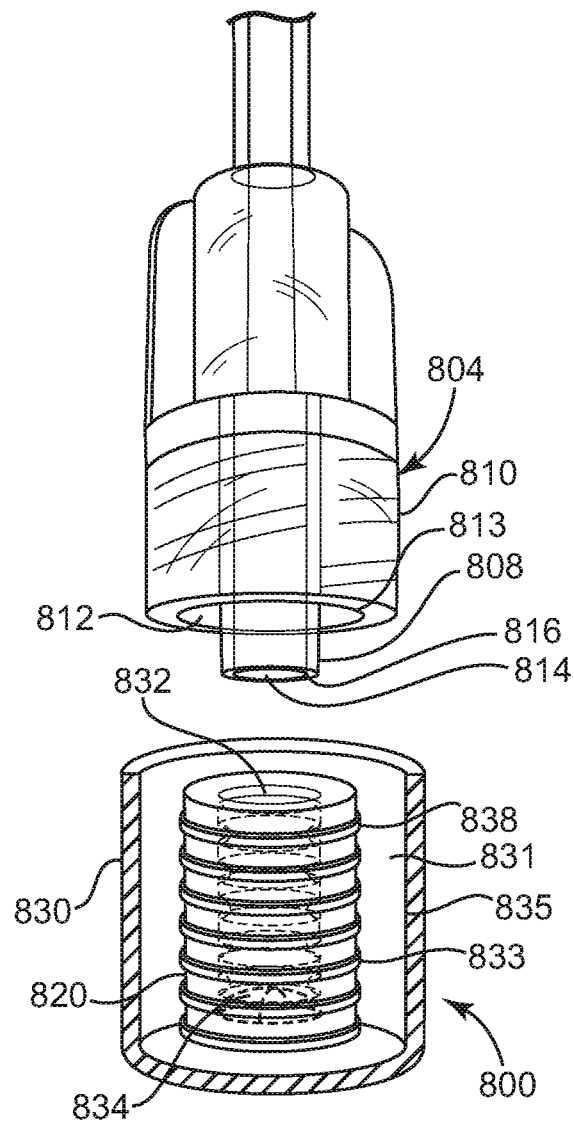
FIG. 21A is a partial cut-away view of a sterilizing device provided in accordance with various embodiments and a male luer lock connector end.

FIG. 21A is a partial cut-away view of a sterilizing device 800 provided in accordance with various embodiments and an exemplary connector end 804. As shown in FIG. 21A, the exemplary connector end 804 is a male luer lock connector including a male slip luer component 808 and a shroud 810 that covers and protects the slip luer component 808. An internal cavity 812 is defined between the shroud 810 and the slip luer component 808. The internal cavity 812 may include a plurality of internal threads provided on an inner wall or surface 813 of the shroud 810. The male slip luer component 808 includes a lumen 814 having an inner surface 816 and completes the fluid pathway common to male luer lock connectors.

According to various embodiments, the sterilizing device 800 includes a sterilizing element 820 contained within a housing 830. The sterilizing element 820 can have any one of the configurations according to the various embodiments described above. In one exemplary embodiment, the sterilizing element 820 includes an absorbent material pre-moistened with an antipathogenic agent. In certain embodiments, as shown in FIG. 21A. The housing 830 defines a cavity 831 between an outer surface 833 of the sterilizing element 820 and an inner wall 835 of the housing 830 to receive and couple with the male luer lock shroud 810. Additionally, the sterilizing element 820 includes a recessed portion 832 configured to receive and conform to the male slip luer component 808 (if present). Additionally, the sterilizing element 820 includes a raised base portion 834 configured to project into and engage an inner surface 816 of the slip luer lumen 814. Further, in certain embodiments, the outer surface 833 of the sterilizing element can be contoured to include, but not limited, ribs, threads, flanges or raised structures 838 and to contact all inner walls of the shroud 810 and to facilitate the wiping and sterilizing therein. The housing 830 can have a number of configurations, according to the various embodiments described above.

Figure 21B:
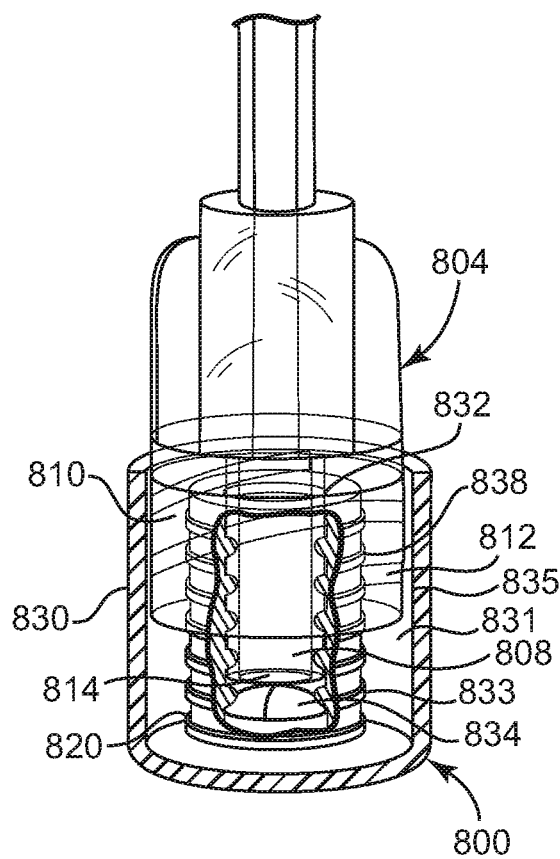
FIG. 21B is a partial cut-away view of the sterilizing device shown in FIG. 21A used to clean the male luer lock connector end.

FIG. 21B is a partial cut-away view of the sterilizing device 800 coupled with the male luer lock connector 804. In certain embodiments, as shown in FIG. 21B, the housing 830 is sized to fit over the shroud 810. The male slip luer component 808 (if present) is received and engaged in the recessed portion 832 of the sterilizing element. The sterilizing element 820, as shown in FIG. 21B, fills the internal cavity 812 defined by the shroud 810. Additionally, the shroud 810 fits sufficiently in housing cavity 831 between inner housing wall 835 and the outer wall 833 of the sterilizing element 820. The raised base portion 834 projects into and engages the inner surface 816 of the slip luer lumen 814. In some embodiments, the outer wall 833 of the sterilizing element 820 may include external surface features 838 configured to engage and contact any internal threads provided on the internal surfaces 813 of the shroud 810. Once the male luer connector 804 is engaged within the sterilizing element 820 contained within the housing 830, a wiping and/or twisting motion can be employed to wipe debris from and apply an inclusive layer of the antipathogenic agent to the inner and outer surfaces 812 of the male luer connector 804 including the inner surface 816 of the lumen 814. Once the male luer connector 804 has been effectively cleaned and sterilized, the sterilizing device 800 can be left on the end-site to protect its sterility until time of use and then disposed of in the appropriate waste receptacle. In certain embodiments, such as in the absence of a male connection component, the sterilizing element can be inserted into the cavity 831 defined by the shroud 810. Once the sterilizing element is engaged in the shroud, a wiping and/or twisting motion can be employed to clean and sterilize the surfaces of the medical device to be cleaned. The sterilizing device 820 can be left engaged in the shroud 810 until the device is ready for use.

Figure 22A:
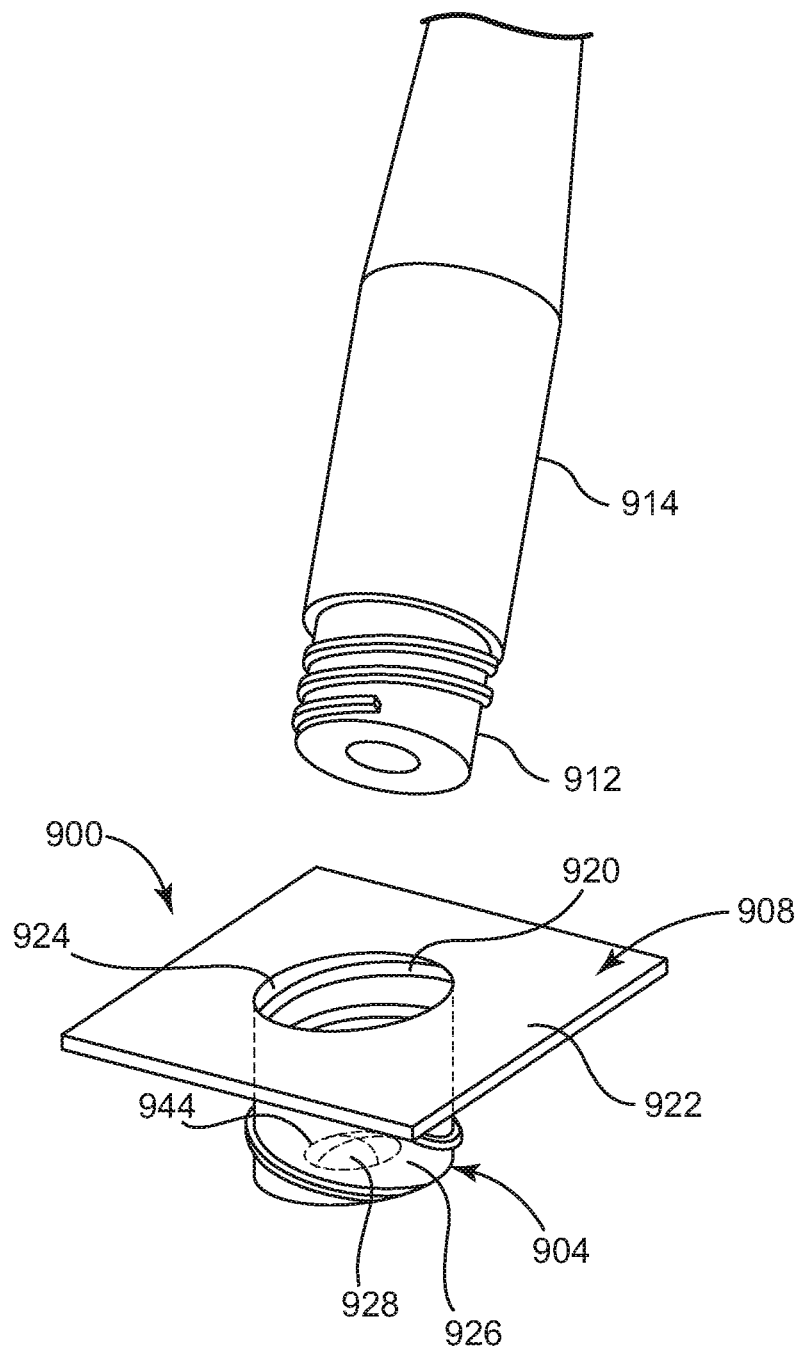
FIGS. 22A and 22B are isometric views of a contoured sterilizing tool according to another illustrative embodiment.
Figure 22B:
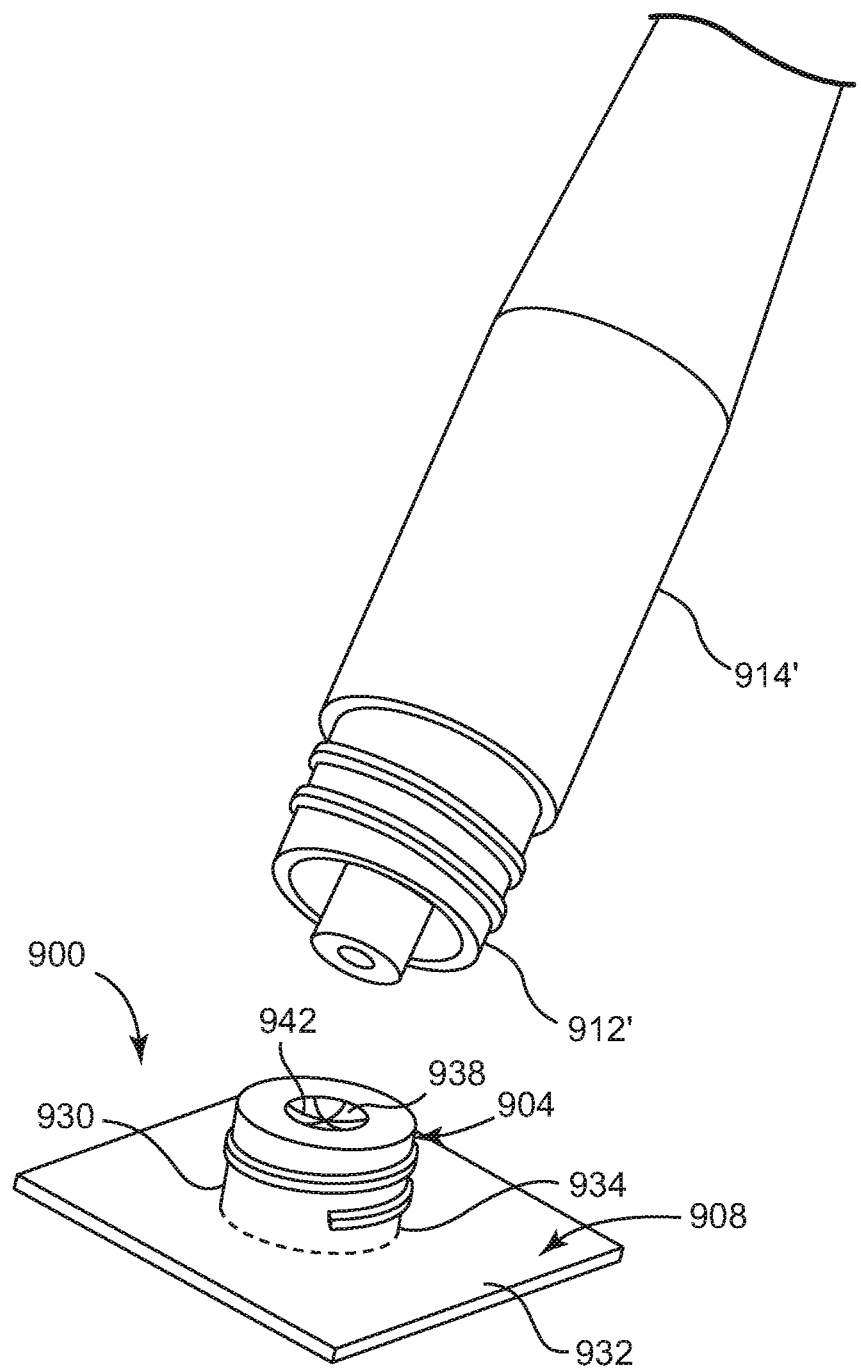

FIGS. 22A and 22B are isometric views of a contoured sterilizing tool 900 according to another illustrative embodiment. As shown in FIGS. 22A and 22B, the contoured sterilizing tool 900 includes a contoured sterilizing element 904 transposed into and onto a single planar sheet 908 of a resilient material. The contoured sterilizing element 904 is transposed into the sheet 908 such that either or both sides of the contoured sterilizing tool 900 can be utilized for wiping and sterilizing a working end-site 912, 912' of a medical device 914, 914'. The contoured sterilizing tool 900 can be left on the medical device end-site 912, 912' to keep it sterile and clean until access is required.

The contoured sterilizing element 904 is transposed in the resilient, planar sheet 908 such that it defines a cavity 920 in an upper planar surface 922 of the planar sheet 908. The cavity 920 includes an inner surface 924 configured to receive a working end-site of a medical device therein such as, for example, the female-type working end-site 912 of a medical device 914 as shown in FIG. 22A. The inner surface 924 is configured to conform and contour to and to contact the outer and inner surfaces of the working end-end site 912 and, in some embodiments, can include any number of raised structures including ribs, threads, ridges, micropatterned features, microtextured features and the like configured to conform and to contact the surfaces to be sterilized. In some embodiments, the cavity 920 includes a base surface 926 including a raised base portion 928 configured to contact and to engage an inner surface of the working end-site of a medical device such as, for example, a lumen, a distal end and/or a septum. To accomplish this, the raised base portion 928 can have any number of configurations. For example, the raised base portion 928 can be configured as any one of a nipple, bump, nub, tine, or other similar projection.

The contoured sterilizing element 904 is transposed in the resilient, planar sheet 908 such that in addition to defining the cavity 920, the contoured sterilizing element 904 also defines an outwardly projecting portion 930. The outwardly projecting portion 930 projects away from the lower planar surface 932 of the resilient planar sheet 908. In some embodiments, the outwardly projecting portion 930 has an outer shape that complements the inner shape of the cavity 920. The outwardly projecting portion 930 includes an outer surface 934 shaped to conform and contour to and to contact the outer and inner surfaces of a medical device end-site such as, for example, the male-type working end-site 912' of a medical device 914' as shown in FIG. 22B. Additionally, the outer surface 934 of the outwardly projecting portion 930 can include any number of raised structures including ribs, threads, ridges, microtextured features, micropatterned features and the like configured to contact and conform to the surfaces to be sterilized. In some embodiments, the outwardly projecting portion 930 includes a recessed portion 938 shaped to receive the outer and inner surfaces of a working end-site of a medical device therein. In one embodiment, the recessed portion 938 has an exterior shape 942 that is transposed to complement an interior shape 944 of the raised base portion 928 formed as part of the cavity 920.

Figure 23:
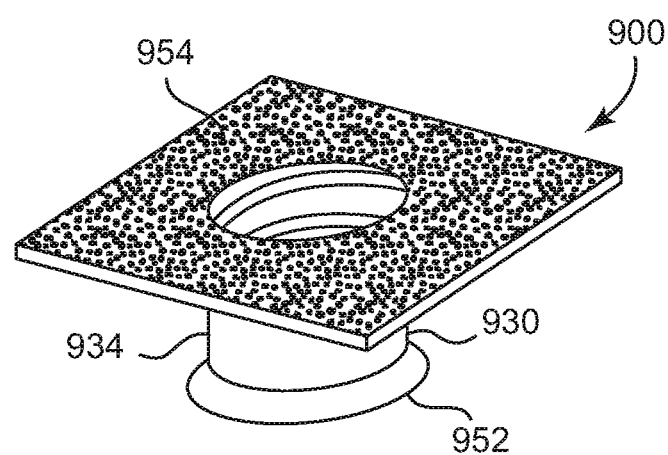
FIG. 23 is an isometric view of a contoured sterilizing tool according to another illustrative embodiment.

FIG. 23 is an isometric view of a contoured sterilizing tool 900 according to another illustrative embodiment. As shown in FIG. 23, the contoured sterilizing tool 900 can include a finger grip 952 formed on the outer surface 934 of the outwardly projecting portion 930. Additionally, the contoured sterilizing tool 900 can include a plurality of surface texturing features 954 formed on the upper planar surface 922 and/or lower planar surface 932 of the resilient planar sheet 908. The surface texturing features 954 can have any configuration designed to facilitate gripping of the tool 900 including, but not limited to, ridges, bumps, surface roughing, rings, concentric circles, lattice features and the like. The finger grip 952 and/or surface texturing features 954 are provided to facilitate gripping and manipulation of the tool 900 by the user.

Figure 24:
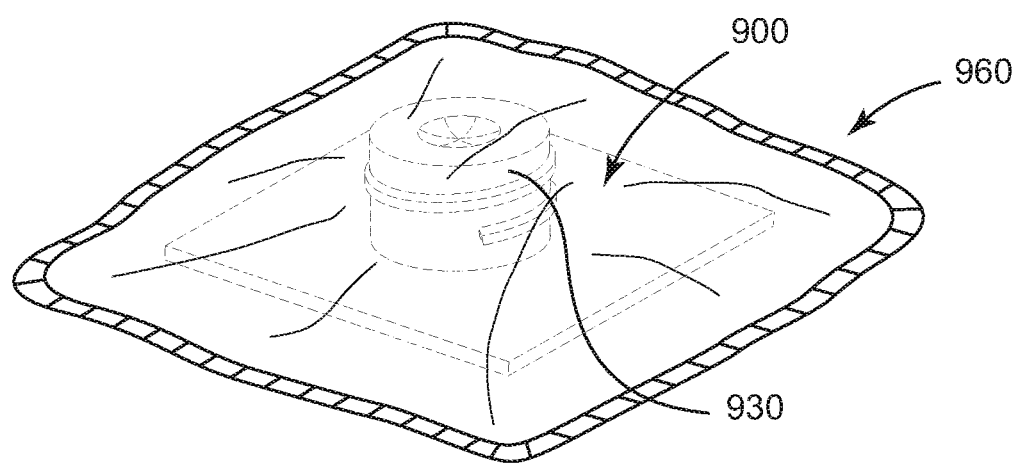
FIG. 24 is a schematic view of a contoured sterilizing tool provided in accordance with an embodiment contained within a packaging.

FIG. 24 is a schematic view of a contoured sterilizing tool 900, such as described above in reference to FIGS. 22A-23, contained within a packaging 960. The packaging 960 is adapted to maintain a sterile and/or moisture-rich environment within the packaging 960 when the packing is sealed. In some embodiments, the packaging 960 is an easy-tear packaging that can be easily torn open by the user to access the sterilizing tool 900 contained within. In one embodiment, as shown, the contoured sterilizing tool 900 is adapted to be compressed to substantially flatten the transposed configuration within the packaging 960. When the packaging 960 is opened and the sterilizing tool 900 removed, the resiliency of the material used to fabricate the tool 900 facilitates the outward projecting portion 930 of the sterilizing tool 900 to re-expand to an uncompressed configuration ready for use as shown, for example, in either FIG. 22A or FIG. 22B.

According to various embodiments, the contoured sterilizing tool 900 can be fabricated from a resilient, planar sheet of material 908. The resilient planar sheet of material 908 can be selected from a wide variety of resilient materials of varying durometers and elasticity. Exemplary resilient materials include, but are not limited to silicones, rubbers including latex-free rubbers, viscoelastic foams, ethylene propylene diene monomer rubbers (EPDM) and other suitable materials known to those of skill in the art. In some embodiments, the contoured sterilizing tool 900 can be made of a translucent, transparent or optically clear resilient elastomeric material such as a silicone or a latex-free rubber. A translucent or optically clear sterilizing tool 900 assists the user in visualizing and to see-through a change in the appearance of either the working end-site and/or the sterilizing tool itself during the cleaning and sterilization of the working end-site.

The contoured sterilizing tool 900 including the contoured sterilizing element 904, as described above according to the various embodiments, can be transposed in the resilient, planar sheet 908 using a variety of manufacturing techniques. Exemplary techniques suitable for fabricating the sterilizing tool 900 include various molding methods such as transfer, compression or injection molding or other similar techniques. According to one embodiment, the contoured sterilizing element 904 can be pressed or molded into the resilient, planar sheet 908.

In several embodiments, the resilient material used to form the resilient, planar sheet 908 is impregnated with a liquid or dry antipathogenic agent, such as described in detail above, for applying an inclusive layer of an antipathogenic agent to the inner and outer surfaces of the working end-site of a medical device for sterilization. In some embodiments, the resilient planar sheet 908 can also be impregnated with a visual-change reactant. The visual-change reactant may cause the contoured sterilizing tool 900 and/or the working end-site to undergo a visual change indicating that the working end-site of the medical device has been adequately sterilized and is ready for use. For example, in one embodiment, the sterilizing tool 900 can be impregnated with a visual change reactant that when applied to the surface of the working end-site, causes the working end-site to change color. In a further embodiment, the visual change reactant undergoes an additional color change when the working-end site is dried. Exemplary agents suitable for this purpose include dyes, reactants, catalysts and other similar agents suitable for this purpose known to those of skill in the art.

In some embodiments, the contoured sterilizing tool 900 is made from a translucent or transparent material and provides a visual "see through" indication that the working end-site has received exposure from the antipathogenic agent contained within the contoured sterilizing tool 900, causing a visual discoloration of the working end-site and indicating that the working end-site has been sterilized and is ready for use. In some embodiments, the contoured sterilizing tool 900 is impregnated with an antipathogenic agent releases the antipathogenic agent upon contact with the working end-site of the medical device, wetting the surface with the antipathogenic agent causing a visual change in the end-site due to a microporous (e.g., polymeric porous permeable polymer), micropatterned, bonded coating or solvatochromic dyed surface (e.g., merocyanine dye or Reichardt's dye) of the end-site. In another embodiment the translucent/transparent contoured sterilizing tool 900 itself can include a micropatterned (e.g., fine lines or cracks), microtextured or a microporous surface whereby refraction occurs when the wetted, "resilient" surface of the contoured sterilizing tool 900 contacts the "harder," more rigid surfaces of the end-site, causing a visual change to occur from a darker appearance when contact is first made (i.e. wetted) to a lighter appearance as when the sterilizing tool 900 is left in place on the working end-site and the antipathogenic agent dries and/or evaporates. In further embodiments, the sterilizing tool 900 visually changes from a first state to a second state or similarly from visually light to visually dark or from a dark to a light surface over time due to exposure to an antipathogenic agent, and from a wetted surface to a dry surface. In other embodiments, the sterilizing tool 900 undergoes a visual change in response to manual pressure applied to the tool 900. According to the various embodiments described above, the visual change can be a color change. In other embodiments, the micropattern or microtexturing provides an additional refinement to the contour sterilizing tool for contacting and cleaning intricate details on an end-site such as cracks, crevices or grooves and where microscopic bacterium can reside on an end-site and particularly where an end-site has been assembled with multiple components having microscopic surfaces that can harbor bacterium (e.g. needle-less connector having assembled components such as a housing, seals, valve or septum). The microtexturing or micropattern can include ridges, bumps, surface roughing, rings, concentric circles, lattice features and the like. In a further embodiment of the contour sterilizing element 900 can include a microporous surface adapted to retain a measured amount of an antipathogenic agent such that the sterilizing element 900 is adapted apply an inclusive layer to an end-site in a manner to promote a fast drying rate. In yet another embodiment, the microporous surface is adapted to deliver a pre-determined amount of antipathogenic agent for the purpose of leaving a measured amount of antipathogenic residue to maintain the sterility on the end-site.

Figure 25:
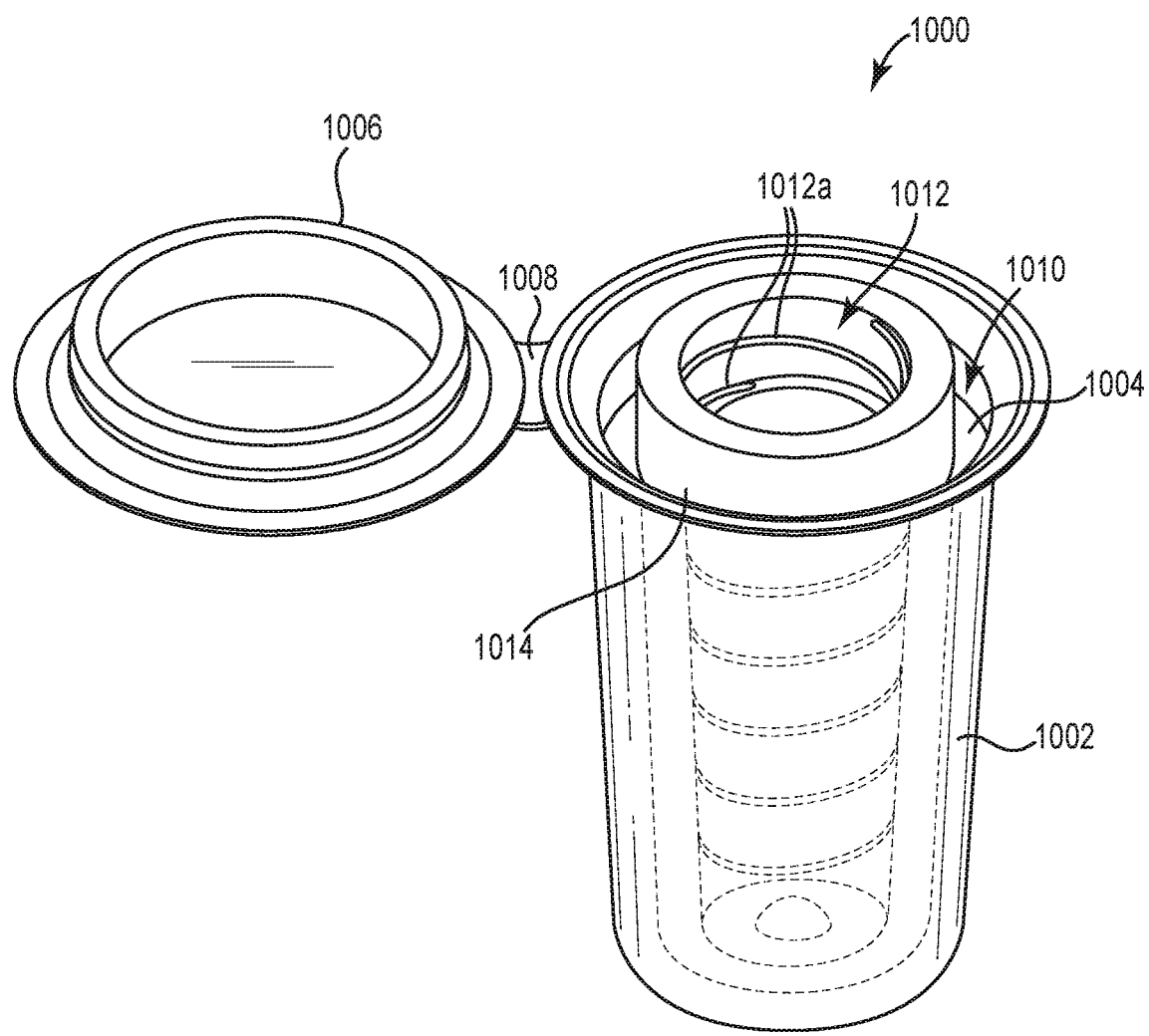
FIG. 25 is an isometric view of a sterilization device in accordance with another illustrative embodiment including a tethered cap.

FIG. 25 is an isometric view of a sterilizing device 1000 in accordance with another illustrative embodiment. In the embodiment of FIG. 25, the sterilization device 1000 includes housing 1002 containing a contoured sterilization element 1004, and a cap 1006 that is releasably secured to the housing 1002. In some embodiments, and as shown in FIG. 25, the cap 1006 is permanently secured to housing 1002 via a tether 1008. The tether 1008 can comprise, for example, a flexible hinge (e.g., a living hinge), wire, strap, or other suitable connecting member coupled to or formed integrally with the cap 1006 and/or housing 1002. In other embodiments, the cap 1006 is initially secured to the housing 1002, but is configured such that the cap 1006 can be easily removed from the housing 1002 in preparation for sterilizing the working end-site of a medical device. As discussed in greater detail herein, and in some embodiments, the cap 1006 is configured to lift off and disengage from the housing 1002 in response to a sufficient lateral pressure asserted against the sides of the housing 1002 by the user's fingers. In some cases, this ability to open the cap 1006 while also holding the sterilizing device 1000 with the same hand allows the user to more easily manipulate the working end-site of the device to be sterilized with the user's other hand. In some cases, this may also prevent undesired contact of the user's fingers with the working end-site as well as the exposed surfaces of the sterilizing device 1000.

Prior to use, the cap 1006 is attached to the housing 1002 and serves to hermetically seal an interior space 1010 of the housing 1002, thus maintaining the sterilizing element 1004 in a moist state to prevent the sterilizing element 1004 from drying out until it is ready for use. The hermetic seal provided by the cap 1006 also serves to prevent external moisture, debris, and other contaminants within the environment from coming into contact with the sterilization element 1004. As with other embodiments described herein, the housing 1002 and cap 1006 also provide a barrier to direct contact with the sterilizing element 1004, and serves as a tool for mechanically manipulating the sterilizing element 1004.

Upon inserting the working end-site of a device into the interior of the sterilizing element 1004, and in some embodiments, the sterilizing element 1004 is configured to apply an inclusive layer of an antipathogenic agent (e.g., isopropyl alcohol) to the inner and outer surfaces of the working end-site. Although the example sterilizing element 1004 as shown in FIG. 25 includes an interior set of contours or threads 1012*a* that contact and engage the working end-site of the device, other configurations can be employed. For example, the sterilizing element 1004 can have a composition and structure similar to that of one of the sterilizing elements 20 shown in FIGS. 2A-2C, or the contoured sterilizing element 1100 shown in FIGS. 32-34, as discussed further below.

The sterilizing element 1004 can be made from a variety of materials including, but not limited to, non-woven, particulate-free absorbent foams, natural or synthetic sponges, or other suitable materials both semi-flexible or semi-rigid and having malleable, resilient and rebounding properties. In some embodiments, the sterilizing element 1004 includes an absorbent foam article 1014. In other embodiments, the sterilizing element 1004 is formed from an absorbent, viscoelastic resilient foam, porous polymeric plastic, urethane, thermoplastic or cellular thermoplastic, silicone or silicone rubber. In one embodiment, the sterilizing element 1004 can be fabricated from a hydrophilic polymer, which can be manufactured in a variety of different shapes using an extrusion, molding, overmolding, or other suitable manufacturing process. In some embodiments, the material of the sterilizing element 1004 has capillarity (capillary action), which may also be referred to as a wicking capability, and the properties to disperse a liquid anti-pathogenic evenly throughout and to maintain an even distribution regardless of the sterilizing device's 1000 orientation when stored either upside down, right side-up or on its side; it will have sufficient antipathogenic agent distributed throughout to disinfect the end-site. In some embodiments, the sterilizing element includes a controlled time released active antipathogenic agent.

The sterilizing element 1004 can be secured within the interior space 1010 of the housing 1002 to prevent dislodgement of the element 1004 from the working end-site of a device being sterilized. In some embodiments, the sterilizing element 1004 is secured within the housing 1002 such that it can withstand vigorous wiping of an end-site. The sterilizing element 1004 can be secured within the housing 1002 by various methods including, but not limited to, ultrasonic welding, inward indentations of the walls, internal molded ribs or points, adhesives, fusing, overmolding, frictional engagement, as well as the sterilizing element's own outward expanding radial force to hold it in place within the housing 1002. In certain embodiments, the housing 1002 and sterilizing element 1004 can be formed from a single, unitary member. For example, in one embodiment the sterilizing element 1004 comprises a porous polymeric material that can be integrally formed with the housing 1002 using an injection molding, or insert molding, or overmolding process. In one exemplary embodiment, the sterilizing element 1004 is an inner lining along the inner surface of the housing 1002. The lining can be integral with the housing 1002 and can be made of a particulate free absorbent or porous-like material. The absorbent material is pre-moistened with an antipathogenic agent, as described above, and the sterilizing element 1004 lines the inner walls of the housing 1002. The inner lining is contoured and can include a plurality of raised ridges, ribs or threads configured to engage the threads, sides, and/or edges on the working end-site. Additionally, the inner lining includes a raised base configured to project into and to engage the inner luer lumen and/or contact the terminal end such as a septum of a needleless connector.

In some embodiments, the sterilizing element 1004 may be removed and disengaged from the housing 1002 for attachment to and sterilizing of the end-site, as well as be directly held by and in the hand of the user to sterilize the end-site. In some embodiments, the sterilizing element 1004 may be disengaged from the housing 1002 by twisting the housing 1002 to release the sterilizing element 1004 onto the end-site for direct attachment to and sterilizing of the end-site. In certain embodiments, the sterilizing element 1004 has an inclusive layer of antipathogenic to sterilize both the working end-site and the user's fingers. In some embodiments, the sterilizing element 1004 is removed from the housing 1002 and has a protective skin on the exterior of the sterilizing element 1004. The protective skin prevents the sterilizing element 1004 form drying out. In some embodiments, the skin provides a barrier and prevents users from contacting the disinfectant with their fingers when the sterilizing element 1004 is removed from the housing 1002 and manually handled. In some embodiments, the sterilizing element 1004 is impregnated with a liquid antipathogenic agent that evaporates when attached to the end-site. In some embodiments the sterilizing element 1004 is impregnated with a liquid antipathogenic agent and is left on the end-site until sterilizing element 1004 is dry. In some embodiments the sterilizing element 1004 visually changes color to signify it is dry. In some embodiments the sterilizing element 1004 is removed from the housing 1002 and squeezed to expel the liquid antipathogenic from the impregnated sterilizing element 1004. In some embodiments, the sterilizing element 1004 is impregnated with a dry bonded antipathogenic agent that disinfects and sterilizes when left in place on the end-site. In some embodiments, the dry bonded agent is activated by contact-pressure and/or friction when manipulated onto the end-site and by the users handling and fingers. The dry antipathogenic agent is bonded onto the sterilizing element 1004 as microparticles or nanoparticles, which are disrupted or activated, with a combination of contact pressure and friction when attached to the end-site causing the surface of the sterilizing element 1004 to have disinfecting properties and sterilize the end-site. In some embodiments the dry antipathogenic agent is bonded onto the sterilizing element 1004 as microparticles or nanoparticles, and is activated or disrupted, when the user's finger squeezes the sterilizing element 1004 or housing 1002. Additionally, in some embodiments the antipathogenic mechanism of action is "membrane disruption" either by a naturally occurring peptide or a synthesized molecule that mimics the structure of peptides such as an amphiphilic polymer, or similar such polymer, applied to the surface of the sterilizing element 1004. Alternatively, the sterilizing element 1004 may be left in place within the housing 1002 and the whole device 1000 can be left on the end-site for the purpose of protecting the site's sterility until such time the device is removed so that the site end can be used.

In some embodiments, the sterilizing element 1004 can be pre-shaped or pre-molded such that it is configured to contour to the surfaces of the working end to be sterilized. For example, in some embodiments, the sterilizing element 1004 can be contoured and pre-shaped such that it is configured to form-fit over the working end-site of a medical connector, catheter hub, luer compatible connector, luer component, and/or needle access port for efficient wiping and sterilizing. In other embodiments, the sterilizing element 1004 can be shaped to contour to and engage an inner lumen, septum, port, and/or needleless injection site. In other embodiments, material of the sterilizing element 1004 can be an extending portion 1014 above the base of the sterilizing element 1004. The elevated sterilizing element 1014 provides sufficient space to engage a female needleless valve. In some embodiments, the extending portion 1014 has internal contours 1012a to disinfect as well as help secure the device 1000 to the medical end-site or female needleless valve. In some embodiments, the extending portion 1014 is configured to disinfect a male luer lock and its respective shroud and slip-luer aspects. In some embodiments the extending portion 1014 has external contours to disinfect the shroud portion and internal threading such as on the male luer lock. The external contours also provide a mechanism to secure the device 1000 onto the end-site such as a male luer lock. The extending portion 1014 provides additional room along within the interior space 1010 to provide clearance for an end-site with a shroud, such as male luer lock, without interfering with the inside housing 1002 and the base sterilizing element 1004, especially during a vigorous twisting and turning. In other embodiments, a micropatterned or micro-contoured surface on the sterilizing element 1004 provides an additional refinement to the sterilizing device for contacting and cleaning intricate details on an end-site such as cracks, crevices or grooves and where microscopic bacterium can reside on an end-site, and particularly, where an end-site has been assembled with multiple components having microscopic surfaces that can harbor bacterium (e.g. needle-less connector having assembled components such as a housing, seals, valve or septum). The micro-contours or micropatterning can include any one of a number microtextures such as ridges, bumps, surface roughing, rings, concentric circles, dimples, lattice features, and the like. Such micro-contours may be included on all surfaces, including sidewalls, contours, inside surfaces or outside surface of the sterilizing element 1004, and such micro-contours may be configured to reduce the sterilization or disinfection time. In some embodiments, the micro-contours can be further refined to include nanotexturing on the micro-contours and can include a nanopattern that may be applied to the surface. In some embodiments, the antipathogenic is on the micro-contours or between the microtexturing or is a compond bonded into the micro-contours as nanoparticles. Further embodiments include a nanoscale antipathogenic factor for which the nanoparticles are substantially smaller than the pathogens and which exhibits an antipathogenic effect and disrupts the cellular integrity of the pathogen through membrane disruption.

In certain embodiments, the sterilizing element 1004 is configured to engage a working end-site of a medical device such that a friction fit is created between the sterilizing element 1004 and the end-site of the medical device. The sterilizing element 1004 can remain frictionally engaged with the working end-site until ready for use. In some embodiments, the absorbent foam material is sufficiently resilient such that it conforms to the surfaces of the working end-site when the working end-site is depressed into the absorbent material.

According to various embodiments, the absorbent material of the sterilizing element 1004 includes an antipathogenic agent including any one of an antiseptic, disinfectant, microbiocidal, or combinations thereof to kill pathogens on the surfaces of the device. According to one embodiment, an antipathogenic agent is a dry agent bonded to the surfaces of the sterilizing element 1004. According to another embodiment, the sterilizing element 1004 is impregnated with an antipathogenic agent. For example, the sterilizing element 1004 may be impregnated with an oligodynamic metal such as gold, zinc, copper, or cerium. According to one embodiment, the sterilizing element 1004 may be impregnated with silver. In other embodiments, the absorbent material of the sterilizing element 1004 is pre-moistened with at least one antipathogenic agent. Exemplary antipathogenic agents include, but are not limited to, the following: isopropyl alcohol, povidone iodine, chlorhexidine gluconate, and other useful antipathogenic agents known to those of skill in the art. Additionally, depending on the antipathogenic agent used, a sufficient amount of antipathogenic agent can be incorporated into the absorbent material to achieve an acceptable ratio of "antipathogenic agent to dry-time," wherein a sufficient amount of antipathogenic agent is used to adequately disinfect the site end while at the same time achieving a fast drying rate. In some embodiments, a fast sterilization time is achieved by a combination of a highly contoured sterilizing element that both efficiently and purposefully contacts all detail surfaces and applies a sufficient amount of antipathogenic agent to dry quickly. In some embodiments, the sterilization time is less than 5 seconds.

The sterilizing element 1004 can be adapted to undergo a visual color change and/or can be impregnated with a visual change reactant that when applied to the working end-site of a device indicates that the end-site is sterilized, or is both sterilized and dry. In some embodiments, the housing 1002 and/or sterilizing element 1004 can be translucent or even transparent such that a visual change in the working end-site and/or the sterilizing element 1004 can be easily and readily observed by the user. In some embodiments, the sterilizing element 1004 is impregnated with an antipathogenic agent that releases an antipathogenic agent upon contact with the working end-site of the medical device, wetting the surface with the antipathogenic agent and causing a visual change in the end-site due to a microporous, micropatterned, bonded coating or solvatochromic dyed surface of the end-site. In another embodiment the translucent/transparent contoured sterilizing element 1004 itself can include a micropatterned (e.g., fine lines or cracks), microtextured or a microporous surface whereby refraction occurs when the wetted, "resilient" surface of the contoured sterilizing element 1004 contacts the "harder," more rigid surfaces of the end-site, causing a visual change to occur from a darker appearance when contact is first made (i.e. wetted) to a lighter appearance as when the sterilizing device 1000 is left in place on the working end-site and the antipathogenic agent dries and/or evaporates.

In some embodiments, the sterilizing device 1000 visually changes from a first state to a second state or similarly from visually light to visually dark or from a dark to a light surface over time due to exposure to an antipathogenic agent, and from a wetted surface to a dry surface. In other embodiments, the sterilizing device 1000 undergoes a visual change in response to manual pressure applied to the device 1000. In certain embodiments, the visual change can be a color change. In some embodiments, the micro-contours further aids in cleaning intricate details on an end-site such as cracks, crevices or grooves and where microscopic bacterium can reside on an end-site and particularly where an end-site has been assembled with multiple components having microscopic surfaces that can harbor bacterium. The micro-contours or micropattern can include ridges, bumps, surface roughing, rings, concentric circles, dimples, lattice features and the like. In a further embodiment, the sterilizing device 1000 can include a microporous surface adapted to retain a measured amount of an antipathogenic agent such that the sterilizing device 1000 is adapted to apply an inclusive layer to an end-site in a manner to promote a fast drying rate. In yet another embodiment, the microporous surface is adapted to deliver a pre-determined amount of antipathogenic agent for the purpose of leaving a measured amount of antipathogenic residue to maintain the sterility on the end-site.

Figure 26:
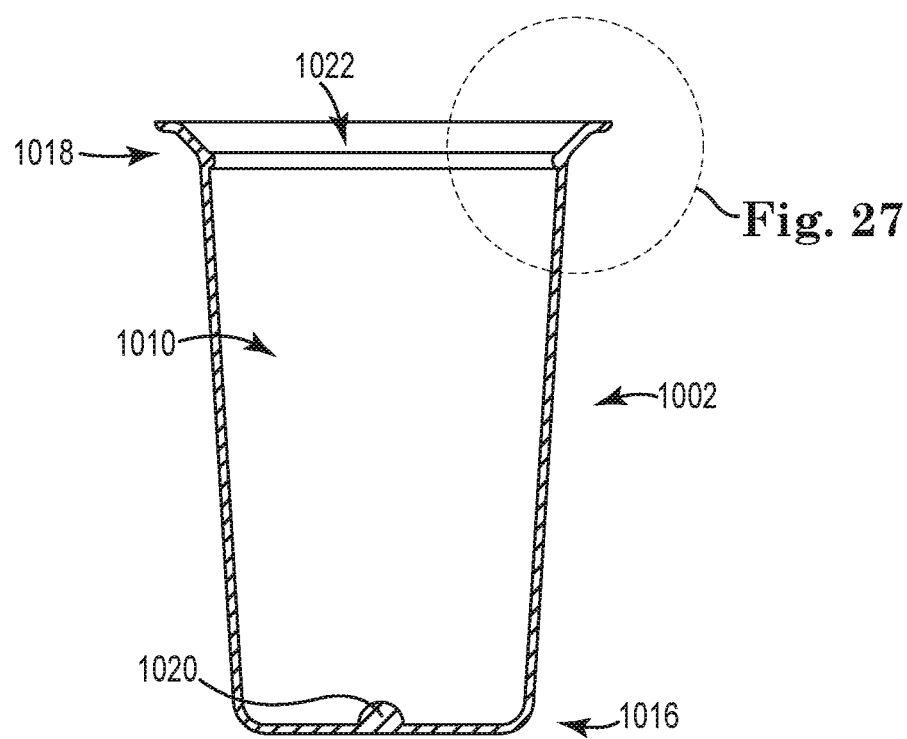
FIG. 26 is cross-sectional view showing the housing of FIG. 25 in greater detail.
Figure 27:
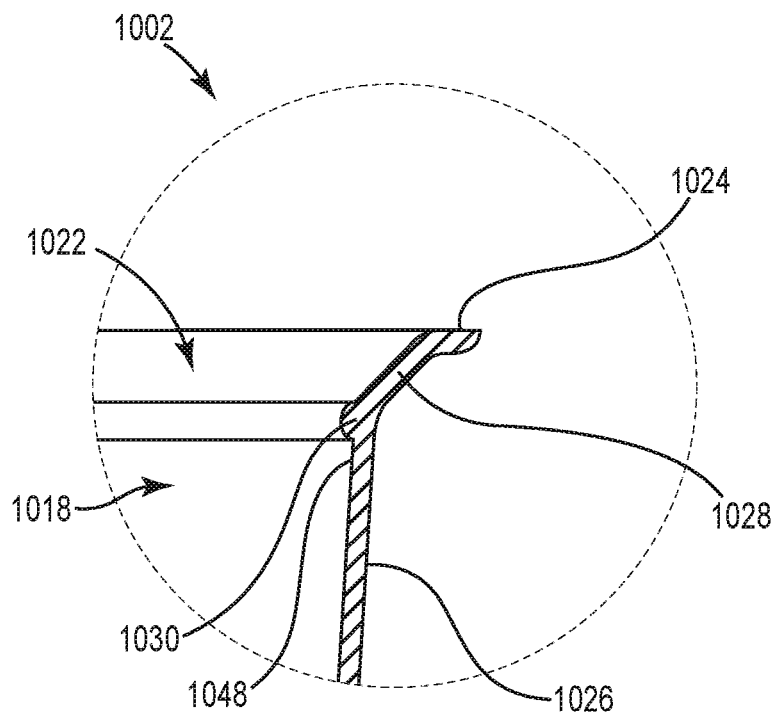
FIG. 27 is an enlarged cross-sectional view of the housing of FIG. 25.

FIG. 26 is a cross-sectional view showing the housing 1002 of FIG. 25 in greater detail. As can be further seen in FIG. 26, the housing 1002 includes a first (i.e., lower section) section 1016 and a second (i.e., upper) section 1018. The first housing section 1016 is closed-ended, and in some embodiments includes a raised portion 1020 that forms a pedestal or base that engages one end of the sterilizing element 1004 to secure it to the housing 1002. In some embodiments, the raised portion 1020 provides a frangible securement between the housing 1002 and the sterilizing element 1004, so that the sterilizing element can be easily disengaged from raised portion 1020 and removed from the housing 1002. The second housing section 1018, in turn, is tapered or flared slightly to conform to a portion of the cap 1006, and includes an opening configured to receive the working end-site of the device to be sterilized. In some embodiments, and as can be further seen in an enlarged view in FIG. 27, the second housing section 1018 includes an upper flange or lip 1024 that extends outwardly from the housing sidewall 1026. From the flange or lip 1024, the housing sidewall 1026 may taper inwardly along a tapered section 1028 to a interference member or detent 1030 that extends inwardly into the interior space 1010 of the housing 1002. In some embodiments, for example, the interference detent 1030 comprises an annular-shaped portion of the housing sidewall 1026 that extends radially into the interior space 1010 of the housing 1002, and which is configured to contact and frictionally engage, or mate with, a corresponding interfering member or indent or groove 1042 (FIG. 28) on an interior portion of the cap 1006, as discussed further herein. In certain embodiments, the detent 1030 is located on the inside housing sidewall 1026 between about 0.025 inches to 0.075 inches, and more specifically, about 0.50 inches, below the flange or lip 1024.

The upper housing section 1018, including the flange or lip 1024 and the tapered wall section 1028, are sized and shaped to conformingly receive the cap 1006, forming a hermetic seal that maintains the sterilizing element 1004 in a moist state, and which prevents external moisture, debris, and other contaminants from coming into contact with the interior surfaces of the housing 1002 and the sterilizing element 1004 prior to use. The housing 1002 is sized and shaped to receive the working end-site of a medical device. In some embodiments, the housing 1002 is configured such that the working end-site can be inserted, either into the interior space 1010 of the housing 1002 and/or the interior space of the sterilizing element 1004 that is situated within the housing 1002, to a depth of approximately 11 mm. In other embodiments, the housing 1002 is configured such that the working end-site can be inserted, either into the interior space 1010 of the housing 1002 and/or the interior space of the sterilizing element 1004 that is situated within the housing 1002, to a depth of about 3 mm to about 7 mm. In yet another embodiment, the housing 1002 is configured such that the working end-site can be inserted, either into the interior space 1010 of the housing 1002 and/or the interior space of the sterilizing element 1004 that is situated within the housing 1002, to a depth of approximately 3 mm.

The housing opening 1022 is of sufficient in size to permit the working end-site of the device to be inserted into the interior space 1010 of the housing 1002 during use. In some embodiments, the opening 1022 is also of sufficient size to permit the sterilizing element 1004 to be inserted into the interior space 1010 during the assembly process. In one embodiment, the opening 1022 is about 0.60 inches in diameter at or near the flange or lip 1024, and reduces in diameter to about 0.46 inches at the inner-most portion of the detent 1030.

The housing 1002 can be made from a variety of materials. According to some embodiments, the housing 1002 is made from a plastic, laminated paper/foil combination, or other semi-rigid material or semi-flexible material. In some embodiments, the housing 1002 is made from a first, relatively flexible material whereas the cap 1006 is made from a second, relatively rigid or stiff material. In one embodiment, for example, the housing 1002 can be made from polypropylene (PP) whereas the cap 1006 is made from a relatively rigid polymer (e.g., high-density polyethylene (HDPE)) or a metal (e.g., a medical grade stainless steel). In some embodiments, the housing 1002 and cap 1006 are formed from the same material, and the thickness of the housing sidewall 1026 is made sufficiently thin such that the sidewall 1026 is configured to bend or flex inwardly when squeezed laterally by the user's fingers. The cap 1006 may be thicker (more rigid) relative to the housing sidewall 1026, and the differential between the two thicknesses (that of the sidewall 1026 and cap 1006) provides a progressive slipping when the lateral sides are squeezed, according to embodiments of the present invention. In this way, the structure of the cap 1006 and/or material out of which cap 1006 is constructed is stronger and less flexible such that it undergoes a smaller displacement for a given squeezing or pinching force than the housing sidewall 1026, thereby promoting the progressive slipping and actuation of the cap 1006 from the housing sidewall 1026. In one embodiment, for example, the housing 1002 comprises a polypropylene material having a thickness of between about 0.006 inches to 0.018 inches, and more specifically, about 0.012 inches.

According to some embodiments, the housing 1002 is small and ergonomically shaped so as to be easily held within the fingers of one hand of the user. In certain embodiments, the housing 1002 is configured to be opened single-handedly using the fingers on one hand. Additionally, the housing 1002 can have a general shape such as an hour-glass or flared shape that guides the placement of a user's fingers. In some embodiments, the housing 1002 can include one or more finger locating features to guide a user's placement of their fingers when using the device 1000, and to facilitate gripping and handling of the device 1000. The finger locating features can include but are not limited to dimples, bumps, grip marks, and the like. Such locating features aid the user in finding the ideal location on the housing 1002 to squeeze and actuate the cap 1006 to release and audibly "pop" off from the housing 1002. In some embodiments, the housing 1002 is configured to be opened single-handedly using one or more fingers or thumb of one hand, by pressing the housing 1002 against another surface or object.

Figure 28:
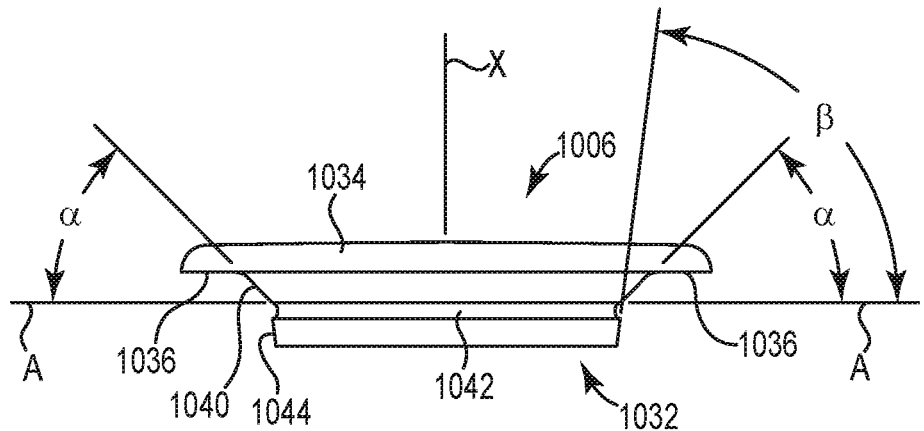
FIG. 28 is a perspective view showing the cap of FIG. 25 in greater detail.

FIG. 28 is a front elevation view showing the cap 1006 of FIG. 25 in greater detail. As can be further seen in FIG. 28, the cap 1006 includes an upper, flanged portion 1034 having a lower surface 1036 configured to contact and conformingly engage the flange or lip 1024 on the upper section 1018 of the housing 1002, and an annular-shaped skirt 1032 that extends vertically below the upper flanged portion 1034. As can be further seen in conjunction with the cross-sectional view of FIG. 29, the cap 1006 further includes an interior space 1038, which, in some embodiments, provides clearance for an upper portion of the sterilizing element 1004 to fit within a portion of the cap 1006.

Figure 29:
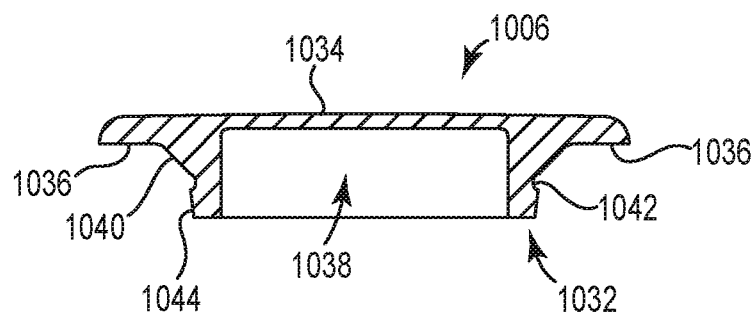
FIG. 29 is a cross-sectional view of the cap of FIG. 25.

As further shown in conjunction with FIGS. 28-29, the annular-shaped skirt 1032 includes a first tapered section 1040 that extends vertically downward at an angle $\alpha$ relative to a transverse axis A of the cap 1006. In some embodiments, the angle $\alpha$ of the tapered section 1040 is between about 30° to 60°, and more specifically, about 45°. When the cap 1006 is fully secured to or engaged with the housing 1002 prior to use, the tapered section 1040 is configured to contact and conformingly engage section 1028 on the housing 1002, which is similarly tapered. The annular-shaped skirt 1032 may also include a second tapered section 1044 that extends vertically downward at an angle $\beta$ relative to a transverse axis A of the cap 1006. In some embodiments, the angle $\beta$ of the tapered section 1044 is about 60° to 90° (or about 0° to 30° as measured from the longitudinal axis X), and more specifically, about 80°.

A circumferential interfering indent or groove 1042 inset within the skirt 1032 is configured to contact, mate with, and frictionally receive the interfering detent 1030 on the housing 1002, which further serves to secure the cap 1006 in place to the housing 1002 prior to use. In some embodiments, for example, the innermost dimension (e.g. an inner diameter) of the detent 1030 is slightly smaller than the outermost dimension (e.g. outer diameter within the indent 1042) of the indent or groove 1042, forming a slight friction or interference fit between the detent 1030 and the indent or groove 1042. During removal of the cap 1006, the relative motion of the detent 1030 relative to the indent or groove 1042 as the detent 1030 disengages from within the indent or groove 1042 creates a popping sound that provides the user with audible feedback that the seal between the cap 1006 and housing 1002 has been broken, and signifying that the device is open. The presence of the detent 1030 and indent or groove 1042 also serves to impart a slight delay between the time the user engages the housing 1002 with their fingers and when the cap 1006 is released from from the upper section 1018 of the housing 1002, according to embodiments of the present invention.

In some embodiments, the skirt 1032 further includes a lower section 1044 that extends vertically downward from the indent or groove 1042. As with the first tapered section 1040, the second section 1044 is configured to contact and conformingly engage a portion of the inside housing sidewall 1026, and, more specifically, the inside wall surface 1048. In some embodiments, the lower section 1044 may have a tapered shape that conforms to the shape of the housing 1002, which serves to further seal the cap 1006 to the housing 1002. In one embodiment, the reduced thickness of the lower section 1044 imparts additional flexibility to the skirt 1032 below the location of the detent 1030, which, in turn, allows the skirt 1032 to displace inwardly a short distance as the detent 1030 is disengaged from within the indent or groove 1042. Additionally, in some embodiments, the annular detent 1030 is absent from the inner housing 1026 and only an edge is sufficient to catch and interfere with the indent 1042 of the cap 1006 momentarily and delay the release of the cap 1006 when the housing 1002 is squeezed or pinched to create an audible popping sound, which also indicates that the sterilizing device is open.

The relationship between the surfaces of the skirt 1032 (e.g. 1036, 1040, 1044) and the corresponding surfaces 1024, 1028, 1048 on the upper section 1018 of the housing 1002 affect the degree of lift and release of the cap 1006 away from the housing 1002. For example, with respect to surface 1040, a greater angle α of taper causes the cap 1006 to lift off more towards one side of the housing 1002 when the housing 1002 is squeezed or pinched, whereas an even larger angle α, or alternatively an angle α of 90°, causes the cap 1006 to lift off from the housing 1002 more uniformly when the housing 1002 is pinched. A similar phenomenon is observed with the angle β formed between the surface 1044 and the transverse axis A, as such angle is increased, according to embodiments of the present invention. In some embodiments, the surface 1044 of the annular skirt 1032 is flared beyond 90°; for example, angle β may be 95° or 100°.

Figure 30:
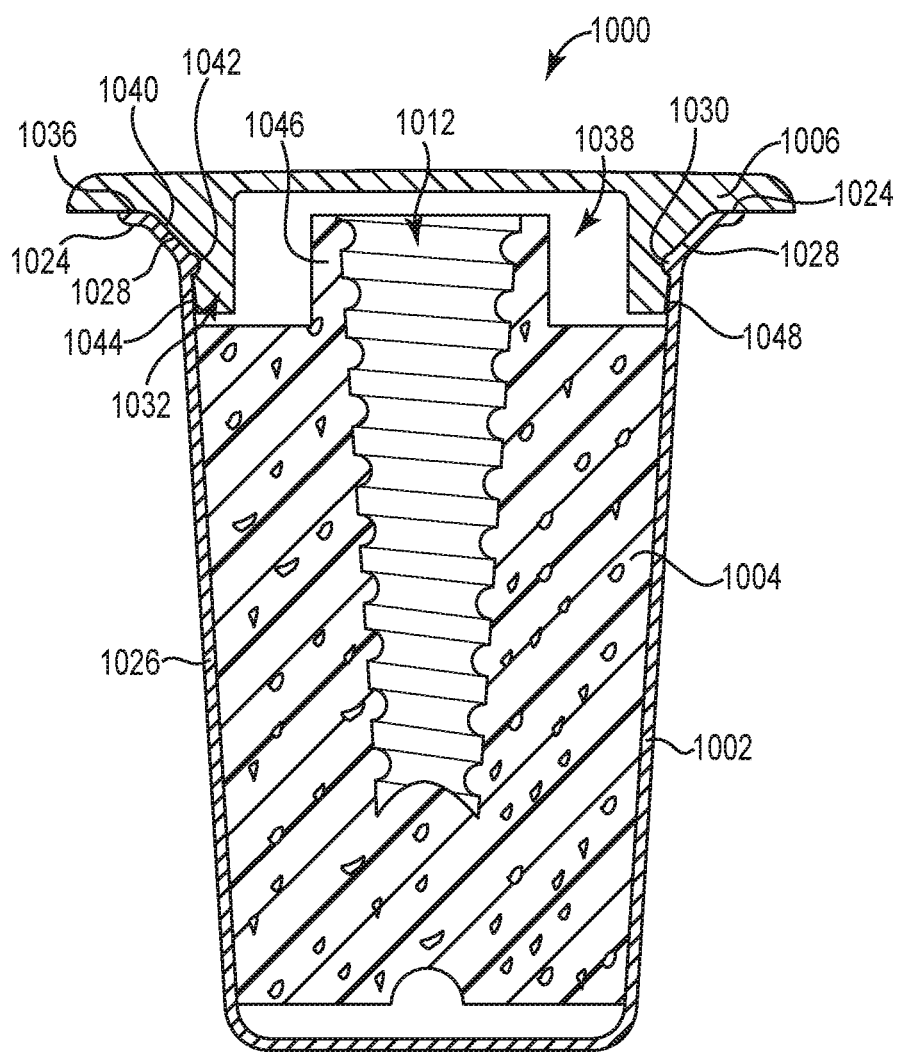
FIG. 30 is a partial cross-sectional view of the sterilizing device of FIG. 25, showing the cap fully secured to the housing.

FIG. 30 is a partial cross-sectional view showing the cap 1006 fully secured to the housing 1002. As shown in FIG. 30, and in some embodiments, the interior space 1038 within the interior of the cap 1006 is configured to provide a clearance for an upwardly extending portion 1046 of the sterilizing element 1004. This clearance serves to reduce the overall size of the sterilizing device 1000, and in some embodiments also serves as an additional reservoir for storing an amount antipathogenic agent. In certain embodiments, the interior space 1038 between the cap 1006 and the sterilizing element 1004 can be pressurized with an inert gas (e.g., nitrogen) to pressurize the interior of the housing 1002. In some embodiments, the elevated extending portion 1046 is configured to disinfect a male luer lock and its respective shroud and slip-luer aspects. In some embodiments the extending portion 1046 has external contours (not shown) to disinfect the shroud portion and respective internal threading such as on the male luer lock. Such external contours also provide a mechanism to secure the device 1000 onto an end-site such as a male luer lock. The extending portion 1046 provides additional space along with interior space 1038 to provide clearance for an end-site with a shroud such as male luer lock without interfering with the inside housing 1002 and the base sterilizing element 1004, especially during a vigorous twisting and turning.

As further shown in FIG. 30, the lower surface 1036 of the upper, flanged portion 1034 of the cap 1006 is configured to contact and conformingly engage with the flange or lip 1024 on the upper section 1018 of the housing 1002. In similar fashion, sections 1040 and 1044 of the annular skirt 1032 are configured to contact and conformingly engage sections 1028, 1048 of the housing 1002, respectively. When fully engaged to the housing 1002, the detent 1030 is configured to snap-fit within the circumferential indent or groove 1042 on the cap 1006, providing a friction or interference fit between the housing 1002 and cap 1006. This further serves to hermetically seal the housing 1002, and prevents an inadvertent release of the cap 1006 prior to use. In some embodiments, adhesive or sealants are used on a combination of surfaces 1036 and in combination with 1024 to provide a hermetic seal. In some embodiments, a medical grade coating can be applied such as a parylene, silicone or similar such coating to provide the hermetic seal as well as reduce the friction between the annular skirt 1032 and the sections 1040, 1042 and 1044 housing upper sections 1018 and surfaces of 1028, 1030 and 1048 to provide an efficient progressive slipping and actuation of the cap 1006 and annular skirt 1032 away from housing 1002 and surfaces in upper sections 1018. According to some embodiments of the present invention, the detent 1030 is not included on the housing 1002. According to some embodiments, the detent 1030 is included, but is not continuous about an entire inner perimeter of the housing 1002.

Figure 31:
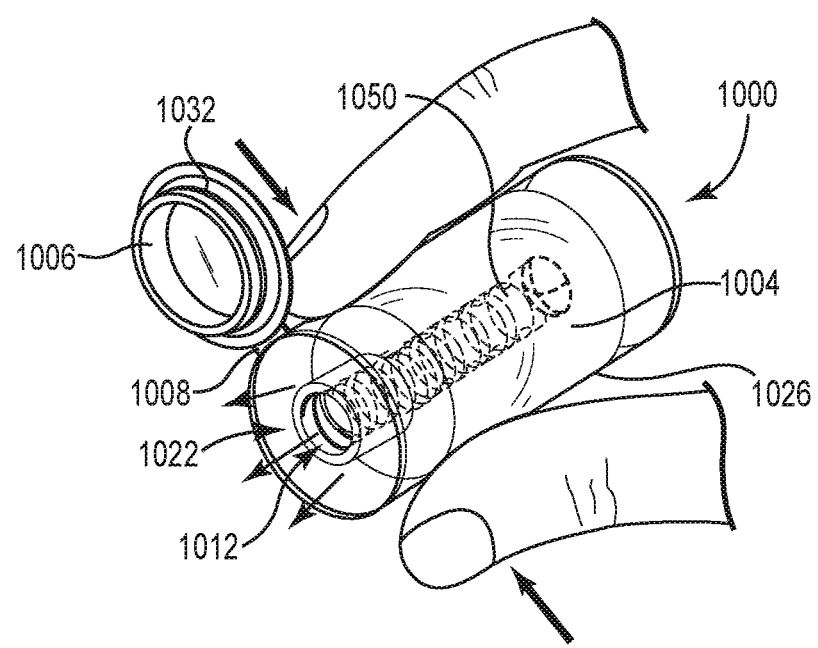
FIG. 31 is another view of the sterilization device of FIG. 25, showing the removal of the cap from the housing.

FIG. 31 is another view of the sterilization device 1000 of FIG. 25, showing the removal of the cap 1006 from the housing 1002. To release the cap 1006 from the housing 1002, the user squeezes the sidewalls 1026 of the housing 1002 together with his or her fingers. As this occurs, pressure exerted on the housing sidewalls 1026 by the user's fingers causes the sidewalls 1026 to displace radially inward at the point of finger contact, increasing the interior pressure within the housing interior space 1010. Since the annular skirt 1032 on the cap 1006 is relatively rigid in comparison to the housing sidewalls 1026, this inward pressure on the sidewalls 1026 causes the upper section 1018 of the housing 1002 to displace outwardly relative to the annular skirt 1032. This displacement in combination with the increased pneumatic pressure within the interior space 1010 of the housing 1002 and the tapered surfaces 1040, 1044 of the skirt 1032 results in a progressive slipping motion between the skirt 1032 and the housing 1002, causing the detent 1030 to disengage from within the indent or groove 1042 and the cap 1006 to lift off of the housing 1002. An audible, popping sound caused by the release of the cap 1006 from the housing 1002 provides the user with feedback that the seal between the cap 1006 and the housing 1002 has been broken and that the device is open. In some embodiments, the cap 1006 with an annular skirt 1032 is secured to the housing's 1002 exterior sidewall having the same detachable and securing characteristics as described above and a progressive slip when the lateral sidewalls 1026 are squeezed and audibly pop off the cap 1006. In some embodiments, a gas located within interior 1010/1012 of the housing 1002 may also change color to indicate that the seal between the cap 1006 and the housing 1002 has been broken. In some embodiments, the combination of the cap 1006 and housing 1002 visually indicates that the seal has been broken. In some embodiments one or both of the cap 1006 and housing 1002 is transparent or translucent allowing the user to visually see whether the device's 1000 seal has been compromised by a visual indicator that can be viewed through the cap 1006 and/or housing as either a color change, or as a recognition pattern that appears, or appears displaced such as two lines that are now visible where only one line appeared before; or whereby the lines appear offset from each other where they once were visibly aligned, indicating when the seal is broken. Other visual indicators can be used for this purpose to ensure that the interior space and sterilizing element 1004 remain sterile and hermetically sealed.

Once released, the cap 1006 is configured to displace outwardly away from the opening 1022, allowing the user to insert the working end-site of a medical device into the sterilizing element 1004. In some embodiments, the tether 1008 serves to hingedly connect the cap 1006 to the housing 1002, preventing the cap 1006 from detaching or separating from the housing 1002, once opened. In one embodiment, the tether 1008 can have a spring memory that biases the cap 1006 in the open position away from the housing opening 1022. Once fully opened, a clip, fastener, or the like may be used to secure the cap 1006 in place to the outer surface of the housing 1002, if desired. In some embodiments, the tether 1008 includes an inference piece in combination with the cap 1006 that holds the cap 1006 away from the housing opening 1022. Additionally, the interference piece may be on the housing 1026 and on the exterior portion on the upper housing 1018 and, in combination with the tether 1008, prevents and holds the cap 1006 away from the housing opening 1022. In some embodiments, the cap 1006 is permanently secured to the housing 1002 via the tether 1008. In other embodiments, the tether 1008 includes a tear-line or frangible joint that facilitates removal of the cap 1006 from the housing 1002. The tether 1008 can be formed from a plastic, metal, or metal-plastic composite. In one embodiment, for example, the tether 1008 comprises a metal wire encased in a polymeric sleeve. In one embodiment, the tether is contained within and on the inside surfaces of the sterilizing device 1000. The tether may be secured to an inside surface of both the housing 1002 and an inside surface of the cap 1006 and enclosed within the sterilizing device 1000, according to embodiments of the present invention.

Once the housing 1002 has been opened, the working end-site of the device to be sterilized may be inserted through the housing opening 1022 to access the sterilizing element 1004. In some embodiments, the end-site is inserted into an interior portion 1050 of the sterilizing element 1004 such that the sterilizing element 1004 contours to the outer threads, edges, sides, and inner lumen surfaces of the end-site.

As with other embodiments, debris is cleared from, and an inclusive layer of antipathogenic agent is applied to, the end surfaces of the working end-site with the contoured sterilizing element 1004 using a wiping and/or twisting motion for sufficient amount of time so as to achieve a specific "kill of microbes." According to some embodiments, cleaning and sterilizing the working end-site includes expelling the antipathogenic agent onto the working end-site. For example, in one embodiment, the working end-site is compressed into the sterilizing element 1004 to expel the antipathogenic agent from the element 1004 and onto the working end-site. In another exemplary embodiment, the antipathogenic agent can be expelled onto the working end-site by squeezing the sidewall 1026 of the housing 1002 to compress the sterilizing element 1004 contained therein to expel the antipathogenic agent onto the working end-site. In another embodiment, the antipathogenic agent can be expelled by squeezing the sidewall 1026 of the housing 1002 to compress the sterilizing element 1004 contained therein to expel the antipathogenic agent prior to contacting the working end-site. In some embodiments, the sterilizing device 1000 may be left engaged with the working end-site until ready for use.

Once the working end-site has been cleaned and sterilized for the appropriate amount of time, the working end-site then can be removed from the sterilizing element 1004 and the housing 1002, and allowed to air dry prior to connection of another compatible device or an injection made therein with a syringe.

Figure 32:
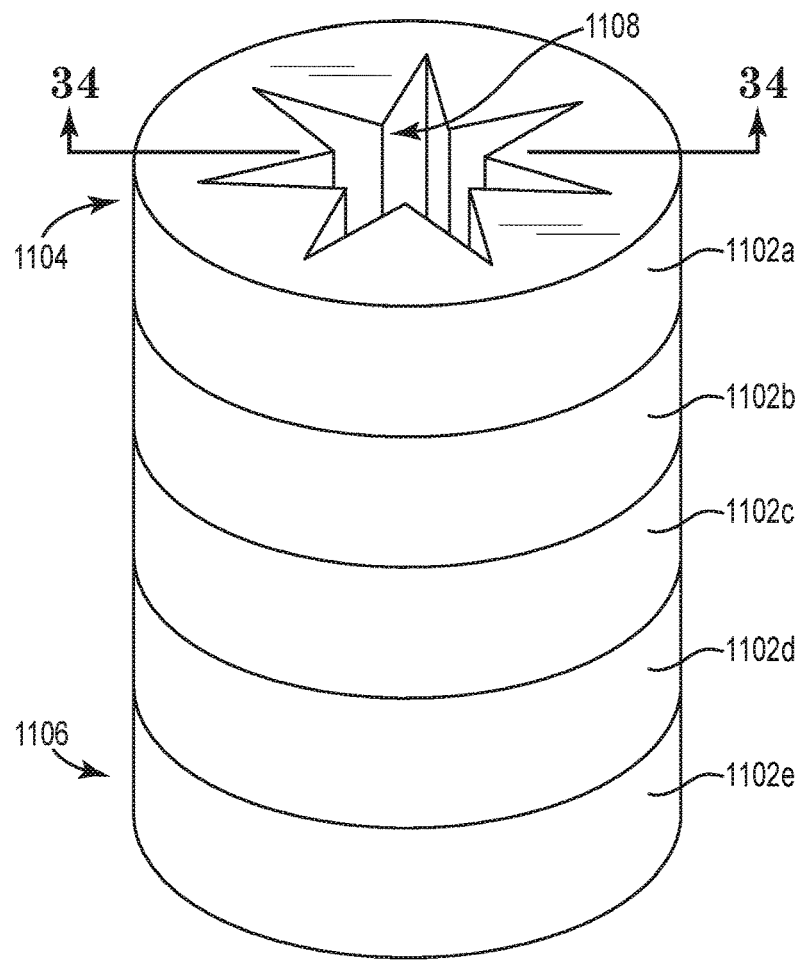
FIG. 32 is a perspective view showing a sterilization element in accordance with another illustrative embodiment.

FIG. 32 is a perspective view showing a sterilization element 1100 in accordance with another illustrative embodiment. As shown in FIG. 32, the sterilizing element 1100 comprises a plurality of cylindrically-shaped foam members 1102*a*, 1102*b*, 1102*c*, 1102*d*, 1102*e* stacked endwise on top of each other, forming a substantially cylindrical shaped structure having an upper section 1104 and a lower section 1106. A substantially solid foam member 1102*e* is closed-ended, and forms a base of the sterilizing element 1004. The upper section 1104 of the sterilizing element 1004 includes a star-shaped opening 1108 configured to receive the working end-site of a device to be sterilized. Although five foam members 1102*a*, 1102*b*, 1102*c*, 1102*d*, 1102*e* are shown, a greater or lesser number of foam members may form the sterilizing element 1100.

Figure 33:
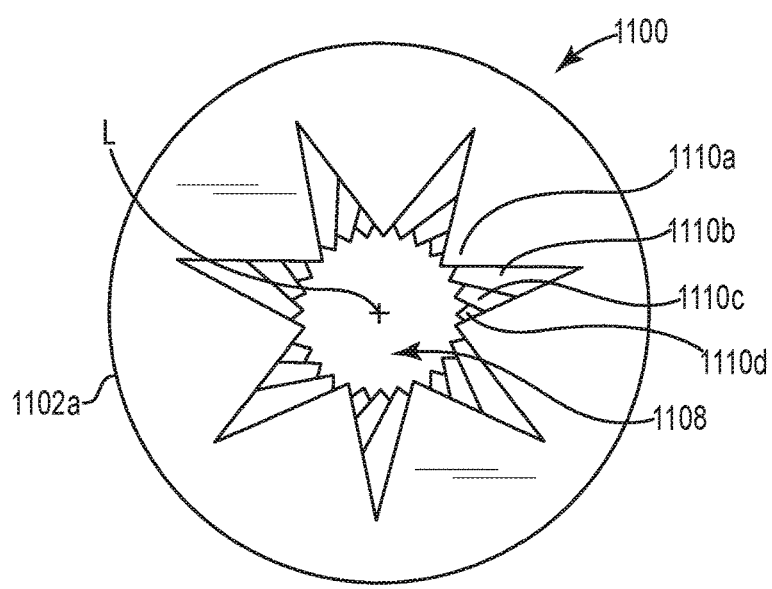
FIG. 33 is a top view of the sterilizing element of FIG. 32.
Figure 34:
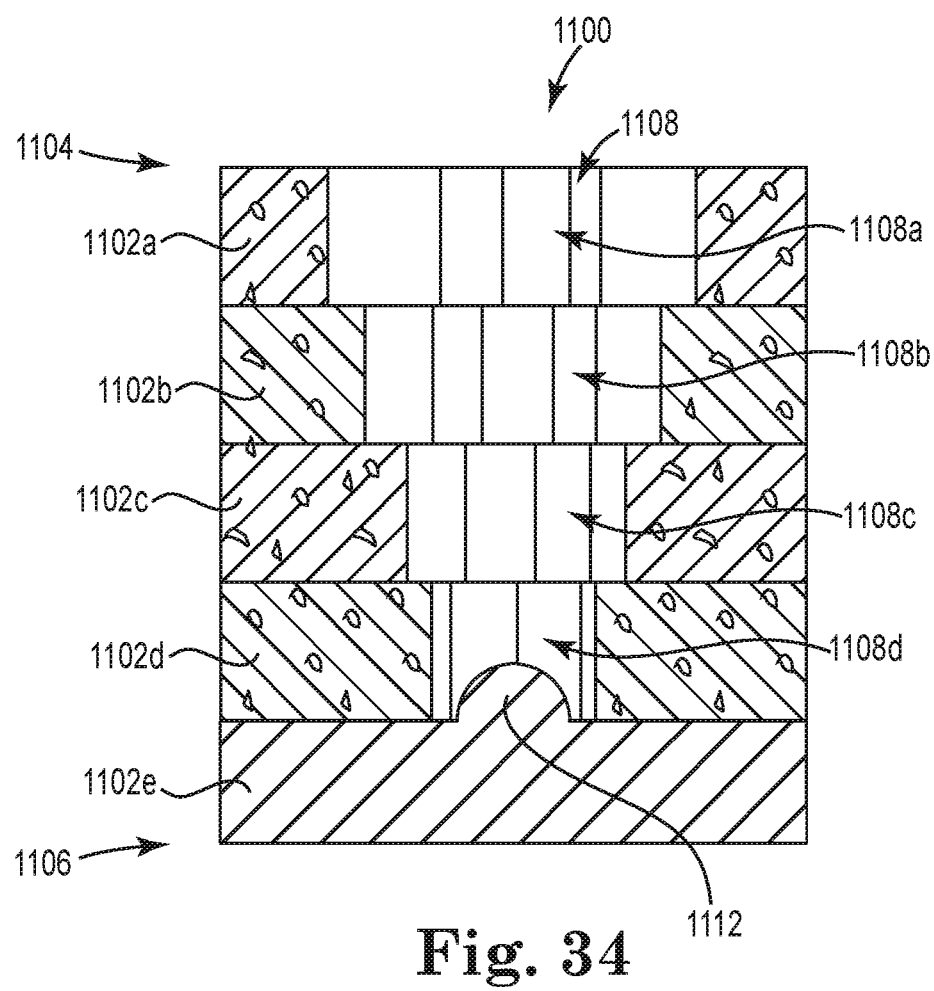
FIG. 34 is a cross-sectional view of the sterilizing element of FIG. 32 along line 34-34 in FIG. 32.

FIG. 33 is a top view of the sterilizing element 1100 of FIG. 32. FIG. 34, in turn, is a cross-sectional view of the sterilizing element 1100 taken along line 34-34 in FIG. 32. As can be further seen in FIGS. 33 and 34, each foam member 1102*a*, 1102*b*, 1102*c*, 1102*d* includes a corresponding star-shaped opening 1108*a*, 1108*b*, 1108*c*, 1108*d*. The opening 1108*a*, 1108*b*, 1108*c*, 1108*d* for each individual foam member 1102*a*, 1102*b*, 1102*c*, 1102*d* is formed by a plurality of inwardly-projecting members 1110*a*, 1110*b*, 1110*c*, 1100*d* on each member 1102*a*, 1102*b*, 1102*c*, 1102*d* to create a highly detailed contoured opening. In some embodiments, and as further shown in FIG. 34, the base foam member 1102*e* includes an upwardly extending nub 1112 configured to clean a lumen, septum, or other internal or terminal feature or features of the working end-site of the device. In some embodiments, the base member 1102*e* includes more complex or varied contours having multiple raised aspects and textures. In some embodiments, the base member 1102*a* has a plurality of upwardly extending nubs 1112 that are spaced and configured to compress and to conform to a terminal end-site such as a septum. In some embodiments, the base member 1102*e* is materially different from the individual foam members and softer or more compliant. In some embodiments the base member 1102*e* is firmer and less compliant than the individual foam members. In some embodiments, the base member 1102*e* has a contoured surface corresponding to the terminal end-site on the medical device. The terminal end-site (not shown) may include a distinct configuration according to which the base member 1102*e* contours purposefully to efficiently to reduce the time and increase the accuracy of sterilizing the terminal end-site. In some embodiments, the base member 1102*e* has material properties that are malleable and resilient, and the base member 1102*e* may be sculpted and contoured to conform while being physically manipulated around the terminal end-site.

The inwardly-projecting members 1110*a*, 1110*b*, 1110*c*, 1110*d* on each foam member 1102*a*, 1102*b*, 1102*c*, 1102*d* are circumferentially spaced at equidistant intervals from each other (e.g., 45°) about a longitudinal axis of the sterilizing element 1100. In certain embodiments, and as best shown in FIG. 33, the inwardly-projecting member 1110*a*, 1110*b*, 1110*c*, 1110*d* for each foam member 1102*a*, 1102*b*, 1102*c*, 1102*d* can be rotationally offset (about the longitudinal axis) from the inwardly-projecting members 1110*a*, 1110*b*, 1110*c*, 1110*d* of an adjacent foam member 1102*a*, 1102*b*, 1102*c*, 1102*d* such that the location of the members 1110*a*, 1110*b*, 1110*c*, 1110*d* vary along the depth of the sterilizing element 1100. For a sterilizing element comprising four foam members 1102*a*, 1102*b*, 1102*c*, 1102*d* each having seven inwardly-projecting members 1110*a*, 1110*b*, 1110*c*, 1110*d*, for example, the inwardly projecting member 1110*a*, 1110*b*, 1110*c*, 1110*d* for each foam member (e.g., member 1102*a*) can be rotationally offset from a vertically adjacent foam member (e.g., foam member 1102*b*) by approximately 22.5°. This radial or rotational offset between each vertically-adjacent foam member 1102*a*, 1102*b*, 1102*c*, 1102*d* forms a highly textured inside contoured opening that contours along with a contoured base member 1102*e* to create a highly detailed contoured cavity, and better engages, the cracks and crevices on the working end-site. The amount of offset between the inwardly projecting members can vary depending on the number of foam members that are stacked together as well as the number of inwardly projecting members for each foam member. In some embodiments each foam member may vary in depth about the longitudinal axis (more proximal or more distal relative to the longitudinal axis), and/or each individual inwardly-projecting member may vary to provide a highly contouring sterilizing element. In additional embodiments, the cylindrically-shaped members are concentric and share the same longitudinal axis but have a different internal radial dimensions (e.g. different innermost diameters) and progressively taper inward and down from the housing opening and narrow towards the contoured base. According to some embodiments, the cylindrical-shaped members have adjacent members which vary in pattern from member to member, and/or have adjacent members whose inwardly projecting members have a dissimilar patterns, and/or are offset from adjacent members to thus stagger the contact surface and/or maximize a detail contoured cavity. In some embodiments, each member may have an outer surface and contours (not shown) on the outside surface and whereby the contours of the combined members match and form-fit and are adapted to generally complement or otherwise engage the inside surfaces of a medical device end-site to be sterilized. For example, the outside contours can be any one or more of ribs, threads, steps, flanges, points, raised structures that contours to match the inside surface as on an end-site, for example that of a male luer shroud.

According to some embodiments, the sterilizing element 1000 can be fabricated by individually forming a number of identical foam members 1102a, 1102b, 1102c, 1102d as separate elements, and then joining the foam members 1102a, 1102b, 1102c, 1102d together to each other and to the base member 1102e via adhesive, thermal bonding, or other suitable joining technique. In certain embodiments, for example, the foam members 1102a, 1102b, 1102c, 1102d can each be formed individually via an insert molding or extrusion process, and are joined together to a base member 1102e in a staggered or offset manner using a medical grade adhesive and/or thermal bonding. Once assembled together and joined, the sterilizing element 1000 can then be secured to the housing.

Figure 35:
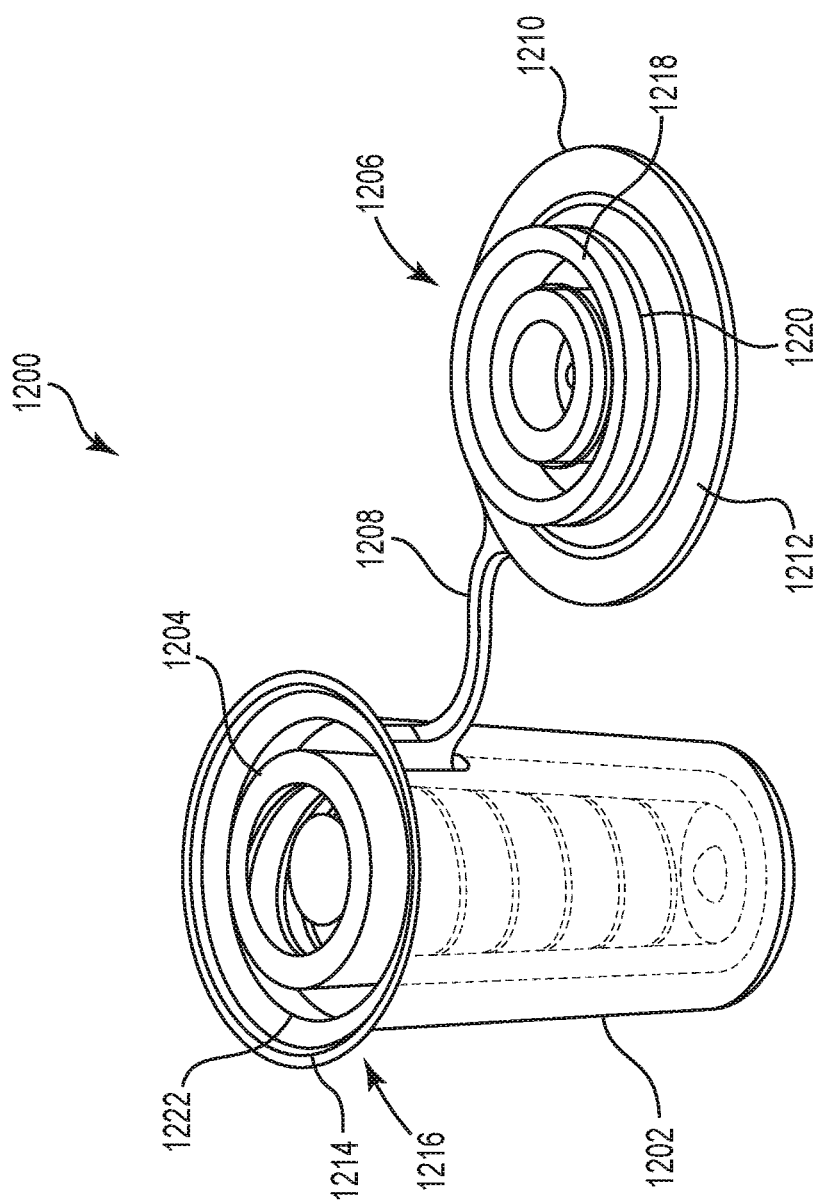
FIG. 35 is an isometric view of a sterilization device in accordance with another illustrative embodiment.

FIG. 35 is an isometric view of a sterilization device 1200 in accordance with another illustrative embodiment. In the embodiment of FIG. 35, the sterilization device 1200 includes a housing 1202 containing a first contoured sterilization element 1204, and a cap 1206 that is releasably secured to the housing 1202. In some embodiments, and as shown in FIG. 35, the cap 1206 is permanently secured to housing 1202 via a tether 1208. The tether 1208 can comprise, for example, a flexible hinge (e.g., a living hinge), wire, strap, or other suitable connecting member coupled to or formed integrally with the cap 1206 and/or housing 1202. In other embodiments, the cap 1206 is initially secured to the housing 1202, but is configured such that the cap 1206 can be easily removed from the housing 1202 in preparation for sterilizing the working end-site of a medical device. As is discussed in greater detail herein, and in some embodiments, the cap 1206 is configured to lift-off and disengage from the housing 1202 in response to a sufficient lateral pressure asserted against the sides of the housing 1202 by the user's fingers.

The housing and 1202 and first sterilizing element 1204 can be configured similar to the housing 1002 and sterilizing element 1004 of FIG. 25. In certain embodiments, for example, the first sterilizing element 1204 includes an absorbent foam article containing an antipathogenic agent and having a contoured shape configured to form-fit over the working end-site of a medical device for efficient wiping and sterilization. The cap 1206 can also be configured similar to the cap 1006 of FIG. 25, including a upper, flanged portion 1210 having a lower surface 1212 configured to contact and conformingly engage a flange or lip 1214 on an upper section 1216 of the housing 1202, and an annular-shaped skirt 1218 that extends vertically below the upper flanged portion 1210. A circumferential indent or groove 1220 inset within the skirt 1218 is configured to contact and frictionally receive a detent 1222 on the housing 1202, forming a slight friction or interference fit between the detent 1222 and the indent or groove 1220 that serves to seal the cap 1206 to the housing 1202. One or more other features such as the presence of mating tapered surfaces on the annular-shaped skirt 1218 and upper section 1216 of the housing 1202 can also be used to further seal the cap 1206 to the housing 1202.

Figure 36:
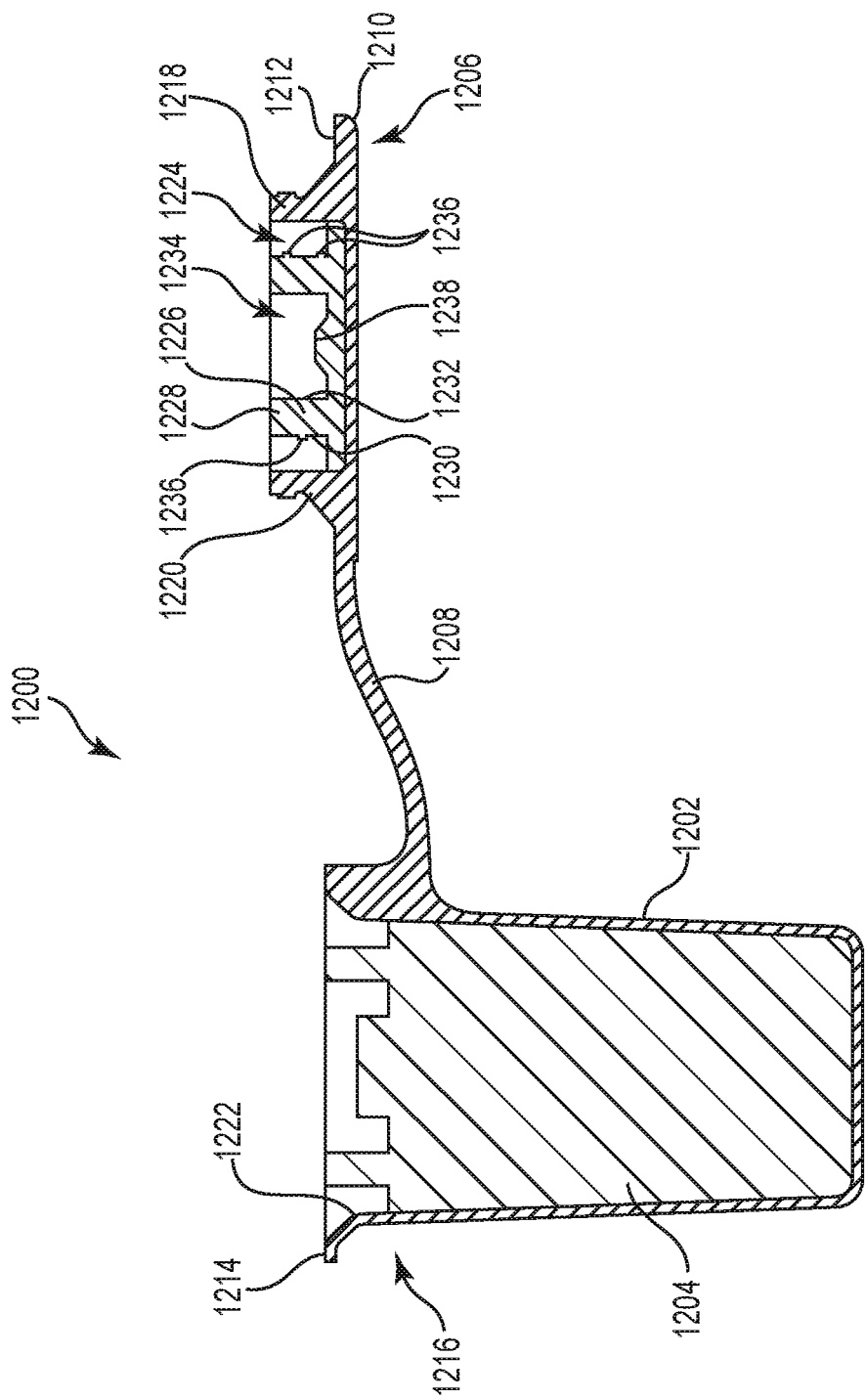
FIG. 36 is a cross-sectional view of the sterilization device of FIG. 35, showing the cap in a detached position from the housing.

FIG. 36 is a cross-sectional view of the sterilization device 1200 of FIG. 35, showing the cap 1206 detached from the housing 1202. As can be further seen in FIG. 36, the cap 1206 further includes an interior space 1224, which in some embodiments provides clearance for a portion of the first sterilizing element 1204 to fit within the interior space 1224 of the cap 1206. In the embodiment shown, the interior space 1224 of the cap 1206 is further configured to receive a second sterilizing element 1226, which similar to the first sterilizing element 1204, can be used to wipe and sterilize the working end-site of a medical device. In certain embodiments, for example, the second sterilizing element 1226 within the cap 1206 can be used for sterilizing the working end-site of a male luer connector whereas the first sterilizing element 1204 within the housing 1202 can be used for sterilizing the working end-site of a female luer connector. In an alternative embodiment, the second sterilizing element 1226 can be used for sterilizing the working end-site of a female luer connector whereas the first sterilizing element 1204 can be used for sterilizing the working end-site of a male luer connector.

The second sterilizing element 1226 can be secured within the interior space 1224 of the cap 1206 to prevent dislodgement of the element 1226 from the working end-site of a device being sterilized. In some embodiments, the sterilizing element 1226 is secured within the cap 1206 such that it can withstand vigorous wiping of an end-site. The second sterilizing element 1226 can be secured within the cap 1206 by various methods including, but not limited to, ultrasonic welding, inward indentations of the walls, internal molded ribs or points, adhesives, frictional engagement, as well as the sterilizing element's own outward expanding radial force to hold it in place within the cap 1206. In some embodiments, the cap 1206 with a sterilizing element 1226 can be detached or removed from the tether 1208 and the entire cap 1206 with sterilizing element 1226 can be used to disinfect and sterilize the end-site and secured to the end-site until use. In some embodiments, the sterilizing element 1226 may be disengaged from the cap 1206 by twisting the cap 1206 to release the sterilizing element 1226 onto the end-site for direct attachment to and sterilizing of the end-site. In some embodiments the housing disengages the sterilizing element onto the medical device end-site and the housing is removed therefrom and the sterilizing element remains attached to the end-site. In certain embodiments, the cap 1206 and second sterilizing element 1226 can be formed from a single, unitary member. For example, in one embodiment the second sterilizing element 1226 comprises a porous polymeric material that can be integrally formed with the cap 1206 using an injection molding or insert molding process.

In some embodiments, the second sterilizing element 1226 may be removed from the cap 1206 for attachment to and sterilizing of the end-site, as well as be directly held by and in the hand of the user to sterilize the end-site. In certain embodiments, the sterilizing element 1226 has an inclusive layer of antipathogenic to sterilize both the working end-site and the user's fingers. In some embodiments, the sterilizing element 1226 is impregnated with a liquid antipathogenic agent that evaporates when attached to the end-site. In some embodiments the sterilizing element 1226 is removed from the cap 1206 and squeezed to expel the liquid antipathogenic from the impregnated sterilizing element 1226. In some embodiments, the sterilizing element 1226 is impregnated with a dry bonded antipathogenic agent that disinfects and sterilizes when left in place on the end-site. In some embodiments, the dry bonded agent is activated by combination of contact-pressure and friction when manipulated onto the end-site and by the users handling and fingers. According to some embodiments, the dry antipathogenic agent is bonded onto the sterilizing element 1226 as microparticles or nanoparticles, which are disrupted or activated, with a combination of contact-pressure and friction when attached to the end-site causing the surface of the sterilizing element 1226 to have disinfecting properties to sterilize the end-site. In some embodiments, the dry antipathogenic agent, bonded onto the sterilizing element 1226 as microparticles or nanoparticles, is activated or disrupted when the user's finger squeezes the sterilizing element 1226. Alternatively, the second sterilizing element 1226 may be left in place within the cap 1206 and the whole device 1200 can be left on the end-site for the purpose of protecting the site's sterility until such time as the device is removed so that the site end can be used. In some embodiments, the first sterilizing element 1204 may be removed from the housing 1202 for attachment to and sterilizing of the end-site, as well as be directly held by and in the hand of the user to sterilize the end-site. In certain embodiments, the sterilizing element 1204 has an inclusive layer of antipathogenic to sterilize both the working end-site and the user's fingers.

In some embodiments, the second sterilizing element 1226 can be pre-shaped or pre-molded such that it is configured to contour to the surfaces of the working end to be sterilized. For example, in some embodiments, the sterilizing element 1226 can be contoured and pre-shaped such that it is configured to form-fit over the working end-site of a medical connector, catheter hub, luer compatible connector, luer component, and/or needle access port for efficient wiping and sterilizing. In other embodiments, the sterilizing element 1226 can be shaped to contour to and engage an inner lumen, septum, port, and/or needleless injection site. In other embodiments, a micropatterned or microtextured surface on the sterilizing element 1226 provides an additional refinement to the sterilizing device for contacting and cleaning intricate details on an end-site such as cracks, crevices or grooves and where microscopic bacterium can reside on an end-site, and particularly, where an end-site has been assembled with multiple components having microscopic surfaces that can harbor bacterium (e.g., a needle-less connector having assembled components such as a housing, seals, valve or septum). The microtexturing or micropatterning can include any one of a number of ridges, bumps, surface roughing, rings, concentric circles, dimples, lattice features, and the like, and may be further defined as nano-texturing.

In the embodiment of FIG. 36, the second sterilizing element 1226 comprises an annular-shaped wall 1228 having an outer surface 1230 and inner surface 1232, and an interior space 1234. When configured for use with female-type connectors, and in some embodiments, the outer surface 1230 of the wall 1228 includes a set of threads 1236 that contact and engage the inside of a male luer shroud. An upwardly extending nub 1238 within the interior space 1234 of the second sterilizing element 1226 is configured to clean a lumen, septum, slip luer, or other internal feature of the working end-site of the device.

Figure 37:
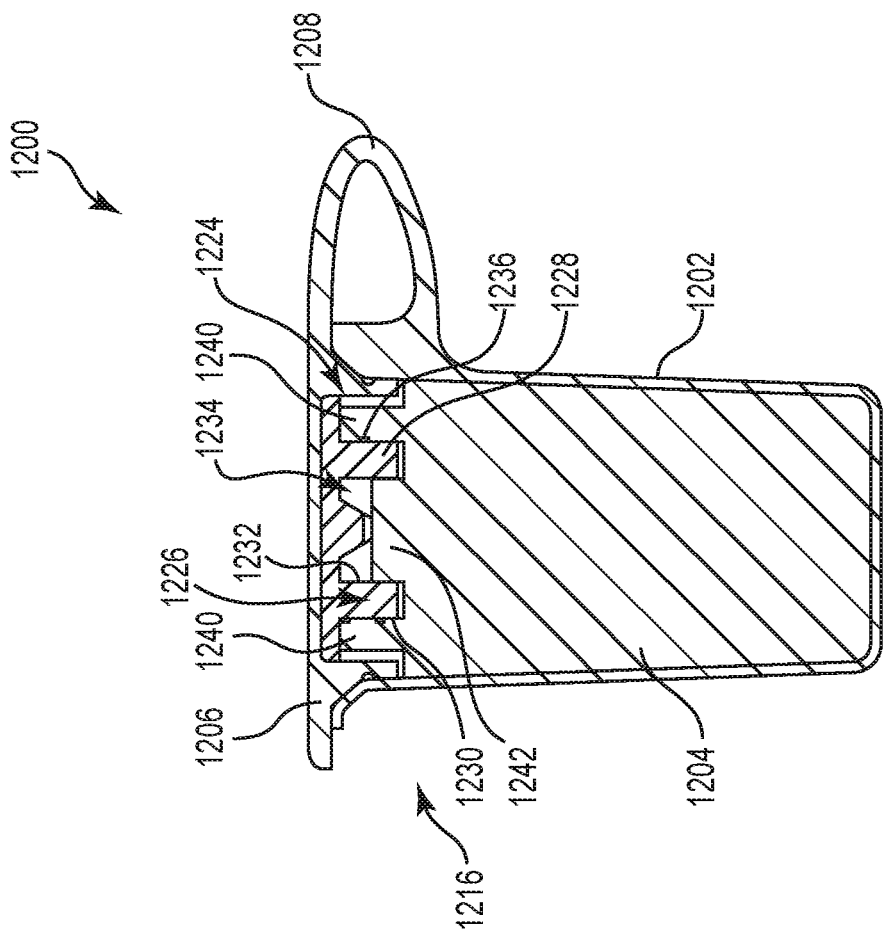
FIG. 37 is a cross-sectional view of the sterilization device of FIG. 35, showing the cap fully secured to the housing.

FIG. 37 is a cross-sectional view of the sterilization device 1200 of FIG. 35, showing the cap 1206 fully secured to the housing 1202. As shown in FIG. 37, and in some embodiments, the interior space 1224 within the interior of the cap 1206 is configured to provide a clearance for a first upwardly extending portion 1240 of the first sterilizing element 1204. The interior space 1234 within the second sterilizing element 1226, in turn, is configured to receive a second upwardly extending portion 1242 of the first sterilizing element 1204. When fully closed, and as can be seen in FIG. 37, the upwardly extending portions 1240, 1242 of the first sterilizing element 1204 are configured to contact and engage with portions of the second sterilizing element 1226, including the outer and inner surfaces 1230, 1232 of the wall 1228. In some embodiments, the first upwardly extending portion 1242 can also be configured to contact and engage with the nub 1238 located within the interior space 1234 of the second sterilizing element 1226. In some embodiments, the first and second sterilizing elements 1204, 1226 are configured to mate with each other such that, when brought together in the position shown in FIG. 37, the mating surfaces of both elements 1204, 1226 are in liquid communication with each other. This ensures that both elements 1204, 1226 remain pre-moistened or impregnated with the antipathogenic agent prior to use.

According to some embodiments of the present invention, the housing 1002 and cap 1006, and/or housing 1202 and cap 1206, combinations may be used independently, and/or independently of any sterilizing element. For example, such housing and cap combinations may be used in other applications which would benefit from a hermetic and/or sterile seal between housing and cap, and/or which would benefit from an arrangement whereby the housing may be squeezed or pinched to release the cap. Such embodiments include any and all features of the housing 1002 and cap 1006 (and housing 1202 and cap 1206) and their related features, as described herein.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A medical device to mate with a medical end-site having a lumen and a surface contour that includes a contour feature of at least one mating projection or at least one mating indentation, the medical device comprising:

an open end housing made of a first material and an element made of a second material different from the first material retained within the housing, the element having a form-fitting sidewall pre-shaped surface contour structure selected from the group consisting of a ridge, a thread and a flange for the medical end-site; whereby the sidewall pre-shaped surface contour structure of the element will frictionally contact and effect at least one of cleaning, disinfecting, sterilizing and drying of the contour feature of the medical end-site when the medical device is mated to the medical end-site.

2. The medical device of claim 1, wherein the contour structure is a mating projection.

3. The medical device of claim 1, wherein the contour structure is a mating indentation.

4. The medical device of claim 1, wherein the element defines a cavity and further wherein the element includes a mating projection extending into the cavity.

5. The medical device of claim 1, wherein the medical-end-site contour feature is selected from an outer thread, an edge, a side, and an inner surface defining the lumen.

6. The medical device of claim 1, wherein the form-fitting pre-shaped surface contour structure on the element has a point shape.

7. The medical device of claim 1, wherein the element further defines a raised base portion forming a surface selected from a nipple, a bump, a nub, and a tine.

8. The medical device of claim 1, wherein the element has a plurality of differently shaped form-fitting pre-shaped surface contour structures.

9. The medical device of claim 1, wherein the element is comprised of a semi-flexible material, a semi-rigid material, or a combination thereof.

10. The medical device of claim 1, wherein the element is at least one of malleable, resilient and elastic.

11. The medical device of claim 1, wherein at least a portion of the element is comprised of at least one of a non-woven, particulate-free, absorbent foam, a natural sponge and a synthetic sponge.

12. The medical device of claim 1, wherein the element has an optical characteristic selected from translucent and transparent.

13. The medical device of claim 4, further comprising an antipathogenic agent retained within the cavity.

14. The medical device of claim 13 wherein the element defines a cavity bounded by an interior surface, the form-fitting pre-shaped surface contour structure is located on the interior surface of the element, and the antipathogenic agent is a wet antipathogenic agent retained within the cavity whereby the antipathogenic agent wets the form-fitting pre-shaped surface contour structure on the element.

15. The medical device of claim 13 wherein the antipathogenic agent is a dry antipathogenic agent present on at least the form-fitting pre-shaped surface contour structure on the element.

16. The medical device of claim 13, wherein the antipathogenic agent is bonded to at least the form-fitting pre-shaped surface contour structure on the element.

17. The medical device of claim 13, wherein the antipathogenic agent is impregnated into at least the form-fitting pre-shaped surface contour structure on the element.

18. The medical device of claim 13, wherein the antipathogenic agent is an oligodynamic antipathogen.

19. The medical device of claim 13, wherein the antipathogenic agent is a dry bonded antipathogenic agent.

20. The medical device of claim 1, wherein the form-fitting pre-shaped surface contour structure on the element comprises a repeating pattern.

21. The medical device of claim 1, wherein the form-fitting pre-shaped surface contour structure on the element friction fits onto the surface of the medical end-site.

22. The medical device of claim 1, wherein a friction fit contributes to a structural retention of the element with the medical end-site.

23. The medical device of claim 1, wherein the housing defines an open end retention chamber, and the element is secured within the retention chamber.

24. The medical device of claim 23, further comprising a removable cover secured to the housing over the open end of the retention chamber.

25. The medical device of claim 24 wherein the element is hermetically sealed within the retention chamber.

26. The medical device of claim 23 wherein the housing defines a pair of open end retention chambers, and wherein the device includes two elements with one of the elements secured within each of the retention chambers.

27. The medical device of claim 26, further comprising a removable cover secured to the housing over the open end of both retention chambers.

28. The medical device of claim 26, further comprising separate and independent first and second removable covers, each secured to the housing over the open end of one of the retention chambers.

29. The medical device of claim 23, further comprising a visual indicator to indicate the element has effected at least one of cleaning, disinfecting, sterilizing and drying of a medical end-site engaged by the element whereby the indicator signifies the medical end-site is ready for use.

30. The medical device of claim 29 wherein the visual indicator is attached to the housing.

31. The medical device of claim 29 wherein the visual indicator is attached to the element.

32. The medical device of claim 29 wherein the visual indicator is embodied in the element.

33. The medical device of claim 29, wherein the visual indicator is a visual color change indicator.

34. The medical device of claim 1, wherein the element has a lining of flexible material.

35. The medical device of claim 1, wherein the element has a protective skin.

36. The medical device of claim 4, wherein the mating projection is shaped and located within the cavity to contact and engage at least one of the surface defining the lumen, a septum sealing the lumen, and a port of a needleless connector.

37. The medical device of claim 4, wherein the mating projection on the element is shaped and located within the cavity to contact and engage a septum of a needleless connector mated with the element.

38. The medical device of claim 4, wherein the mating projection on the element is shaped and located within the cavity to project into the lumen of the medical end-site when the medical device is mated to the medical end-site.

39. The medical device of claim 4, wherein the mating projection on the element is shaped and located within the cavity to contact and engage a distal tip of the medical end-site when the medical device is mated to the medical end-site.

40. The medical device of claim 4, wherein the mating projection on the element is configured within the cavity to contact an end on a lumen tip of a male slip luer on a medical-endsite when the medical device is mated to the medical end-site.

41. The medical device of claim 1, wherein the element is formed by one of heat-setting, molding, pressure-molding, injection-molding, coring, laser cutting, and die cutting.

42. The medical device of claim 1, wherein the element is formed by one of molding, injection molding, transfer molding, compression molding and press molding.

43. The medical device of claim 1, wherein the element is operable for disinfecting the medical end-site contour feature by at least one of friction, wiping, twisting, dabbing, pushing, pulling, and rotation of the element on the medical end-site.

44. The medical device of claim 1, wherein the element is operable for sterilizing the medical end-site contour feature by at least one of friction, wiping, twisting, dabbing, pushing, pulling, and rotation of the element on the medical end-site.

45. The medical device of claim 1, wherein the form-fitting pre-shaped surface contour structure on the element engages a contour feature on the medical end-site selected from a contour feature on a female luer, a male luer, a slip luer, a luer hub, a luer compatible connector, a needle access port, a needleless connector, a catheter hub and an access port when the medical device is mated to the medical end-site.

46. The medical device of claim 1, wherein the form-fitting pre-shaped surface contour structure on the element engages a contour feature on the medical end-site selected from a septum sealing a lumen, a side surface, an edge surface, a thread or an inner surface defining a lumen.

47. The medical device of claim 1, wherein the element is comprised of a material selected from a viscoelastic foam, a shaped foam, a sponge, a non-woven, a particulate-free foam and a polyurethane.

48. The medical device of claim 1, wherein the element is comprised of an elastomer.

49. The medical device of claim 1, wherein the element is comprised of a material selected from a thermoplastic, a cellular thermoplastic, a silicone, a silicone rubber, a latex free rubber and an elastomer.

50. The medical device of claim 1, wherein the element is comprised of a porous polymeric material.

51. The medical device of claim 13, wherein the antipathogenic agent is physically associated with the element by a mechanism selected from retention, bonding, absorption and impregnation.

52. The medical device of claim 13, wherein the element retains and applies the antipathogenic agent onto the surface of the medical end-site when the element is pressed onto and received by the medical end-site.

53. The medical device of claim 1, wherein the element has at least one characteristic selected from porous, absorbent, micro-porous, micro-textured and micro-patterned.

54. The medical device of claim 1, wherein the form-fitting pre-shaped surface contour structure on the element has a surface characteristic selected from microporous and microtextured.

55. The medical device of claim 1, wherein the element has at least one characteristic selected from porous, absorbent, micro-porous, micro-textured, micro-patterned, micro-contoured, nano-porous, nano-textured, nano-patterned and nano-contoured.

56. The medical device of claim 1, wherein the form-fitting pre-shaped surface contour structure on the element has a surface characteristic selected from micro-porous, micro-textured, micro-patterned, micro-contoured, nano-porous, nano-textured, nano-patterned and nano-contoured.

57. The medical device of claim 56, wherein the form-fitting pre-shaped surface contour structure on the element has a characteristic selected from micro-textured and micro-patterned with at least one of ridges, bumps, surface roughing, rings, concentric circles, dimples and lattice.

58. The medical device of claim 13, wherein the antipathogenic agent is selected from antipathogenic microparticles, antipathogenic nano-particles and combinations thereof.

59. The medical device of claim 58, wherein the antipathogenic agent is activated by an action selected from contact, friction and a combination thereof.

60. The medical device of claim 13, wherein the antipathogenic agent disrupts the membrane of pathogens.

61. The medical device of claim 13, wherein the medical device is effective for leaving an antipathogenic residue on the medical end-site after the element contacts and is removed from the medical end-site.

62. The medical device of claim 1, wherein the element exhibits capillary action.

63. The medical device of claim 14, wherein the wet antipathogenic agent is dispersed throughout the element and remains dispersed regardless of the element's spatial orientation relative to gravity.

64. The medical device of claim 13 wherein the antipathogenic agent is a controlled release antipathogenic agent.

65. The medical device of claim 13, wherein the antipathogenic agent comprises an oligodynamic metal.

66. The medical device of claim 1, wherein the element defines a cavity and the form-fitting pre-shaped surface contour structure on the element is configured and arranged to wipe the contour feature of the medical end-site when the medical end-site is press fit into the cavity.

67. The medical device of claim 1, wherein the element has an exterior surface with a finger grip contour formed on the exterior surface of the element.

68. The medical device of claim 1, wherein the element has a textured exterior surface for facilitated finger gripping and manipulation of the element by a user.

69. The medical device of claim 13, wherein the medical device is effective for disinfecting the surface of the medical end-site in less than 10 seconds after the medical device engages the medical end-site.

70. The medical device of claim 13, wherein the medical device is effective for sterilizing the medical end-site in less than 5 seconds after the medical device engages the medical end-site.

71. The medical device of claim 61, wherein the antipathogenic residue left on the medical end-site after removal of the medical device from the medical end-site evaporates in less than 15 seconds at room temperature.

72. The medical device of claim 1, wherein the element is comprised of two or more members joined together to form the element.

73. The medical device of claim 26, wherein the elements are formed of materially different materials.

74. The medical device of claim 73, wherein the materially different materials have a difference in compliance.

75. The medical device of claim 23, wherein the element defines an open end cavity, and the element is configured and arranged within the housing for accepting the medical end-site within the cavity through the open end of the cavity with the element secured within the retention chamber.

76. The medical device of claim 75, further comprising a removable cover secured to the housing over the open end of the retention chamber and over the open end of the cavity.

77. The medical device of claim 75, further comprising a cap for engagement with the housing over the open end of the retention chamber.

78. The medical device of claim 75, wherein the element is removably secured within the retention chamber.

79. The medical device of claim 78, wherein the element has a protective skin.

80. The medical device of claim 79, wherein the protective skin is operable for preventing the element from drying out.

81. The medical device of claim 75, wherein (i) the cavity has a base end opposite the open end, (ii) the cavity defines a longitudinal axis which extends from the open end of the cavity to the base end of the cavity, and (iii) the element is releasable from the retention chamber by rotation of the housing relative to the element about the longitudinal axis.

82. The medical device of claim 76, wherein the removable cover is comprised of a semi-rigid material.

83. The medical device of claim 82, wherein the semi-rigid material is a flexible material selected from a plastic, a foil, and a laminated foil.

84. The medical device of claim 75, wherein the element is a first element and the medical device further includes a second element adjoined with the first element.

85. The medical device of claim 84, wherein the first element is configured to interface with the second element.

86. The medical device of claim 84, wherein the first element is configured to contact and engage with a portion of the second element.

87. The medical device of claim 84, wherein the medical device further comprises a supply of liquid antipathogenic agent, and the first element and the second element are in shared fluid communication with the supply of liquid antipathogenic agent.

88. The medical device of claim 84, wherein (i) the retention chamber is a first retention chamber, (ii) the first element is removably secured within the first retention chamber, (iii) the housing defines a second retention chamber, and (iv) the second element is removably secured within the second retention chamber.

89. The medical device of claim 88, wherein (i) the second element defines a second cavity wherein the second cavity has an open end and a base end opposite the open end, (ii) the second cavity defines a second longitudinal axis which extends from the open end of the second cavity to the base end of the second cavity, and (iii) the second element is releasable from the second retention chamber by rotation of the housing relative to the second element about the second longitudinal axis.

90. The medical device of claim 84, wherein the first element is operable while retained on the medical end-site to disinfect the surface of the medical end-site and protect against contamination of the surface of the medical end-site.

91. The medical device of claim 84, wherein the second element is operable while retained on the medical end-site to disinfect the surface of the medical end-site and protect against contamination of the surface of the medical end-site.

92. The medical device of claim 75, wherein the housing has a rectangular cross-section.

93. The medical device of claim 75, wherein the housing is configured to secure onto a syringe end.

94. The medical device of claim 75, wherein the housing is configured to secure the housing to a mating feature on a syringe end.

95. The medical device of claim 94, wherein the housing is configured to cover a syringe end, and the housing is operable as an end-cap for the syringe end, whereby the housing can be coupled to a syringe for future use of the element to effect at least one of cleaning, disinfecting, sterilizing and drying of the medical end-site.

96. The medical device of claim 75, wherein (i) the retention chamber has a base end opposite the open end, (ii) the retention chamber defines a longitudinal axis which extends from the open end of the retention chamber to the base end of the retention chamber, (iii) the housing has a sidewall inner surface defining a sidewall of the retention chamber, and (iv) the sidewall inner surface of the housing is a high-friction contact surface, whereby rotation of the housing about the longitudinal axis effects rotation of the element secured within the retention chamber.

97. The medical device of claim 96, wherein the housing inner surface has a characteristic selected from a gripable surface and a textured surface.

98. The medical device of claim 75, wherein the housing has a sidewall inner surface defining a sidewall of the retention chamber and a sidewall outer surface, and the housing sidewall outer surface has a feature to facilitate fingertip pinch gripping of the housing.

99. The medical device of claim 98, wherein the feature to facilitate fingertip pinch gripping of the housing is a plurality of fingertip locating indents.

100. The medical device of claim 98, wherein the feature to facilitate fingertip pinch gripping of the housing is one or more finger locating recesses formed in the housing sidewall outer surface.

101. The medical device of claim 1, wherein the form-fitting pre-shaped surface contour structure is a resilient contour structure.

102. The medical device of claim 1, wherein the form-fitting pre-shaped surface contour structure on the element is configured to conform to a contour feature of the medical end-site.

103. The medical device of claim 10, wherein the form-fitting pre-shaped surface contour structure on the element is configured to conform to a contour feature of the medical end-site.

104. The medical device of claim 1, wherein the element defines a cavity shaped by the form-fitting pre-shaped surface contour structure on the element, and the form-fitting pre-shaped surface contour structure includes a base portion surface shaped to form-fit a medical end-site contour feature.

105. The medical device of claim 104, wherein the base portion surface is a depressible base portion surface capable of conforming to the medical end-site when the medical end-site is pressed into the cavity.

106. The medical device of claim 104, wherein the base portion surface is a depressible raised shape whereby the raised shaped base portion surface conforms to the medical end-site when the medical end-site is pressed into the cavity.

107. The medical device of claim 106, wherein the raised shaped base portion surface is configured to engage and occlude the lumen on the medical end-site.

108. The medical device of claim 1, wherein the element defines at least one slit extending into the element and shaped to define the form-fitting pre-shaped surface contour structure.

109. The medical device of claim 1, wherein the element has a first end and a second end and at least one end defines a cavity shaped by the form-fitting pre-shaped surface contour structure on the element.

110. The medical device of claim 109, wherein the first end of the element comprises a first cavity shaped by a first form-fitting pre-shaped surface contour structure on the element and the second end of the element comprises a second cavity shaped by a second form-fitting pre-shaped surface contour structure on the element.

* * * * *